United States Patent
Chabal et al.

(10) Patent No.: US 12,296,129 B2
(45) Date of Patent: May 13, 2025

(54) SYSTEMS AND METHODS FOR IMPROVED PAIN RELIEF FROM STIMULATION OF THERMAL FIBERS

(71) Applicant: Soovu Labs, Inc., Seattle, WA (US)

(72) Inventors: Charles Chabal, Seattle, WA (US); Peter J. Dunbar, Seattle, WA (US); Allan Stephan, Seattle, WA (US); Jack Profit, Seattle, WA (US)

(73) Assignee: Soovu Labs, Inc., Seattle, WA (US)

( * ) Notice: Subject to any disclaimer, the term of this patent is extended or adjusted under 35 U.S.C. 154(b) by 1148 days.

(21) Appl. No.: 16/978,385

(22) PCT Filed: Mar. 7, 2019

(86) PCT No.: PCT/US2019/021203
§ 371 (c)(1),
(2) Date: Sep. 4, 2020

(87) PCT Pub. No.: WO2019/173623
PCT Pub. Date: Sep. 12, 2019

(65) Prior Publication Data
US 2021/0052869 A1    Feb. 25, 2021

Related U.S. Application Data

(60) Provisional application No. 62/639,930, filed on Mar. 7, 2018.

(51) Int. Cl.
*A61M 37/00*        (2006.01)
*A61F 7/02*         (2006.01)
(Continued)

(52) U.S. Cl.
CPC .............. *A61M 37/00* (2013.01); *A61F 7/02* (2013.01); *A61K 9/0014* (2013.01);
(Continued)

(58) Field of Classification Search
CPC ...... A61F 2007/0285; A61F 7/00; A61F 7/02; A61K 31/045; A61K 31/165;
(Continued)

(56) References Cited

U.S. PATENT DOCUMENTS

| 1,377,158 A | 5/1921 | Radisson |
| 3,841,306 A | 10/1974 | Hallgren |

(Continued)

FOREIGN PATENT DOCUMENTS

| CA | 2860977 | 1/2022 |
| CN | 102227198 | 10/2011 |

(Continued)

OTHER PUBLICATIONS

International Search Report and Written Opinion, issued for International Application No. PCT/US2021/035536, Mailing Date: Nov. 18, 2021, 25 pages.
(Continued)

*Primary Examiner* — Michael F Peffley
(74) *Attorney, Agent, or Firm* — Perkins Coie LLP

(57) ABSTRACT

The present technology includes systems and methods for treating pain by pulsing heat into a volume of tissue containing thermoreceptors. The pulsed heat may be configured to induce stimulation of thermoreceptors. The pulsed heat may also be applied at a frequency configured to induce desensitization of at least a subset of the thermoreceptors.

31 Claims, 22 Drawing Sheets

(51) Int. Cl.
*A61K 9/00* (2006.01)
*A61K 31/045* (2006.01)
*A61K 31/165* (2006.01)
*A61K 31/167* (2006.01)
*A61K 31/513* (2006.01)
*A61K 36/185* (2006.01)
*A61K 41/00* (2020.01)
*A61K 45/06* (2006.01)

(52) U.S. Cl.
CPC .......... *A61K 31/045* (2013.01); *A61K 31/165* (2013.01); *A61K 31/167* (2013.01); *A61K 31/513* (2013.01); *A61K 36/185* (2013.01); *A61K 41/0052* (2013.01); *A61K 45/06* (2013.01); *A61F 2007/0285* (2013.01); *A61M 2037/0007* (2013.01); *A61M 2205/3303* (2013.01)

(58) Field of Classification Search
CPC .. A61K 31/167; A61K 31/513; A61K 36/185; A61K 41/0052; A61K 45/06; A61K 9/0014; A61M 2037/0007; A61B 18/10; A61B 18/1206; A61B 18/08; A61B 18/04
See application file for complete search history.

(56) References Cited

U.S. PATENT DOCUMENTS

| | | |
|---|---|---|
| 3,857,397 A | 12/1974 | Brosseau |
| 4,107,509 A | 8/1978 | Scher et al. |
| 4,201,218 A | 5/1980 | Feldman et al. |
| 4,245,149 A | 1/1981 | Fairlie |
| 4,279,255 A | 7/1981 | Hoffman |
| 4,303,074 A | 12/1981 | Bender |
| 4,310,745 A | 1/1982 | Bender |
| 4,348,584 A | 9/1982 | Gale et al. |
| 4,396,011 A | 8/1983 | Mack et al. |
| 4,398,535 A | 8/1983 | Guibert |
| 4,487,603 A | 12/1984 | Harris |
| 4,518,851 A | 5/1985 | Oppitz |
| 4,570,640 A | 2/1986 | Barsa |
| 4,575,097 A | 3/1986 | Brannigan et al. |
| 4,585,002 A * | 4/1986 | Kissin ................... A61F 7/007 607/96 |
| 4,608,985 A | 9/1986 | Crish |
| 4,719,919 A | 1/1988 | Marchosky |
| 4,736,088 A | 4/1988 | Bart |
| 4,817,628 A | 4/1989 | Zealear |
| 4,889,526 A | 12/1989 | Rauscher |
| 4,930,317 A | 6/1990 | Klein |
| 4,939,149 A | 7/1990 | Blumberg |
| 5,031,618 A | 7/1991 | Mullett |
| 5,035,891 A | 7/1991 | Runkel |
| 5,057,104 A | 10/1991 | Chess |
| 5,061,234 A | 10/1991 | Chaney |
| 5,092,835 A | 3/1992 | Schurig |
| 5,097,828 A | 3/1992 | Deutsch |
| 5,138,138 A | 8/1992 | Theilacker et al. |
| 5,188,104 A | 2/1993 | Vvernicke |
| 5,192,527 A | 3/1993 | Abrahmsohn |
| 5,215,089 A | 6/1993 | Baker, Jr. |
| 5,224,927 A | 7/1993 | Tapper |
| 5,224,928 A | 7/1993 | Sibalis |
| 5,231,988 A | 8/1993 | Wernicke |
| 5,251,634 A | 10/1993 | Weinberg |
| 5,330,515 A | 7/1994 | Rutecki |
| 5,335,657 A | 8/1994 | Terry, Jr. |
| 5,336,255 A | 8/1994 | Kanare et al. |
| 5,351,394 A | 10/1994 | Weinberg |
| 5,354,320 A | 10/1994 | Schaldach |
| 5,374,284 A | 12/1994 | Guibert et al. |
| 5,395,398 A | 3/1995 | Rogozinski |
| 5,423,874 A | 6/1995 | D'Alerta |
| 5,447,530 A | 9/1995 | Guibert et al. |
| 5,451,747 A | 9/1995 | Sullivan et al. |
| 5,458,625 A | 10/1995 | Kendall |
| 5,499,967 A | 3/1996 | Teillaud |
| 5,527,797 A | 6/1996 | Eisenberg |
| 5,531,778 A | 7/1996 | Maschino |
| 5,540,730 A | 7/1996 | Terry, Jr. |
| 5,558,633 A | 9/1996 | Phipps |
| 5,571,150 A | 11/1996 | Wernicke |
| 5,580,350 A | 12/1996 | Guibert et al. |
| 5,601,618 A | 2/1997 | James |
| 5,628,769 A | 5/1997 | Saringer |
| 5,658,583 A | 8/1997 | Zhang et al. |
| 5,683,422 A | 11/1997 | Rise |
| 5,707,400 A | 1/1998 | Terry, Jr. |
| 5,735,889 A | 4/1998 | Burkett et al. |
| 5,741,318 A | 4/1998 | Ouellette et al. |
| 5,755,750 A | 5/1998 | Petruska |
| 5,797,898 A | 8/1998 | Santini, Jr. et al. |
| 5,800,481 A * | 9/1998 | Loos ................... A61N 1/403 607/100 |
| 5,814,019 A | 9/1998 | Steinbach |
| 5,817,139 A | 10/1998 | Kasano |
| 5,817,145 A | 10/1998 | Augustine et al. |
| 5,830,207 A | 11/1998 | Leeb |
| 5,830,208 A | 11/1998 | Muller |
| 5,837,005 A | 11/1998 | Viltro et al. |
| 5,860,945 A | 1/1999 | Cramer et al. |
| 5,861,022 A | 1/1999 | Hipskind |
| 5,868,743 A | 2/1999 | Saul |
| 5,876,422 A | 3/1999 | Van Groeningen |
| 5,891,189 A | 4/1999 | Payne, Jr. |
| 5,893,991 A | 4/1999 | Newell |
| 5,906,637 A | 5/1999 | Davis et al. |
| 5,925,072 A | 7/1999 | Cramer et al. |
| 5,928,195 A | 7/1999 | Malamud et al. |
| 5,947,914 A | 9/1999 | Augustine |
| 5,954,680 A | 9/1999 | Augustine |
| 5,964,721 A | 10/1999 | Augustine |
| 5,964,723 A | 10/1999 | Augustine |
| 5,984,995 A | 11/1999 | White |
| 5,986,163 A | 11/1999 | Augustine |
| 5,993,414 A | 11/1999 | Haller |
| 5,997,501 A | 12/1999 | Gross |
| 6,010,527 A | 1/2000 | Augustine et al. |
| 6,012,457 A | 1/2000 | Lesh |
| 6,013,097 A | 1/2000 | Augustine et al. |
| 6,045,518 A | 4/2000 | Augustine |
| 6,058,331 A | 5/2000 | King |
| 6,066,163 A | 5/2000 | John |
| 6,066,164 A | 5/2000 | Macher et al. |
| 6,071,254 A | 6/2000 | Augustine |
| 6,095,992 A | 8/2000 | Augustine |
| 6,096,067 A | 8/2000 | Cramer et al. |
| 6,110,197 A | 8/2000 | Augustine et al. |
| 6,113,561 A | 9/2000 | Augustine |
| 6,146,732 A | 11/2000 | Davis et al. |
| 6,164,283 A | 12/2000 | Lesh |
| 6,185,455 B1 | 2/2001 | Loeb |
| 6,208,894 B1 | 3/2001 | Schulman |
| 6,213,965 B1 | 4/2001 | Augustine et al. |
| 6,213,966 B1 | 4/2001 | Augustine |
| 6,217,535 B1 | 4/2001 | Augustine |
| 6,235,049 B1 | 5/2001 | Nazerian |
| 6,238,421 B1 | 5/2001 | Gunther et al. |
| 6,241,697 B1 | 6/2001 | Augustine |
| 6,246,912 B1 | 6/2001 | Sluijter |
| 6,248,084 B1 | 6/2001 | Augustine et al. |
| 6,248,126 B1 | 6/2001 | Lesser |
| 6,254,557 B1 | 7/2001 | Augustine et al. |
| 6,264,622 B1 | 7/2001 | Augustine |
| 6,267,740 B1 | 7/2001 | Augustine et al. |
| 6,283,931 B1 | 9/2001 | Augustine |
| 6,293,917 B1 | 9/2001 | Augustine et al. |
| 6,314,325 B1 | 11/2001 | Fitz |
| 6,326,020 B1 | 12/2001 | Kohane |
| 6,331,695 B1 | 12/2001 | West |
| 6,353,211 B1 | 3/2002 | Chen |
| 6,364,899 B1 | 4/2002 | Dobak, III |
| 6,405,732 B1 | 6/2002 | Edwards |

(56) References Cited

U.S. PATENT DOCUMENTS

| | | |
|---|---|---|
| 6,406,448 B1 | 6/2002 | Augustine |
| 6,407,307 B1 | 6/2002 | Augustine |
| 6,416,495 B1 | 7/2002 | Kriesel |
| 6,419,651 B1 | 7/2002 | Augustine |
| 6,423,018 B1 | 7/2002 | Augustine |
| 6,436,063 B1 | 8/2002 | Augustine et al. |
| 6,453,195 B1 | 9/2002 | Thompson |
| 6,454,759 B2 | 9/2002 | Krulevitch |
| 6,464,687 B1 | 10/2002 | Akira |
| 6,465,709 B1 | 10/2002 | Sun et al. |
| 6,468,295 B2 | 10/2002 | Augustine et al. |
| 6,485,506 B2 | 11/2002 | Augustine |
| 6,527,695 B1 | 3/2003 | Davey |
| 6,528,076 B2 | 3/2003 | Small |
| 6,539,250 B1 | 3/2003 | Bettinger |
| 6,551,235 B2 | 4/2003 | Forsell |
| 6,554,822 B1 | 4/2003 | Holschneider |
| 6,567,696 B2 | 5/2003 | Voznesensky et al. |
| 6,571,123 B2 | 5/2003 | Ives |
| 6,571,125 B2 | 5/2003 | Thompson |
| 6,572,871 B1 | 6/2003 | Church et al. |
| 6,580,012 B1 | 6/2003 | Augustine et al. |
| 6,589,271 B1 | 7/2003 | Tzeng |
| 6,600,956 B2 | 7/2003 | Maschino |
| 6,605,012 B2 | 8/2003 | Muller |
| 6,610,713 B2 | 8/2003 | Tracey |
| 6,622,048 B1 | 9/2003 | Mann |
| 6,666,845 B2 | 12/2003 | Hooper |
| 6,669,683 B2 | 12/2003 | Santini, Jr. et al. |
| 6,684,105 B2 | 1/2004 | Cohen |
| 6,710,313 B1 | 3/2004 | Asami et al. |
| 6,716,235 B2 | 4/2004 | Augustine et al. |
| 6,720,402 B2 | 4/2004 | Langer |
| 6,745,078 B1 | 6/2004 | Buchner |
| 6,746,474 B2 | 6/2004 | Saadat |
| 6,755,621 B2 | 6/2004 | Lopez |
| 6,761,715 B2 | 7/2004 | Carroll |
| 6,764,678 B2 | 7/2004 | Weber |
| 6,770,022 B2 | 8/2004 | Mechlenburg |
| 6,796,956 B2 | 9/2004 | Hartlaub et al. |
| 6,802,811 B1 | 10/2004 | Slepian |
| 6,808,522 B2 | 10/2004 | Richards |
| 6,832,114 B1 | 12/2004 | Whitehurst et al. |
| 6,835,184 B1 | 12/2004 | Sage |
| 6,838,471 B2 | 1/2005 | Tracey |
| 6,840,915 B2 | 1/2005 | Augustine |
| 6,840,955 B2 | 1/2005 | Ein |
| 6,860,852 B2 | 3/2005 | Schoenenberger |
| 6,871,092 B2 | 3/2005 | Piccone |
| 6,871,099 B1 | 3/2005 | Whitehurst et al. |
| 6,885,888 B2 | 4/2005 | Rezai |
| 6,893,453 B2 | 5/2005 | Agarwal et al. |
| 6,921,374 B2 | 7/2005 | Augustine |
| 6,921,413 B2 | 7/2005 | Mahadevan-Jansen |
| 6,925,317 B1 | 8/2005 | Samuels |
| 6,928,320 B2 | 8/2005 | King |
| 6,941,171 B2 | 9/2005 | Mann |
| 6,976,982 B2 | 12/2005 | Santini, Jr. et al. |
| 6,978,174 B2 | 12/2005 | Gelfand |
| 7,016,723 B2 | 3/2006 | Morris |
| 7,022,093 B2 | 4/2006 | Smith et al. |
| 7,031,768 B2 | 4/2006 | Anderson |
| 7,033,571 B2 | 4/2006 | Gutowska |
| 7,072,802 B2 | 7/2006 | Hartlaub |
| 7,076,307 B2 | 7/2006 | Boveja et al. |
| 7,108,680 B2 | 9/2006 | Rohr |
| 7,113,821 B1 | 9/2006 | Sun |
| 7,155,279 B2 | 12/2006 | Whitehurst et al. |
| 7,155,281 B1 | 12/2006 | Fayram |
| 7,162,303 B2 | 1/2007 | Levin et al. |
| 7,167,743 B2 | 1/2007 | Heruth |
| 7,204,832 B2 | 4/2007 | Altshuler |
| 7,204,833 B1 | 4/2007 | Osorio |
| 7,209,787 B2 | 4/2007 | DiLorenzo |
| 7,209,788 B2 | 4/2007 | Nicolelis et al. |
| 7,226,426 B2 | 6/2007 | Thomson |
| 7,231,254 B2 | 6/2007 | DiLorenzo |
| 7,236,822 B2 | 6/2007 | Dobak, III |
| 7,242,983 B2 | 7/2007 | Frei |
| 7,244,253 B2 | 7/2007 | Neev |
| 7,263,405 B2 | 8/2007 | Boveja et al. |
| 7,277,758 B2 | 10/2007 | DiLorenzo |
| 7,286,880 B2 | 10/2007 | Olson |
| 7,315,761 B2 | 1/2008 | De Ridder |
| 7,319,899 B2 | 1/2008 | Keizer |
| 7,324,851 B1 | 1/2008 | DiLorenzo |
| 7,337,005 B2 | 2/2008 | Kim |
| 7,337,006 B2 | 2/2008 | Kim |
| 7,340,304 B2 | 3/2008 | MacDonald |
| 7,389,145 B2 | 6/2008 | Kilgore |
| 7,613,515 B2 | 11/2009 | Knudson |
| 7,634,317 B2 | 12/2009 | Ben-David et al. |
| 7,672,714 B2 | 3/2010 | Kuo |
| 7,783,361 B2 | 8/2010 | Docherty et al. |
| 7,871,427 B2 | 1/2011 | Dunbar et al. |
| 8,060,208 B2 | 11/2011 | Kilgore |
| 8,082,039 B2 | 12/2011 | Kim et al. |
| 8,160,695 B2 | 4/2012 | Dacey, Jr. et al. |
| 8,165,668 B2 | 4/2012 | Dacey, Jr. et al. |
| 8,165,669 B2 | 4/2012 | Dacey, Jr. et al. |
| 8,170,658 B2 | 5/2012 | Dacey, Jr. et al. |
| 8,170,659 B2 | 5/2012 | Dacey, Jr. et al. |
| 8,170,660 B2 | 5/2012 | Dacey, Jr. et al. |
| 8,180,446 B2 | 5/2012 | Dacey, Jr. et al. |
| 8,180,447 B2 | 5/2012 | Dacey, Jr. et al. |
| 8,195,287 B2 | 6/2012 | Dacey, Jr. et al. |
| 8,233,976 B2 | 7/2012 | Dacey, Jr. et al. |
| 8,244,369 B2 * | 8/2012 | Kreindel ............... A61B 18/14 |
| | | 607/101 |
| 8,391,970 B2 | 3/2013 | Tracey |
| 8,412,338 B2 | 4/2013 | Faltys |
| 8,579,953 B1 * | 11/2013 | Dunbar .................... A61F 7/007 |
| | | 607/99 |
| 8,630,706 B2 | 1/2014 | Dacey, Jr. et al. |
| 8,702,775 B2 | 4/2014 | Dunbar et al. |
| 8,989,858 B2 | 3/2015 | Dacey, Jr. et al. |
| 9,014,802 B2 | 4/2015 | Dacey, Jr. et al. |
| 9,020,591 B2 | 4/2015 | Dacey, Jr. et al. |
| 9,020,592 B2 | 4/2015 | Dacey, Jr. et al. |
| 9,358,374 B2 | 6/2016 | Dacey, Jr. et al. |
| 9,789,315 B2 | 10/2017 | Dacey, Jr. et al. |
| 9,937,072 B2 | 4/2018 | Chabal et al. |
| 10,092,692 B2 | 10/2018 | Dacey, Jr. et al. |
| 10,182,937 B2 * | 1/2019 | Smith .................... G01K 1/143 |
| 10,188,547 B2 | 1/2019 | Dunbar et al. |
| 10,603,208 B2 | 3/2020 | Dunbar et al. |
| 2001/0037104 A1 | 11/2001 | Zhang et al. |
| 2002/0019652 A1 | 2/2002 | Da Silva et al. |
| 2002/0026226 A1 | 2/2002 | Ein |
| 2002/0038137 A1 | 3/2002 | Stein |
| 2002/0058972 A1 | 5/2002 | Minogue |
| 2002/0068964 A1 | 6/2002 | Dobak, III |
| 2002/0095134 A1 | 7/2002 | Pettis et al. |
| 2002/0173827 A1 | 11/2002 | Jones et al. |
| 2002/0183813 A1 | 12/2002 | Augustine et al. |
| 2003/0013998 A1 | 1/2003 | Augustine |
| 2003/0014097 A1 | 1/2003 | Putz et al. |
| 2003/0045914 A1 | 3/2003 | Cohen |
| 2003/0050677 A1 | 3/2003 | Gross |
| 2003/0060860 A1 | 3/2003 | Foster et al. |
| 2003/0069618 A1 | 4/2003 | Smith et al. |
| 2003/0097161 A1 | 5/2003 | Firlik et al. |
| 2003/0125648 A1 | 7/2003 | Leason et al. |
| 2003/0125661 A1 | 7/2003 | Yerushalmy |
| 2003/0176901 A1 | 9/2003 | May |
| 2003/0219470 A1 | 11/2003 | Zhang et al. |
| 2004/0013716 A1 | 1/2004 | Gale et al. |
| 2004/0049134 A1 | 3/2004 | Tosaya et al. |
| 2004/0073258 A1 | 4/2004 | Church et al. |
| 2004/0098065 A1 | 5/2004 | Hagglof et al. |
| 2004/0127886 A1 | 7/2004 | Daum |
| 2004/0172086 A1 | 9/2004 | Knudson |
| 2004/0176812 A1 | 9/2004 | Knudson |
| 2004/0181262 A1 | 9/2004 | Bauhahn |

(56) References Cited

U.S. PATENT DOCUMENTS

| | | |
|---|---|---|
| 2004/0211569 A1 | 10/2004 | Vinegar et al. |
| 2004/0220621 A1 | 11/2004 | Zhou et al. |
| 2005/0021103 A1 | 1/2005 | DiLorenzo |
| 2005/0021104 A1 | 1/2005 | DiLorenzo |
| 2005/0070974 A1 | 3/2005 | Knudson et al. |
| 2005/0075669 A1 | 4/2005 | King |
| 2005/0075701 A1 | 4/2005 | Shafer |
| 2005/0075702 A1 | 4/2005 | Shafer |
| 2005/0076908 A1 | 4/2005 | Lee et al. |
| 2005/0080463 A1 | 4/2005 | Stahmann et al. |
| 2005/0119713 A1 | 6/2005 | Whitehurst et al. |
| 2005/0125044 A1 | 6/2005 | Tracey |
| 2005/0137648 A1 | 6/2005 | Cosendai et al. |
| 2005/0138934 A1 | 6/2005 | Weigert et al. |
| 2005/0149123 A1 | 7/2005 | Lesser |
| 2005/0149148 A1 | 7/2005 | King |
| 2005/0203501 A1 | 9/2005 | Aldrich |
| 2005/0215947 A1 | 9/2005 | Heruth |
| 2005/0216072 A1 | 9/2005 | Mahadevan-Jansen |
| 2005/0234523 A1 | 10/2005 | Levin et al. |
| 2005/0240126 A1 | 10/2005 | Foley et al. |
| 2005/0256555 A1 | 11/2005 | Fisher et al. |
| 2005/0273029 A1 | 12/2005 | Harris et al. |
| 2005/0277912 A1 | 12/2005 | John |
| 2005/0278001 A1 | 12/2005 | Qin |
| 2005/0282906 A1 | 12/2005 | Tracey |
| 2005/0288730 A1 | 12/2005 | Deem |
| 2006/0004417 A1 | 1/2006 | Rossing |
| 2006/0036209 A1 | 2/2006 | Subramony |
| 2006/0058694 A1 | 3/2006 | Clark |
| 2006/0100668 A1 | 5/2006 | Ben-David et al. |
| 2006/0122454 A1 | 6/2006 | Riehl |
| 2006/0122663 A1 | 6/2006 | Mandell |
| 2006/0122675 A1 | 6/2006 | Libbus |
| 2006/0155348 A1 | 7/2006 | Decharms |
| 2006/0173493 A1 | 8/2006 | Armstrong |
| 2006/0178703 A1 | 8/2006 | Huston et al. |
| 2006/0190053 A1 | 8/2006 | Dobak, III |
| 2006/0195168 A1 | 8/2006 | Dunbar et al. |
| 2006/0247721 A1 | 11/2006 | Maschino |
| 2006/0247722 A1 | 11/2006 | Maschino |
| 2006/0247739 A1 | 11/2006 | Wahlstrand |
| 2006/0258962 A1 | 11/2006 | Kopanic et al. |
| 2006/0259077 A1 | 11/2006 | Pardo |
| 2006/0270944 A1 | 11/2006 | King |
| 2006/0282134 A1 | 12/2006 | Shapiro |
| 2006/0293721 A1 | 12/2006 | Tarver |
| 2007/0027484 A1 | 2/2007 | Guzman |
| 2007/0027496 A1 | 2/2007 | Parnis |
| 2007/0027497 A1 | 2/2007 | Parnis |
| 2007/0055316 A1 | 3/2007 | Godara |
| 2007/0060984 A1 | 3/2007 | Webb |
| 2007/0093870 A1 | 4/2007 | Maschino |
| 2007/0106339 A1 | 5/2007 | Errico et al. |
| 2007/0129760 A1 | 6/2007 | Demarais |
| 2007/0129774 A1 | 6/2007 | Bourget |
| 2007/0135875 A1 | 6/2007 | Demarais |
| 2007/0142875 A1 | 6/2007 | Shalev |
| 2007/0150025 A1 | 6/2007 | DiLorenzo et al. |
| 2007/0150029 A1 | 6/2007 | Bourget |
| 2007/0156032 A1 | 7/2007 | Gordon |
| 2007/0156206 A1 | 7/2007 | Wahlstrand |
| 2007/0167984 A1 | 7/2007 | Kieval |
| 2007/0173899 A1 | 7/2007 | Levin et al. |
| 2007/0179557 A1 | 8/2007 | Steven |
| 2007/0191906 A1 | 8/2007 | Iyer |
| 2007/0225781 A1 | 9/2007 | Saadat et al. |
| 2007/0233211 A1 | 10/2007 | Galer |
| 2007/0255374 A1 | 11/2007 | Kolafa |
| 2008/0045879 A1 | 2/2008 | Prausnitz |
| 2008/0077198 A1 | 3/2008 | Webb |
| 2008/0091248 A1 | 4/2008 | Libbus |
| 2008/0103567 A1 | 5/2008 | Augustine et al. |
| 2008/0249439 A1 | 10/2008 | Tracey |
| 2008/0300657 A1 | 12/2008 | Stultz |
| 2008/0312522 A1 | 12/2008 | Rowlandson et al. |
| 2009/0062896 A1 | 3/2009 | Overstreet |
| 2009/0131835 A1 | 5/2009 | Voorhees et al. |
| 2009/0149797 A1 | 6/2009 | Dacey, Jr. et al. |
| 2009/0149798 A1 | 6/2009 | Dacey, Jr. et al. |
| 2009/0149799 A1 | 6/2009 | Dacey, Jr. et al. |
| 2009/0187230 A1 | 7/2009 | Dilorenzo |
| 2009/0222072 A1 | 9/2009 | Robinson et al. |
| 2009/0275997 A1 | 11/2009 | Faltys et al. |
| 2009/0292237 A1 | 11/2009 | Overstreet |
| 2010/0036445 A1 | 2/2010 | Sakai et al. |
| 2010/0256720 A1 | 10/2010 | Overstreet |
| 2011/0021930 A1 | 1/2011 | Mazzeo et al. |
| 2011/0054569 A1 | 3/2011 | Zitnik |
| 2011/0106208 A1 | 5/2011 | Faltys et al. |
| 2011/0190849 A1 | 8/2011 | Faltys et al. |
| 2011/0279963 A1 | 11/2011 | Kumar et al. |
| 2012/0290035 A1 | 11/2012 | Levin et al. |
| 2013/0041331 A1 | 2/2013 | Overstreet |
| 2013/0079749 A1 | 3/2013 | Overstreet |
| 2013/0079834 A1 | 3/2013 | Levine |
| 2014/0088580 A1 | 3/2014 | Wittenberger et al. |
| 2014/0148756 A1 | 5/2014 | Yodfat et al. |
| 2014/0207219 A1* | 7/2014 | Dunbar .................. A61F 7/007 |
| | | 607/96 |
| 2018/0064484 A1 | 3/2018 | Diederich et al. |
| 2018/0104407 A1 | 4/2018 | Dacey, Jr. et al. |
| 2018/0193078 A1 | 7/2018 | Rajagopalan et al. |
| 2019/0038456 A1 | 2/2019 | Chabal et al. |
| 2019/0142630 A1 | 5/2019 | Drnek et al. |
| 2019/0262626 A1 | 8/2019 | De Taboada et al. |
| 2020/0008973 A1 | 1/2020 | Dunbar et al. |
| 2020/0050248 A1* | 2/2020 | Smith ....................... A61F 7/00 |
| 2020/0345537 A1 | 11/2020 | Dunbar et al. |
| 2021/0145632 A1 | 5/2021 | Dunbar et al. |
| 2022/0085628 A1 | 3/2022 | Stephan |
| 2023/0218432 A1 | 7/2023 | Chabal et al. |

FOREIGN PATENT DOCUMENTS

| | | |
|---|---|---|
| CN | 112533561 | 3/2021 |
| CN | 201920906490.X | 4/2021 |
| CN | 113330659 | 8/2021 |
| DE | 102010016404 | 12/2012 |
| EP | 1462073 A1 | 9/2004 |
| EP | 2356958 | 8/2011 |
| EP | 2665457 | 6/2019 |
| EP | 3761925 | 1/2021 |
| EP | 3903402 | 11/2021 |
| JP | 62-44255 | 2/1987 |
| JP | 05-007613 | 1/1993 |
| JP | 05-161691 | 6/1993 |
| JP | H0576435 | 10/1993 |
| JP | 2004064726 | 2/2004 |
| JP | 2007500444 | 1/2007 |
| JP | 2007531562 | 11/2007 |
| JP | 2008513743 | 5/2008 |
| JP | 2008539953 | 11/2008 |
| JP | 2009537226 | 10/2009 |
| JP | 2016538972 | 12/2016 |
| JP | 6502612 | 4/2019 |
| JP | 2665457 | 10/2019 |
| JP | 2020110662 | 7/2020 |
| JP | 2021517024 | 7/2021 |
| JP | 6923501 | 8/2021 |
| JP | 2022517538 | 3/2022 |
| KR | 200382853 Y1 | 4/2005 |
| KR | 1020080095279 | 9/2005 |
| KR | 1020150127108 | 11/2015 |
| KR | 101603078 B1 | 3/2016 |
| WO | WO1987002891 | 5/1987 |
| WO | WO2005079295 | 9/2005 |
| WO | WO2006086513 | 8/2006 |
| WO | WO2008057884 | 5/2008 |
| WO | WO2009073208 | 6/2009 |
| WO | WO2009073223 | 6/2009 |
| WO | WO2009075783 | 6/2009 |
| WO | WO2011127918 | 10/2011 |
| WO | WO2014088768 | 6/2014 |

(56) References Cited

FOREIGN PATENT DOCUMENTS

| WO | WO2015054615 | 4/2015 |
|---|---|---|
| WO | WO2012100258 | 1/2018 |
| WO | WO2019173623 | 9/2019 |
| WO | WO2020139883 | 7/2020 |
| WO | WO2021247765 | 12/2021 |

OTHER PUBLICATIONS

ISA, International Search Report and Written Opinion, issued for International Application No. PCT/US2006/004506, Applicant: Carewave, Inc. Mail Date: Sep. 24, 2007, 7 pages.

ISA, International Search Report and Written Opinion, issued for International Application No. PCT/US2006/004506, Mail Date: Sep. 25, 2007, 10 pages.

ISA, International Search Report and Written Opinion, issued for International Application No. PCT/US2019/068477, Mail Date: May 12, 2020, 14 pages.

Official Notice of Rejection for JP Patent Application No. 2018-212186, dated Sep. 29, 2020, 7 pages (with unofficial translation).

Requisition by the Examiner for Canadian Application No. 2,860,977 dated Jan. 25, 2021 (3 pages).

Official Notice of Rejection for Japanese Patent Application No. 2020-069050 dated Apr. 27, 2021, 8 pages.

Notice of Allowance for Japanese Patent Application No. 2018-212186 dated Jun. 29, 2021, 6 pages.

European Extended Search Report, issued for EP Application No. 19763965.1, Mail Date: Nov. 9, 2021, 9 pages.

Requisition by the Examiner for Canadian Application No. 2,860,977 dated Oct. 18, 2019 (4 pages).

Non-Final Office Action, issued for U.S. Appl. No. 16/154,036, Applicant: Ralph G. Dacey, JR., mailed Apr. 30, 2020, 34 pages.

Non-Final Office Action, issued for U.S. Appl. No. 17/065,817, Applicant: Peter J. Dunbar, mailed Nov. 8, 2022, 35 pages.

Application Note-Rat Sciatic Nerve; Aculight corporation; bearing a date of Dec. 6, 2006; pp. • 1-2.

Belverud, Shawn; Mogilner, Alon; Schulder, Michael; Intrathecal Pumps; Neurotherapeutics: The Journal of the American Society for Experimental Neuro Therapeutics; Jan. 2008; pp. 114-122; vol. 5, No. 1.

Binshtok, Alexander M.; Bean, Bruce P.; Woolf, Clifford J.; Inhibition of Nociceptors by TRPVI-Mediated Entry of Impermeant Sodium Channel Blockers; Nature, Letters; bearing a date of Oct. 4, 2007; pp. 607-661 • 1; vol. 449; Nature Publishing Group.

Bjordal, Jan M.; Johnson, Mark I.; Lopes-Martins, Rodrigo AB; Bogen, Bard; Chow, Roberta; Ljunggren, Anne E.; Short-Term Efficacy of Physical Interventions in Osteoarthritic Knee Pain. A Systematic Review and Meta-Analysis of Randomized Placebo-Controlled Trials.; BMC Musculoskeletal Disorders, BioMed Central; 2007; pp. 1-34, plus cover page and Figs. 1-8; vol. 8, No. 51; Bio Med Centrai Ltd.; located at: http:i/wwvv.biomedcentral.com/14 71-24 74/8/51.

Boggs, Will; Physical Interventions can be Effective for Osteoarthritic Knee Pain; VVebMD; 1994-2007; pp. 1-2; Medscape; located at: http://www.medscane.com/viewarticle/559501; printed on Jul. 12, 2007.

Bostock, Hugh; Cikurel, Katia; Burke, David; Invited Review: Threshold Tracking Techniques in the Study of Human Peripheral Nerve; Muscle & Nerve; Feb. 1998; pp. 137-158; John Wiley & Sons, Inc.

Brooks, Jonathan; Tracey, Irene; Review: From Nociception to Pain Perception: Imaging the Spinal and Supraspinal Pathways; Journal of Anatomy; 2005; pp. 19-33; vol. 207; Anatomical Society of Great Britain and Ireland.

Burdakov, Denis; Gerasimenko, Oleg; Verkhratsky, Alexei; Brief Communication: Physiological Changes in Glucose Differentially Modulate the Excitability of Hypothalamic Melanin-Concentrating Hormone and Orexin Neurons In Situ; The Journal of Neuroscience; bearing a date of Mar. 2, 2005; pp. 2429-2433; vol. 25, No. 9.

Could Nerve-Snip Spur Weight Loss?; CNN.corn; 2007; pp. 1-2; Cable News Network; located at: http://www.crm.corn/2007/HEALTH/conditions/07/09/obesity.nerve.ap/index.html; printed on Jul. 12, 2007.

Device blocking stomach nerve signals shows promise in obesity, physorg.com, Mayo Clinic, bearing a date of Jun. 26, 2008, pp. 1-2; located at http://www.pilysorg.com/news/33701913.htrnl.

Douglas, W.W.; Malcom, J.L.; The Effect of Localized Cooling on Conduction in Cat Nerves; Journal of Physiology; 1955; pp. 53-71; vol. 130; located at: jp.physoc.org.

Fang, Zi-Ping; Mortimer, J. Thomas; Selective Activation of Small Motor Axons by Quasitrapezoidal Current Pulses; IEEE Transactions on Biomedical Engineering; Feb. 1991; pp. 168-174; vol. 38, No. 2; IEEE.

Franz, D.N.; lggo, A.; Conduction Failure in Myelinated and Non-Myelinated Axons at Low Temperatures; Journal of Physiology; 1968; pp. 319-345; vol. 199.

Gordon, Ryan D.; Peterson, Tim A; 4 Myths About Transdermal Drug Delivery; Drug Delivery Technology; bearing a date of Jun. 4, 2003 and posted on Mar. 28, 2008; pp. 1-9; vol. 3, No. 4.

Grayson, Amy C. Richards; Shawgo, Rebecca S.; Johnson, Audrey M.; Flynn, Nolan T.; Li, Yawen; Cima, Michael J.; Langer, Robert; A BioMEMS Review: MEMS Technology for Physiologically Integrated Devices; Proceedings of the IEEE; bearing a date of Jan. 2004; pp. 6-21; vol. 92, No. 1.

Han, Xue; Boyden, Edward S., Multiple-Color Optical Activation, Silencing, and Desynchronization of Neurai Activity, with Single-Spike Temporal Resolution; PLoS ONE; Mar. 2007; pp. 1-12; Issue 3, No. e299; located at www.piosone.org.

Harland, C.J.; Clark, T.D.; Prance, R.J.; Remote Detection of Human Electroencephalograms Using Ultrahigh Input Impedance Electric Potential Sensors; Applied Physics Letters; bearing a date of Oct. 21, 2002; pp. 3284-3286; vol. 81, No. 17; American institute of Physics.

Hinrikus, H.; Lass, J.; Tuulik, V.; Low-Level Microwave Effect on Nerve Pulse Propagation Velocity; Proceedings of the 25th Annual International Conference of the IEEE EMBS; bearing dates of Sep. 17, 2003-Sep. 21, 2003; pp. 3253-3256; IEEE.

Hodgkin, A.L.; Huxley, A.F.; A Quantitative Description of Membrane Current and its Application to Conduction and Excitation in Nerve; Journal of Physiology; 1952; pp. 500-544;voi. 117.

Hong, CZ; Reversible Nerve Conduction Block in Patients with Polyneuropathy After Ultrasound Thermotherapy at Therapeutic Dosage.; Archives of Physical Medicine and Rehabilitation; Feb. 1991, pp. 132-137, only the abstract is being provided; vol. 72, No. 2; located at: http://www.ncbi.nlm.nih.gov/sites/entrez?cmd=Retrieve&db=PubMed&list-uids=1846738&dont=AbstractPlus; printed on May 9, 2007.

Howarth, Peter H.; Persson, Carl G.A.; Meitzer, Eli O.; Jacobson, Mikila R.; Durham, Stephen R.; Silkoff, Philip E.; Objective Monitoring of Nasal Airway Inflammation in Rhinitis; Journal of Allergy Clin Immunol; Mar. 2005; pp. S414-S441; American Academy of Ailergy, Asthma and Immunology.

Hsieh, Dean S. T.; Langer Robert; Folkman, Judah; Magnetic Modulation of Release of Macromolecules from Polymers; Proc. Natl. Acad. Sci. USA; bearing a date of Mar. 1981; pp. 1863-•J 867; vol. 78. No. 3.

Hsu, Kai-Hsiung; Durand, Dominique M., Prediction of Neural Excitation During Magnetic Stimulation Using Passive Cable Models; IEEE Transactions on Biomedical Engineering; Apr. 2000; pp. 463-471; vol. 47, No. 4; IEEE.

Hsu, Kai-Hsiung; Durand, Dominique M.; A 3-D Differential Coil Design for Localized Magnetic Stimulation; IEEE Transactions on Biomedical Engineering; Oct. 2001; pp. 1162-1168; vol. 48, No. 1 O; IEEE.

Hsu, Kai-Hsiung; Nagarajan, Srikantan S.; Durand, Dominique M.; Analysis of Efficiency of Magnetic Stimulation; IEEE Transactions on Biomedical Engineering; Nov. 2003; pp. 1276-1285; vol. 50, No. 11; IEEE.

Kane, D.; Lockhart, JC; Balint, PV; Mann, C.; Ferrell, WR; Mcinnes, 18; Protective Effect of Sensory • enervation in Inflammatory Arthritis (evidence of regulatory neuroimmune pathways in the

(56) References Cited

OTHER PUBLICATIONS arthritic joint); ARD Online, Ann. Rheum. Dis.; 2005; pp. 325-327 plus cover page; vol. 64; located at: www.annrheumdis.com.

Kilani, Ruhangiz T.; Maksymowych, Walter P.; Aitken, Alastair; Boire, Gilles; St. Pierre, Yves; U, Yunyuan; Ghahary, Aziz; Detection of High Levels of 2 Specific Isoforms of 14-3-3 Proteins in Synovial Fluid from Patients with Joint Inflammation; The Journal of Rheumatology; 2007; pp. 1650-1657; vol. 34, No. 8.

Kilgore, K.L.; Bhadra, N.; Nerve Conduction Block Utilising High-Frequency Alternating Current; Medicai & Biological Engineering & Computing; 2004; pp. 394-406; voi. 42; IFMBE.

Krasteva, Vessela TZ; Papazov, Sava P.; Daskalov, Ivan K.; Peripheral Nerve Magnetic Stimulation: Influence of Tissue Non-Homogeneity; BioMedical Engineering on line; 2003; pp. 1-14; located at: http://www.biomedicalengineering-online.com/content/2/1 /19.

Krauthamer, V.; Crosheck, T.; Effects of High-Rate Eiectrical Stimulation Upon Firing in Modelled and Real Neurons; Medical & Biological Engineering & Computing; 2002; pp. 360-366; vol. 40; IFMBE.

Kuwabara, Satoshi; Cappelen-Smith, Cecilia; Lin, Cindy S.-Y.; Mogyoros, Ilona; Bostock, Hugh; Burke, David; Excitabiiity Properties of Median and Peroneai Motor Axons; Muscle and Nerve; Sep. 2000; pp. 1365-1373; vol. 23.

Lam, FY; Ferrell, WR; Neurogenic Component of Different Models of Acute Inflammation in the Rat Knee Joint.; Published, NCBI, Ann. Rheum. Dis.; Nov. 1991; pp. 747-751, only the abstract is enclosed; vol. 50, No. 11; printed on May 17, 2007.

Lele, P.P ; Effects of Focused Ultrasonic Radiation on Peripheral Nerve, with Observations on Local Heating; Experimental Neurology; 1963; pp. 47-83; vol. 8.

Lin, Cindy S.-Y.; Mogyoros, Ilona; Kuwabara, Satoshi; Cappelensmith, Cecilia; Burke, David; Accommodation to Depolarizing and Hyperpolarizing Currents in Cutaneous Afferents of the Human Median and Sural Nerves; The Journal of Physiology Online; J, Physiol. 2000; pp. 483-492; vol. 529; located at: http://www.jp.physoc.org/cgi/content/full/529/2/483; printed on Oct. 5, 2007.

Local Anaesthetics and Nerve Conduction; The Virtual Anaesthesia Textbook; bearing a date of 2000; pp. 1-2; located at: http://www.virtual-anaesthesia-textbook.corn.

Ma, Qing-Ping; Vanilloid Receptor Homologue, VRU, is Expressed by Both A and C-Fiber Sensory Neurons NeuroReport, Somatosensory Systems, Pain; bearing a date of Dec. 4, 2001; pp. 3693-3695; vol. 12, No. 17; Lippincott Williams & Wil.

Makers of ActiPatch(TM) a Drug-Free, Anti-Inflammatory Patch that Resolves Swelling BioElectronics; 2004; pp. 1-4; BioElectronics Corp.

Marks, William 8.; Loeb, Gerald E.; Action Currents, Internodal Potentials, and Extracellular Records of Myelinated Mammalian Nerve Fibers Derived from Node Potentials; Biophysical Journal; 1976; pp. 655-668; vol. 16.

McCleskey, Edwin W.; Neuroscience: A Local Route to Pain Relief; Nature—News & Views; bearing a date of Oct. 4, 2007; pp. 545-546; vol. 449; Nature Publishing Group.

McNeal, Donald R.; Analysis of a Model for Excitation of Myelinated Nelve; IEEE Transactions on Biomedical Engineering; Jul. 1976; pp. 329-337; vol. BME-23, No. 4.

Norton, Stephen J., Research: Can Ultrasound be Used to Stimulate Nerve Tissue ?; BioMedical Engineering Online; 2003; pp. 1-9; vol. 2, No. 6; Bio Med Central Ltd.; located at: http://www.biomedical-eng ineering-onl ine. com/content/2/1 /6.

Orlee, Kenneth S., Horch, Kenneth VV.; Differential Activiation and Block of Peripheral Nerve Fibers by Magnetic Fields; Muscle and Nerve; 2006; pp. 189-196; vol. 34; located at: www.interscience.wiley.com.

Pareek, Tej K.; Keller, Jason; Kesavapany, Sashl; Pant, Harish C ; Ladarola, Michael J.; Brady, Roscoe O.; Kulkarni, Ashok B.; Cyelin-Dependent Kinase 5 Activity Regulates Pain Signaling; PNAS; bearing a date of Jan. 17, 2006; pp. 791-796; vol. 103, No. 3.

Pavlov, VA; Tracey, K.J.; Review: Neural Regulators of Innate Immune Responses and Inflammation; CMLS-Cellular and Molecular Life Sciences; 2004; pp. 2322-2331; vol. 61; Birkhiiuser Verlaa Basel.

PCT International Search Report; International App. No. PCT/US 08/13442; Feb. 20, 2009; pp. 1-3.

PCT International Search Report; International App. No. PCT/US 08/13443; Feb. 20, 2009; pp. 1-2.

PCT International Search Report; International App. No. PCT/US 08i13407; Feb. 20, 2009; pp. 1-2.

PCT International Search Report; International App. No. PCT/US2008i013406; Feb. 9, 2009; pp. 1-2.

Peckham; P. Hunter; Knutson; Jayme S.; Functional Electrical Stimulation for Neuromuscular Applications; Annual Reviews; 2005; pp. 327-360; located at: http://www.arjournals.annualreviews.org; printed on Feb. 13, 2007.

Pham-Marcou, T.A.; Gentili, 1\/1.; Asehnoune, K.; Fletcher, D.; Mazoit, J.-X.; Pain: Effect of Neurolytic Nerve Block on Systemic Carrageenan-Induced Inflammatory Response in Mice; British Journal of Anaesthesia; 2005; pp. 243-246; vol. 95, No. 2; The Board of Management and Trustees of the British Journal of Anaesthesia.

Poole, AR; Immunochemical Markers of Joint Inflammation; Skeletal Damage and Repair: Where are we now?; Annals of the Rheumatic Diseases; 1994; pp. 3-5; vol. 53.

Power, I., Review Article: Fentanyl HCI Iontophoretic Transdennal System (ITS): Clinical Application of Iontophoretic Technology in the Management of Acute Postoperative Pain; British Journal of Anaesthesia; bearing a date of 2007; pp. 4-11; vol. 98, No. 1.

Prescott, James H.; Lipka, Sara; Baldwin, Samuel; Sheppard, Jr., Norman F.; Maloney, John M.; Coppeta, Jonathan; Yomtov, Barry; Staples, Mark A.; Santini, Jr.; John T.; Brief Communications: Chronic, Programmed Polypeptide Delivery from an Implanted, Muitireservoir Microchip Device; Nature Biotechnology; bearing a date of Apr. 2006; pp. 437-438; vol. 24, No. 4; located at: www.nature.com1naturebiotechnology.

Product Information: Actipatch; BioElectronics, Medical Professionals Info Center; 2004; pp. 1-3; BioElectronics Corp.

Rattay, Frank, Aberham, Matthias; Modeling Axon Membranes from Functional Electrical Stimulation; IEEE Transactions on Biomedical Engineering; Dec. 1993; pp. 1201-1209; vol. 40, No. 12; IEEE.

Rattay, Frank; Analysis of Models for Extracellular Fiber Stimulation; IEEE Transactions on Biomedical Engineering; Jul. 1989; pp. 676-682; vol. 36, No. 7; IEEE.

Rattay; Frank; Modeling the Excitation of Fibers Under Surface Electrodes; IEEE Transactions on Biomedical Engineering; Mar. 1988; pp. 199-202; vol. 35, No. 3; IEEE.

Razavi, Rozita; Chan, Yin; Afifiyan, F. Nikoo; Liu, Xue Jun; Wan, Xiang; Yantha, Jason; Tsui, Hubert; Tang, Lan; Tsai, Sue; Santamaria, Pere; Driver, John P.; Serreze, David; Salter, Michael W.; Dosch, H.-Michael; TRPV1 + Sensory Neurons Control 13 Ceil Stress and Islet Inflammation in Autoimmune Diabetes; Cell; bearing a date of Dec. 15, 2006; pp. 1123-1135; vol. 127; Elsevier inc.

Robot Anaesthetist Developed in France: Doctor; Yahool; Agence France Press; bearing a date of Apr. 12, 2008; pp. 1-2.

Rooney, Terence; Bresnihan, Barry; Andersson, Ulf; Gogarty, Martina; Kraan, Maarten; Schumacher, H. Ralph; Ulfgren, Annkristin; Veale, Douglas J.; Youssef, Peter P.; Tak, Paul P.; Microscopic Measurement of Inflammation in Synovial Tissue: Inter-Observer Agreement for Manual Quantitative, Semiquantitative and Computerised Digital image Analysis; Ann Rheum Dis; 2007; pp. 1656-1660; vol. 66.

Roxhed, Niclas; Samel, Bjorn; Nordquist, Lina; Griss, Patrick; Stemme, Goran; Painless Drug Delivery Through Microneedle-Based Transdermal Patches Featuring Active Infusion; IEEE Transactions on Biomedical Engineering; bearing a date of Mar. 2008; pp. 1063-1071, vol. 55, No. 3.

Saliba, Susan; Mistry, DilaawarJ.; Perrin, David H.; Gieck, Joe; Weitman, Arthur; Original Research: Phonophoresis and the Absorption of Dexamethasone in the Presence of an Occlusive Deressing; Journal of Athletic Training; 2007; pp. 349-354; National Athletic Trainers' Association, Inc; located at: www.journalofathletictraining.com.

(56) References Cited

OTHER PUBLICATIONS

Singer, Emily; A New Way to Treat Obesity; Technology Review; bearing a date of May 15, 2008; pp. 1-3; MIT.
Singer, Emily; Neural Stimulation for Autoimmune Diseases; Technology Review; bearing a date of Jun. 1, 201 O; pp. 1-2; MIT.
Sternberg, Esther M.; Neural Regulation of Innate Immunity: A Coordinated Nonspecific Host Response to Pathogens; NIH Public Access, Author Manuscript—Nat. Rev. Immunol.; Apr. 2006; pp. 318-328 (pp. 1-26); vol. 6, No. 4.
Struijk, Johannes Jan; The Extracellular Potential of a Myelinated Nerve Fiber in an Unbounded Medium and in Nerve Cuff Models; Biophysical Journal; Jun. 1997; pp. 2457-2469; vol. 72; Biophysical Society.
Stubbe, Barbara G.; De Smedt, Stefaan C.; Demeester, Joseph; Review Programmed Polymeric Devices for Pulsed Drug Delivery; Pharmaceutical Research; bearing a date of Oct. 2004; pp. 1732-1740; vol. 21, No. 10.
Study Finds Nerve Damage in Previously Mysterious Chronic Pain Syndrome; Doctor's Guide, Personal Edition; 2007; pp. 1-2 (front and back); located at: http://www.docguide.com/news/content.nsflNewsPrint/852571020057CCF685257107005273F6; printed on May 9, 2007.
Tai, Changfeng; De Groat, William C.; Roppolo, James R.; Simulation Analysis of Conduction Block in Unmyelinated Axons Induced by High-Frequency Biphasic Electrical Currents; IEEE Transactions on Biomedical Engineering; Jul. 2005; pp. 1323-1332; vol. 52, No. 7.
Tokusilige, Natsuko; Markham, Robert; Russell, Peter; Fraser, Ian S ; Nelve Fibers in Peritoneal Endometriosis; Human Reproduction; 2006; pp. 3001-3007; vol. 21, No. 11.
Tracey, Kevin J.; Review: Physiology and Immunology of the Cholinergic Anti-infiammatory Pathway; The Journal of Clinical Investigation; Feb. 2007; pp. 289-296; vol. 117, No. 2; located at: http:i/www.jci.org.
Treatment Blocks Pain Without Disrupting Other Functions; published: Oct. 3, 2007; 2 pages; .. iocatedat:. http://www.physorg.com/news110637008.html.
Tsui, Po-Hsiang; Wang, Shyh-Hau; Huang, Chill-Chung; In Vitro Effects of Ultrasound with Different Energies on the Conduction Properties of Neural Tissue; ScienceDirect-Ultrasonics; 2005; pp. 560-565; vol. 43; Elsevier B.V.; located at: www.elsevier.com/locate/ultras.
UK Intellectual Property Office Examination Report under Section 18(3); Application No. GB1010163.2; Jan. 26, 2012; pp. 1-2.
Van Den Honert, Christopher; Mortimer, J. Thomas; A Technique for Collision Block of Peripheral Nerve: Single Stimulus Analysis; IEEE Transactions on Biomedical Engineering; May 1981; pp. 373-378; vol. BME-28, No. 5.
Voloshin, ilya; Gelinas, Jill; Maloney, Michael D.; O;Keefe, Regis J.; Bigliani, Louis U.; Blaine, Theodore A.; Proinflammatory Cytokines and Metallo proteases are Expressed in the Subacromial Bursa in Patients with Rotator Cuff Disease; The Journal of Arthroscopic and Related Surgery; 2005; pp. 1076e1-1076e9; vol. 21, No. 9.
VVells, Jonathan; Kao, Chris; Konrad, Peter; Milner, Tom; Kim, Jihoon; Mahadevan-Jansen, Anita; Jansen, E. Duco; Application of Infared Light for In Vivo Neural Stimulation; The Journal of Biomedical Optics; Nov./Dec. 2005; pp. 064003-1-064003-12; vol. 10(6).
VVells, Jonathan; Kao, Chris; Konrad, Peter; Milner, Tom; Kim, Jihoon; Mahadevan-Jansen, Anita; Jansen, E. Duco; Biophysical Mechanisms of Transient Optical Stimulation of Peripheral Nerve; Biophysical Journal; Oct. 2007; pp. 2567-2580; vol. 93.

Walsh, Raymond R.; Deal, Stanley E.; Reversible Conduction Block Produced by Lipid-Insoluble Quarternary Ammonium Ions in Cetyltrimethylammonium Bromide-Treated Nerves; Am J Physiol; 1959; pp. 547-550; Only the abstract is being provided; vol. 197; located at: http://http://ajpiegacy. physiology. org.
Wells, Jonathan; Konrad, Peter; Kao, Chris; Jansen, E. Duco; Mahadevan-Jansen, Anita; Pulsed Laser Versus Electrical Energy for Peripheral Nerve Stimulation; Journal of Neuroscience Methods; 2007; pp. 326-337; located at: www.elsevier.com/locate/jneurneth.
Windle, Mary L.; Anesthesia, Topical; E-Medicine from WebMD; Mar. 14, 2007; pp. 1-4; located at: vww.webmd.com.
Zhang, Xu; Roppolo, James R.; De Groat, William C.; Tai, Changfeng; Mechanism of Nerve Conduction Block Induced by High-Frequency Biphasic Electrical Currents; IEEE Transactions on Biomedical Engineering; Dec. 2006; pp. 2445-2454; vol. 53, No. 12.
Zhang, Xu; Roppolo, James R.; De Groat, William C.; Tai, Changfeng; Simulation Analysis of Conduction Block in Myelinated Axons Induced by High-Frequency Biphasic Rectangular Pulses; IEEE Transactions on Biomedical Engineering;Jul. 2006; pp. 1433-1436; vol. 53,No. 7.
European Extended Search Report EP Application No. 19763965.1, Mail Date: Nov. 9, 2021. 9 pages.
Adair R. "A model of the detection of warmth and cold by cutaneous sensors through effects on voltage-gated membrane channels" PNAS, Oct. 12, 1999, vol. 96, No. 21, pp. 11825-11829.
Bazett, H.C. et al. "The temperature in the tissues which accompany temperature sensations" Journal of Physiology, 1930, vol. 69, No. 1, pp. 88-112.
Dussor, G. et al. "TRPM7 and Migraine" Headache, Oct. 2016, vol. 56, No. 9, pp. 1406-1417.
Frey, M. "The Distribution of Afferent Nerves in the Skin" JAMA, 1906, vol. 47, No. 9, 645-648.
Higashi, Y. et al. "Efficacy and Safety Profile of a Topical Methyl Salicylate and Menthol Patch in Adult Patients with Mile to Moderate Muscle Strain: A Randomized, Double-Blind, Parallel-Group, Placebo-Controlled, Multicenter Study" Clinical Therapeutics, 2010, vol. 32, pp. 34-43.
ISA, International Search Report and Written Opinion for International Application No. PCT/US2019/021203. Mail Date: Jun. 11, 2019. 12 pages.
Lloyd, D. et al. "Somatosensory pleasure circuit: from skin to brain and back" Experimental Dermatology, 2015, vol. 24, pp. 321-324.
Morrison, I. et al. "Reduced C-afferent fibre density affects perceived pleasantness and empathy for touch" Brain: A Journal of Neurology, 2011, 11 pages.
Sundstrup, E. et al. "Acute Effect of Topical Menthol on Chronic Pain in Slaughterhouse Workers with Carpal Tunnel Syndrome: Triple-Blind, Randomized Placebo-Controlled Trial" Rehabilitation Research and Practice, vol. 2014, 7 pages.
Topp, R. et al. "The Effect of Either Topical Menthol or a Placebo on Functioning and Knee Pain Among Patients with Knee OA" Research Report, 2013; vol. 36, No. 2, pp. 92-99.
International Search Report and Written Opinion dated Jun. 11, 2019 for International Application No. PCT/US2019/021203, 12 pages.
Oral Argument in re Rose, 220 F.2d 459, 105 USPQ 237 (CCPA 1955), United States Court of Customs and Patent Appeals, 5 pages.
Partial European Search Report issued for EP Application No. 21816941.5, Mailing Date: May 8, 2024, 12 pages.

\* cited by examiner

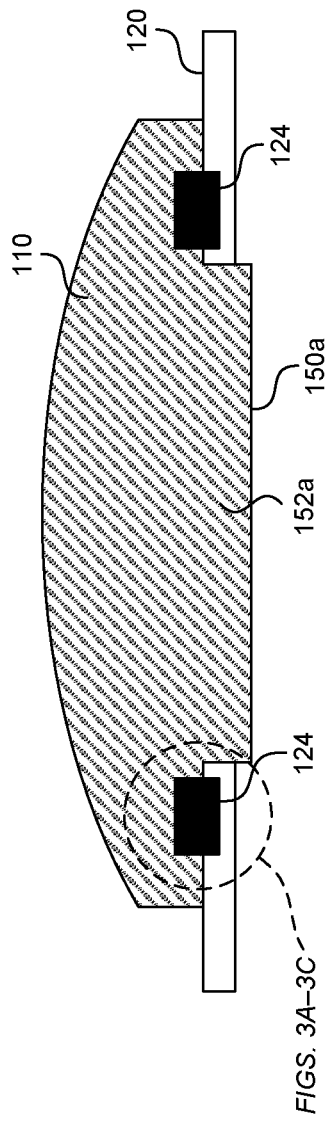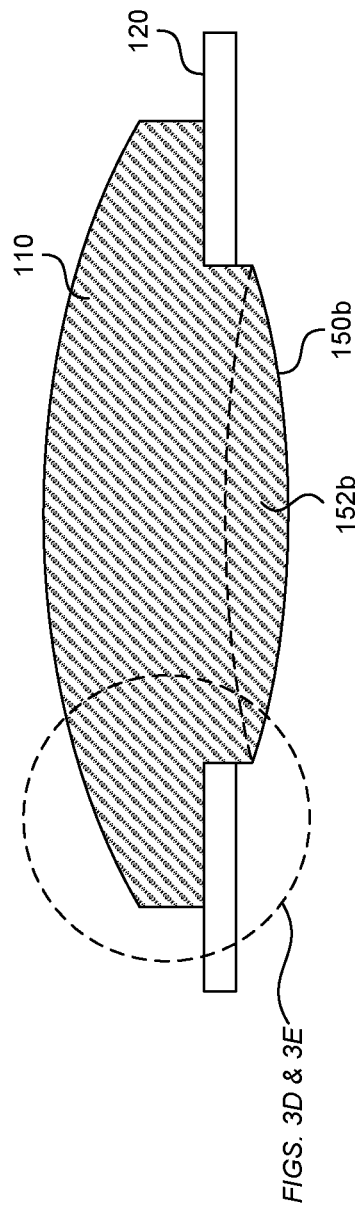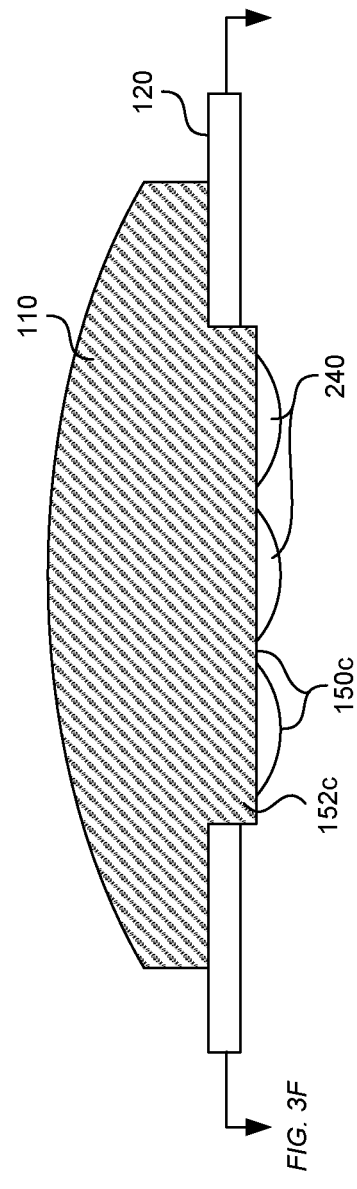

| Sensitive Spots Per Square Centimeter[a] | | | | |
|---|---|---|---|---|
| | Touch[b] | Pain | Cold | Warmth |
| Ball of thumb | 120 | 60 | | |
| Tip of nose | 100 | 44 | 13 | 1.0 |
| Forehead | 50 | 184 | 8 | 0.6 |
| Chest | 29 | 196 | 9 | 0.3 |
| Volar side of forearm | 15 | 203 | 6 | 0.4 |
| Back of hand | 14 | 188 | 7 | 0.5 |

[a] Data from Woodworth RS, Schlosberg H: *Experimental Psychology*. New York, Holt, Rinehart and Winston, 1965.

[b] Arranged in descending touch-spot density.

*FIG. 10*

SYSTEMS AND METHODS FOR IMPROVED PAIN RELIEF FROM STIMULATION OF THERMAL FIBERS

CROSS-REFERENCE TO RELATED APPLICATION(S)

The present application claims priority to U.S. Provisional Patent Application No. 62/639,930, titled "SYSTEMS AND METHODS FOR IMPROVED PAIN RELIEF FROM ACTIVATION OF THERMAL COLD FIBERS," filed Mar. 7, 2018, the disclosure of which is hereby incorporated by reference in its entirety.

TECHNICAL FIELD

The present technology relates generally to stimulus-based therapeutic devices, systems, and methods. In particular, the disclosure relates to systems and methods for applying heat pulses and topical compounds to a patient's body for therapeutic purposes.

BACKGROUND

In 1965, Melzack and Wall described the physiologic mechanisms by which stimulation of large diameter non-pain sensory nerves could reduce the amount of unpleasant activity carried by pain nerves. This landmark observation published in Science was termed the "gate control theory" and offered a model to describe the interactions between various types of the sensory pathways in the peripheral and central nervous systems. The model described how non-painful sensory input such as mild electrical stimulation could reduce or "gate" the amount of nociceptive (painful) input that reached the central nervous system. The gate-control theory stimulated research that lead to the creation of new medical devices and techniques, such as transcutaneous electrical nerve stimulators (TENS). However, TENS and other techniques evolving from the gate control theory have provided sub-optimal pain relief. Accordingly, new techniques for reducing pain are needed.

BRIEF DESCRIPTION OF THE DRAWINGS

FIGS. 2A-2C are side cross-sectional views of the system shown in FIG. 1A illustrating a stimulus pod secured against an anchor in accordance with embodiments of the present technology.

FIG. 10 is a table illustrating the density of mechanical receptors, nociceptors, cold receptors, and warm receptors at various areas of a human body.

DETAILED DESCRIPTION

Figure 1A:
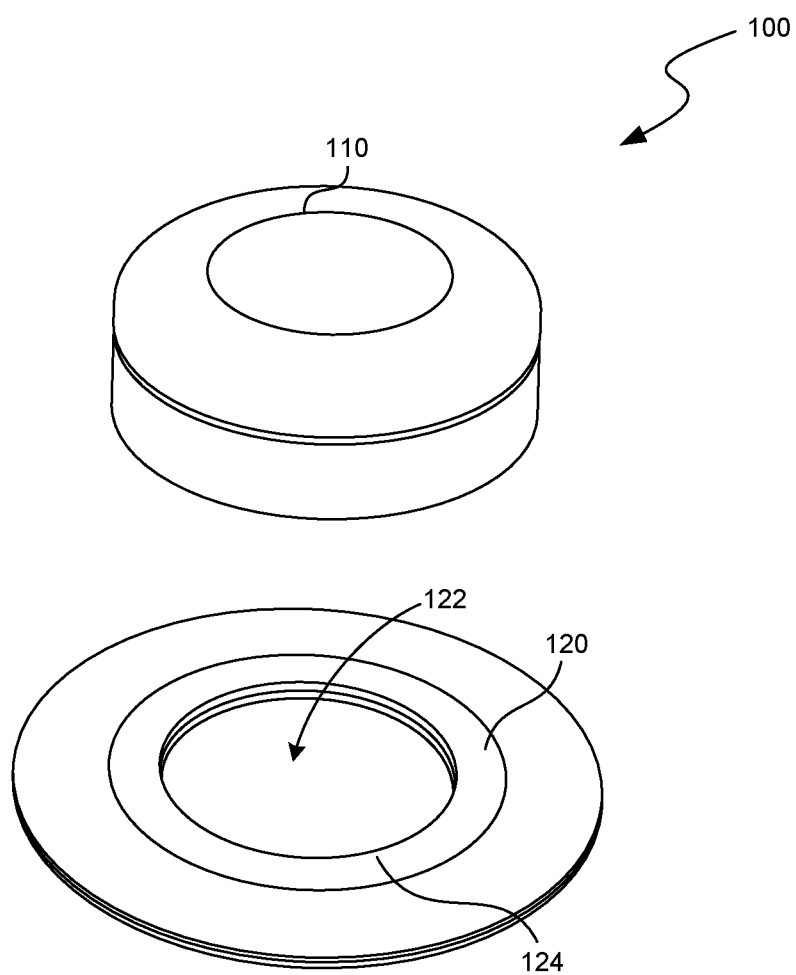
FIG. 1A is a perspective view of a stimulus pod system configured in accordance with an embodiment of the present technology.

The present technology is directed generally to systems, devices, and associated methods for applying stimuli to various parts of the body of a human subject or patient. The stimuli can be configured to activate thermoreceptors in the human subject to alleviate, mask, or otherwise reduce a sensation of pain. The stimuli can be a thermal stimulus, such as heat. The stimuli can also be a composition configured to activate certain thermoreceptors, such as menthol or capsaicin.

Several details describing thermal and electrical principles are not set forth in the following description to avoid unnecessarily obscuring embodiments of the present technology. Moreover, although the following disclosure sets forth several embodiments of the present technology, other embodiments can have different configurations, arrangements, and/or components than those described herein without departing from the spirit or scope of the present technology. For example, other embodiments may have additional elements, or they may lack one or more of the elements described in detail below with reference to FIGS. 1-19.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the claims, but are not described in detail with respect to FIGS. 1-19.

Reference throughout this specification to "one embodiment" or "an embodiment" means that a particular feature, structure or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "substantially", "approximately", and "about" are used herein to mean the stated value plus or minus 10%.

The terms used herein are not intended—and should not be taken—to exclude from the scope of this present technology other types of heat sources that are designed to be placed on the skin to enable pain relief. Illustrative embodiments will be shown and described; however, one skilled in the art will recognize that the illustrative embodiments do not exclude other embodiments.

The headings provided herein are for convenience only and do not interpret the scope or meaning of the claimed present technology.

I. SELECTED EMBODIMENTS OF STIMULUS POD SYSTEMS

FIG. 1A is a perspective view of a stimulus pod system 100 ("system 100") configured in accordance with an embodiment of the present technology. In the illustrated embodiment, the system 100 includes a stimulus pod 110 and an anchor 120. The stimulus pod 110 can be between about 0.5 inch to 2 inches in diameter (e.g., about 1 inch in diameter) and can be equipped to deliver different stimuli to a patient's body, including heat, vibration, and/or electricity. In some embodiments, the stimulus pod 110 can include sensors that gather information and relay the information back to a control station. The anchor 120 can have an adhesive surface that can be applied to various locations on the patient's body, an aperture 122, and an attachment ring 124 that can engage the stimulus pod 110 to hold the stimulus pod 110 onto the patient's body. Additionally or alternatively, the stimulus pod 110 can be kept in place by clothing, magnets, a Velcro-type applicator, elastic bands, pocket-like holders, braces, or other type of applicators capable of holding the stimulus pod 110 against the patient's skin.

Figure 1B:
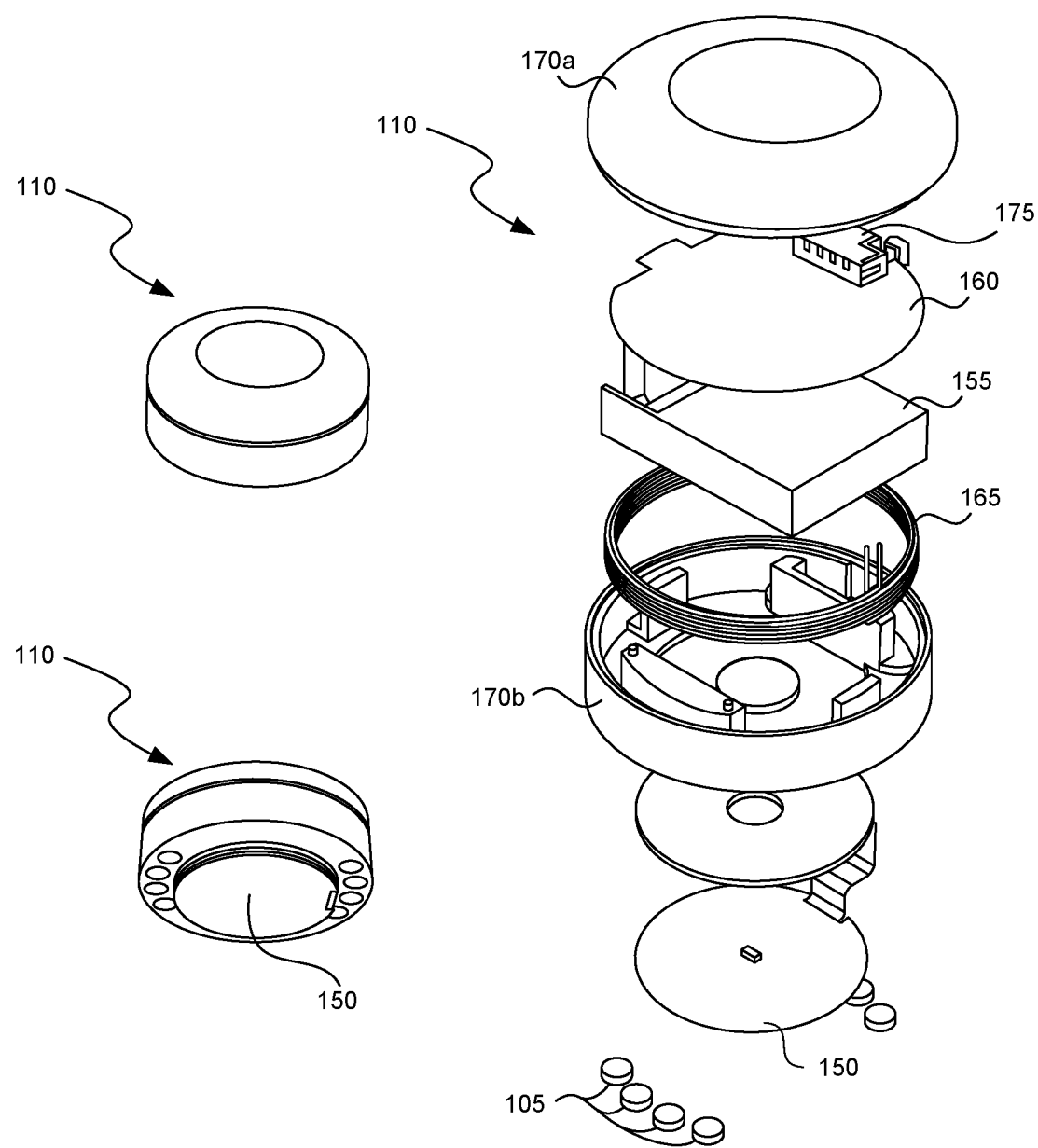
FIG. 1B is an exploded view of a stimulus pod of the system shown in FIG. 1A configured in accordance with an embodiment of the present technology.

FIG. 1B is an exploded view of the pod 110 shown in FIG. 1A configured in accordance with an embodiment of the present technology. In the illustrated embodiment, the stimulus pod 110 includes a stimulus surface 150 that contacts the patient's skin to deliver heat, mild electrical stimuli, vibration, and/or other stimuli to the patient's body in a measured, deliberate pattern to relieve pain and discomfort in the patient's body. The stimulus surface 150 may be about 3 square inches or less. In some embodiments, the stimulus surface may be configured to transfer heat to the skin, and the stimulus surface material may be selected based on a desired thermal conductivity. For example, the stimulus surface may include a conductive heating element, a convective heating element, or a radiation-heating element. In another example, the heating surface may be an electrically resistive heating element with a low thermal mass to facilitate fast thermal rise on activation and fast thermal decay upon deactivation.

In the illustrated embodiment, the stimulus pod 110 includes a battery 155, a circuit board 160, a charging coil 165, and several housing elements 170 (individually referred to as an upper cover 170a and a body 170b). The battery 155 can power the stimulus surface and the circuit board 160. The battery 155 can be a lithium polymer battery or another suitable battery type. The charging coil 165 can be configured to receive power from a power source (e.g., a charging station) and deliver the power to the battery 155. In some embodiments, the stimulus pod 110 can include a wireless communication link 175 through which the stimulus pod 110 receives instructions and/or sends data to and from a control station. In some embodiments, the control station can be a mobile application contained on a cell phone. The housing elements 170 can enclose the internal components of the stimulus pod 110 and provide a convenient handling surface.

In some embodiments, as described in greater detail below with reference to FIGS. 3A-3F, the stimulus pod 110 can include attachment means to attach the stimulus pod 110 to the anchor 120. Referring to FIGS. 1A and 1B, for example, the stimulus pod 110 can have metal slugs 105 that can be magnetized and coupled to the attachment ring 124 (e.g., a metallic ring) in the anchor 120 to hold the stimulus pod 110 to the anchor 120. In some embodiments, the metal slugs 105 can also be used for stimulus delivery. In some embodiments, the metal slugs 105 can be positioned on a top side of the stimulus pods 110 and can be used to interface with a charging station and/or other external device.

In some embodiments, multiple ones of the stimulus pods 110 can be used in concert at different places on the patient's body. In some embodiments, the stimulus pods 110 can also be used to deliver medicine to a patient through electrophoresis, iontophoresis, and/or heat-enhanced perfusion due to capillary dilation. Electrophoresis is the motion of dispersed particles relative to a fluid under the influence of a spatially uniform electric field. Electrophoresis is ultimately caused by the presence of a charged interface between the particle surface and the surrounding fluid. Iontophoresis (a.k.a., Electromotive Drug Administration (EMDA)) is a technique using a small electric charge to deliver a medicine or other chemical through the skin. It is basically an injection without the needle. The technical description of this process is a non-invasive method of propelling high concentrations of a charged substance, normally a medication or bioactive agent, transdermally by repulsive electromotive force using a small electrical charge applied to an iontophoretic chamber containing a similarly charged active agent and its vehicle. One or two chambers are filled with a solution containing an active ingredient and its solvent, also called the vehicle. The positively charged chamber (anode) will repel a positively charged chemical, whereas the negatively charged chamber (cathode) will repel a negatively charged chemical into the skin.

FIG. 10 is an exploded view of the anchor shown in FIG. 1A configured in accordance with an embodiment of the present technology. In the illustrated embodiment, the anchor 120 includes the attachment ring 124, an upper surface 130, an adhesive layer 135, and a liner 140. In some embodiments, the liner 140 can be removed to expose the adhesive layer 135 before placing the anchor 120 on the patient's body. The upper surface 130 is exposed to ambient conditions and accordingly can be similar to a bandage or a wound covering to provide a clean, water-resistant surface for the anchor 120. The attachment ring 124 is positioned beneath the upper surface 130 and can be a metallic ring, such as a steel ring, that can be coupled to the magnetic metal slugs 105 of the stimulus pod 110 and/or other components of the stimulus pod 110. The attachment ring 124 is held to the upper surface 130 by the adhesive layer 135, which can have an adhesive on (i) an upper side thereof to adhere to the attachment ring 124 and the upper surface 130 and (ii) on a lower side thereof to adhere to the liner 140. The lower side of the adhesive layer 135 may optionally include an applicator zone carrying an analgesic. The materials used to form the anchor 120 can all be rigid enough to maintain a proper shape, but flexible enough to substantially conform to the patient's body. For example, the attachment ring 124 can be segmented or thin to permit the anchor 120 to flex to some degree.

Figure 1C:
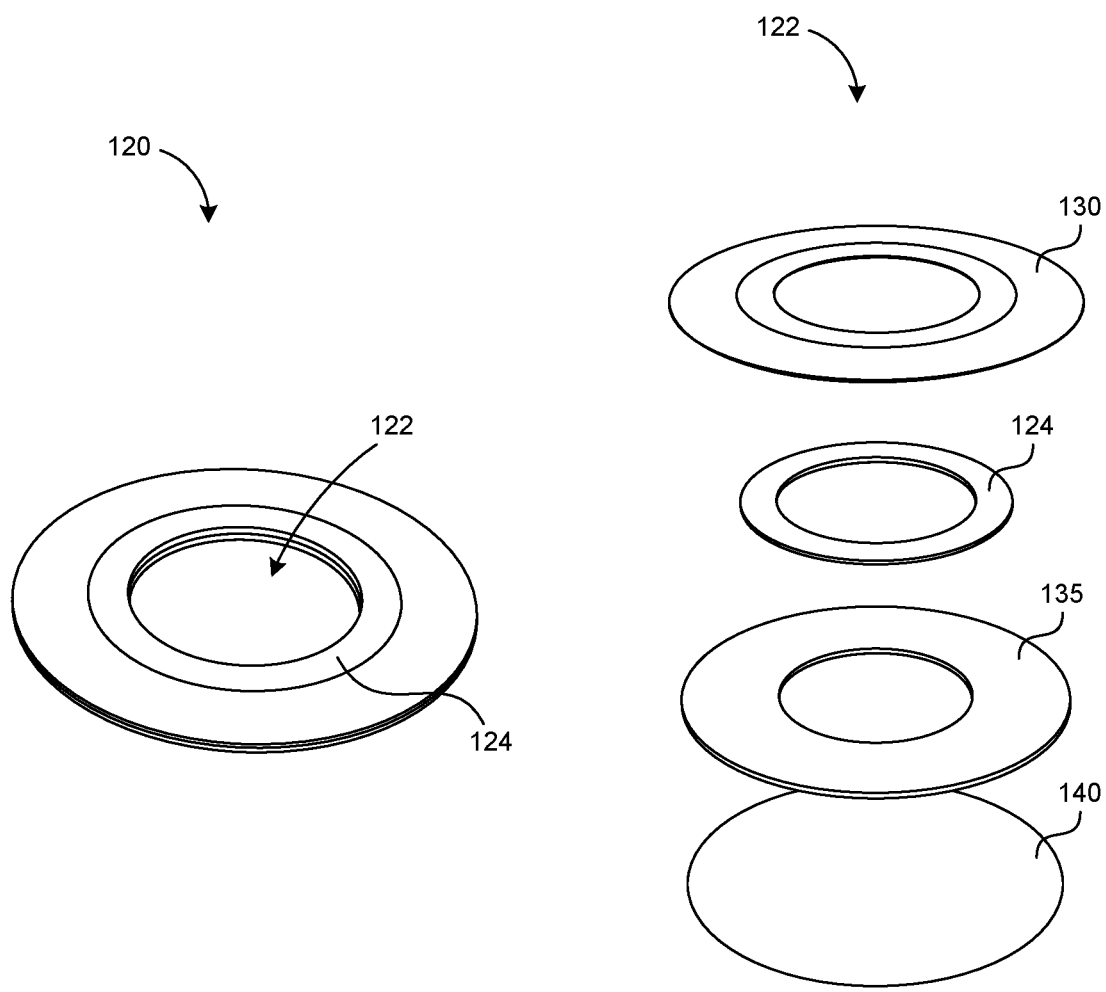
FIG. 1C is an exploded view of an anchor of the system shown in FIG. 1A configured in accordance with an embodiment of the present technology.

Referring to FIGS. 1A-1C together, once the anchor 120 is placed on the body of the patient (e.g., adhered to the body of the patient via the adhesive layer 135), the stimulus pod 110 can be placed into the aperture 122 in the anchor 120 and held in contact with the patient's body to deliver heat and/or other stimulation to the patient. Specifically, in many applications, the stimulus from the stimulus pod 110 can be delivered to the patient's body with the stimulus surface 150 directly contacting the patient's skin. Accordingly, at least a portion of the stimulus pod 110 can project beyond/through the anchor 120 such that the stimulus surface is in direct contact with the patient's skin. FIGS. 2A-2C, for example, are side cross-sectional views of the system 100 with the stimulus pod 110 secured against the anchor 120 and having various stimulus surfaces 150 (individually labeled as stimulus surfaces 150a-150c) in accordance with embodiments of the present technology.

Referring to FIG. 2A, in some embodiments the stimulus pod 110 can have a plug 152a that extends slightly beyond (e.g., projects past a lower surface of) the anchor 120. In the illustrated embodiment, the plug 152a has a stimulus surface 150a with a flat (e.g., generally planar) profile. The attachment ring 124 can engage the stimulus pod 110 with sufficient force such that the stimulus surface 150a presses down onto the patient's skin to ensure sufficient contact with the skin.

Referring to FIG. 2B, in some embodiments the stimulus pod 110 can have a plug 152b with a convex stimulus surface 150b that extends beyond the anchor 120. The slope of the convex stimulus surface 150b can depend in part on the size of the stimulus pod 110 and its intended application. For example, the slope can be selected such that substantially the entire stimulus surface 150b contacts the patient's skin (e.g., such that the slope of the stimulus surface 150b is not too extreme). Accordingly, the convex stimulus surface 150b can have relatively more surface area than the flat stimulus surface 150a shown in FIG. 2A. Therefore, in some embodiments the stimulus surface 150b can contact a relatively greater area of the skin of the patient than the flat stimulus surface 150a.

Referring to FIG. 2C, in some embodiments the stimulus pod 110 can have a plug 152c that extends beyond the anchor 120 and that has a stimulus surface 150c with several small bumps or projections 240. The dimensions of the stimulus surface 150c and the projections 240 can be selected to increase the surface area of the stimulus surface 150c that contacts the patient's skin without creating void spaces or air pockets between the projections 240 that might reduce effective heat transfer or delivery of other stimuli or drugs. In some embodiments, the projections 240 are not discrete, but are continuous and/or sinusoidal.

Figure 3A:
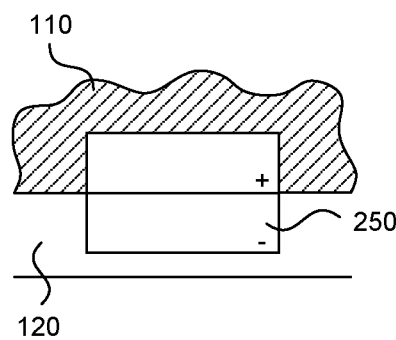
FIGS. 3A-3C are enlarged side-cross sectional views of a portion of the system shown in FIG. 2A and illustrating various attachment mechanisms for attaching the stimulus pod to the anchor in accordance with embodiments of the present technology.

The stimulus pod 110 can be attached to (e.g., secured against, retained by, etc.) the anchor 120 such that the stimulus surface 150 is secured against the patient's skin. FIGS. 3A-3F, for example, illustrate various attachment mechanisms for attaching the stimulus pod 110 to the anchor 120 in accordance with embodiments of the present technology. More specifically, FIGS. 3A-3O are enlarged side-cross sectional views of a portion of the system 100 shown in FIG. 2A, FIGS. 3D and 3E are enlarged side-cross sectional views of a portion of the system 100 shown in FIG. 2B, and FIG. 3F is a bottom cross-sectional view of the system 100 shown in FIG. 2C taken along the line shown in FIG. 2C.

Referring to FIG. 3A, in some embodiments the anchor 120 can include a metallic or magnetic ring 250 that corresponds to a magnet 185 in the stimulus pod 110. The magnetic force between the ring 250 and the magnet 185 can hold/secure the stimulus pod 110 in place relative to the anchor 120.

Figure 3B:
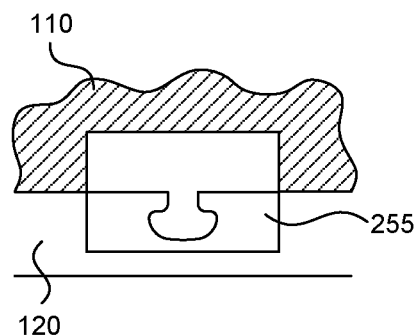

Referring to FIG. 3B, in some embodiments the anchor 120 can be held/secured to the stimulus pod 110 by a mechanical fastener 255 such as a snap, or other similar mechanical attachment means. In the illustrated embodiment, the anchor 120 includes a resilient recession and the stimulus pod 110 includes a matching, resilient projection that, when pressed together, mechanically hold the stimulus pod 110 in place on the anchor 120b. In other embodiments, the anchor 120 can include a projection and the stimulus pod 110 can include a mating recession. In some embodiments, the attachment mechanism at the interface between the anchor 120 and the stimulus pod 110 can operate along the same principle as a plastic cap on a cardboard cup, such as a coffee cup and lid.

Figure 3C:
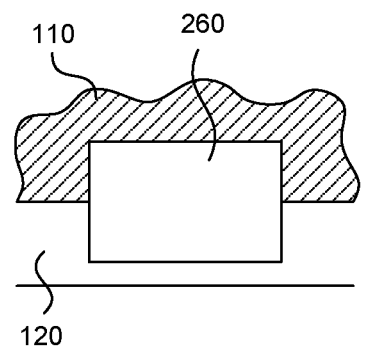
Figure 3D:
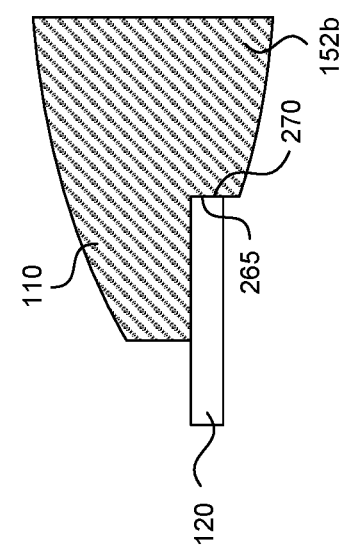
FIGS. 3D and 3E are enlarged side-cross sectional views of a portion of the system shown in FIG. 2B and illustrating various attachment mechanisms for attaching the stimulus pod to the anchor in accordance with embodiments of the present technology.
Figure 3E:
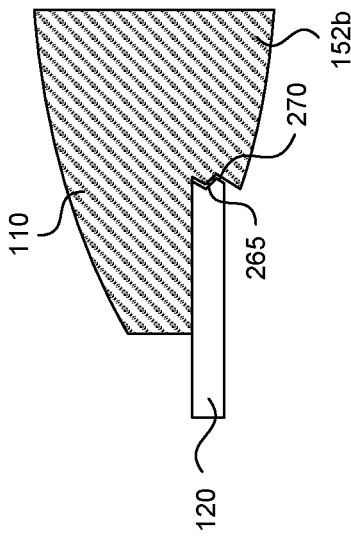
Figure 3F:
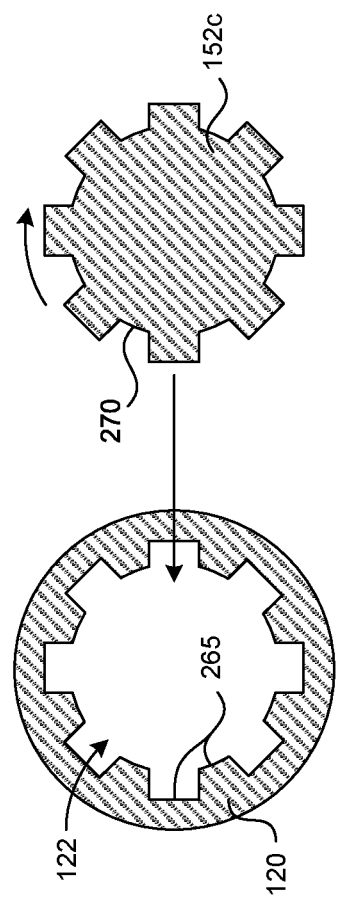
FIG. 3F is a bottom cross-sectional view of the system shown in FIG. 2C and illustrating an attachment mechanism for attaching the stimulus pod to the anchor in accordance with an embodiment of the present technology.

Referring to FIG. 3C, in some embodiments the anchor 120 can be held/secured to the stimulus pod 110 by a hook-and-loop fastener 260.

Referring to FIG. 3D, in some embodiments the anchor 120 can include an interior surface 265 that engages an exterior surface 270 of the plug 152b of the stimulus pod 110 to secure the stimulus pod 110 to the anchor 120. More particularly, one or both of the surfaces 265, 270 can be formed of a resilient material such that, when the plug 152b is pressed into the aperture 122 in the anchor 120, the plug 152b snaps into place.

Referring to FIG. 3E, in some embodiments the surfaces 265, 270 can have corresponding/mating threads such that the stimulus pod 110 can be screwed into the anchor 120.

Referring to FIG. 3F, in some embodiments the interior surface 265 of the anchor can have a keyed, regular, irregular, or other pattern, and the exterior surface 270 of the stimulus pod 110 can include a corresponding/matching pattern configured to engage with the anchor 120 to hold the stimulus pod 110 in place.

Any of the attachment mechanisms illustrated in FIGS. 3A-3F provide a simple way for the patient to apply a stimulus pod 110 to their body. As one of ordinary skill in the art will appreciate, the various configurations of the anchor 120 and stimulus pod 110 shown in FIGS. 2A-3F can be combined and/or integrated together (e.g., to include a magnetic and friction-fit connection).

During operation of the system 100, multiple ones of the stimulus pods 110 can be interchanged between different ones of the anchors 120, and vice versa. A patient can use a stimulus pod 110 until the battery is depleted, and then simply swap in another stimulus pod 110 with a fresh battery. The attachment means can be strong enough and the dimensions of the stimulus pod 110 can be small enough that the stimulus pod 110 can be worn under the patient's clothing easily. The placement of the anchors 120 can vary greatly according to a predetermined diagnostic pattern or personal preference. In some embodiments, one or more of the stimulus pods 110 can be placed at an area of discomfort, such as a painful lower back. Some research suggests that placing additional stimulus pods 110 at an area remote from a problem area can also provide analgesic effects. For example, a patient may place one of the stimulus pods 110 at the lower back—where their pain is—but they can also use a second one of the stimulus pods 110 near the shoulders or on the legs. Multiple stimulus pods 110 can be used in concert to produce an aggregate affect. Because different areas of the human body have different nerve densities, in certain areas two of the stimulus pods 110 placed near one another can be perceived as a single, large stimulus pod. For example, the patient's back has much lower nerve density than the face, neck, or arms. Accordingly, the patient can use a pair of small stimulus pods 110 (e.g., one or two inches in diameter) at the lower back and spaced about three or four inches apart to achieve the same sensory result as a larger stimulus pod covering the entire area. An unexpected benefit of this arrangement is that much less power is required to provide the stimulus in two small areas than would be required to stimulate the entire area.

Figure 4:
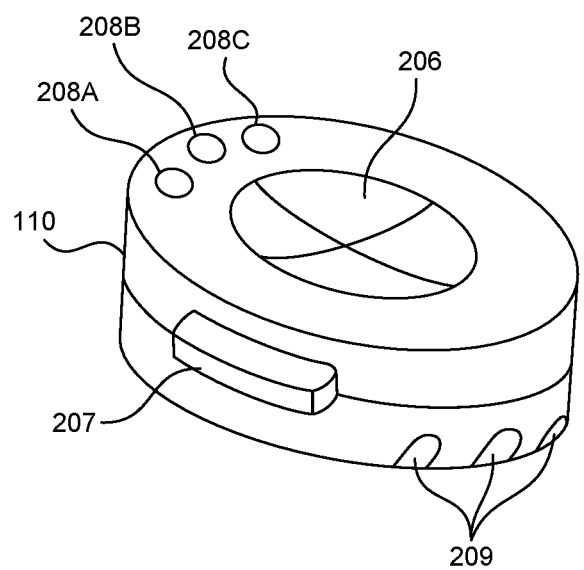
FIG. 4 is a perspective view of a stimulus pod configured in accordance with an embodiment of the present technology.

FIG. 4 is a perspective view of the stimulus pod 110 and showing additional features of the stimulus pod 110 in accordance with embodiments of the present technology. In the illustrated embodiment, the stimulus pod 110 has contacts 209 for interfacing with a charging station and that are positioned on a lower surface of the stimulus pod 110. In other embodiments, the contacts 209 can be positioned on an upper surface of the stimulus pod 110 or elsewhere on the stimulus pod 110. In the illustrated embodiment, the stimulus pod 110 further includes an on/off switch 207 for powering/de-powering the stimulus pod 110. Although a simple push-type on/off switch is illustrated, in other embodiments, the stimulus pod 110 can include other types of switches including, for example, a slide switch, an optical switch, a touch sensor, an accelerometer to detect tapping, etc. In use, the on/off switch 207 is typically activated after contact with the patient's skin has been established. In addition to its power on/off function, the on/off switch 207 can be configured to control a number of heat cycles and/or a temperature of the stimulus pod 110 (e.g., as described in detail below with reference to FIGS. 14-19).

In the illustrated embodiment, the stimulus pod 110 also includes a stimulus cycle switch 206 configured to, for example, switch between different levels of an applied stimulus (e.g., a low, medium, or high temperature). The stimulus pod 110 can also include indicators 208A-C such as LEDs that can light up in response to a particular setting of the stimulus cycle switch 206. In other embodiments, a single indicator 208 capable of changing its color, intensity, or other property can be used to indicate different settings of the stimulus pod 110. A push-type stimulus cycle switch 206 is illustrated in FIG. 4, however, in other embodiments other types of switches can be used such as, for example, a slide switch, multi-pole throw switch, touch sensitive switch, etc.

The stimulus pod 110 may also include an electrical circuit and a temperature measuring element configured to monitor the temperature of the skin. The temperature measuring element may be positioned, for example, in the center of the stimulus surface 150. The temperature measuring element may be operatively coupled to the electrical circuit, and the electrical circuit may be communicatively coupled to a monitoring/control device such as a desktop or laptop computer, a smartphone, a tablet, or other device. The electrical circuit may sense, via the temperature measuring element, a temperature of the skin and, based off the sensed temperature and/or other information, determine one or more characteristics of the skin. The electrical circuit may then transmit information about the one or more characteristics to the monitoring/control device, and the monitoring/control device may display the information to a user or health professional. For example, the electrical circuit may determine information about the skin's thermal transfer capacity and/or the skin's blood flow and send this information to the monitoring/control device for display. The electrical circuit may also utilize a look-up table, formula, chart, or other source of information to predict when thermal injury to the skin may occur. When the electrical circuit determines thermal injury may occur, the electrical circuit may instruct the monitoring/control device to provide a warning to the user, and/or may automatically turn the stimulus pod 110 off.

II. SELECTED EMBODIMENTS OF STIMULUS DELIVERY SYSTEMS

Figure 5:
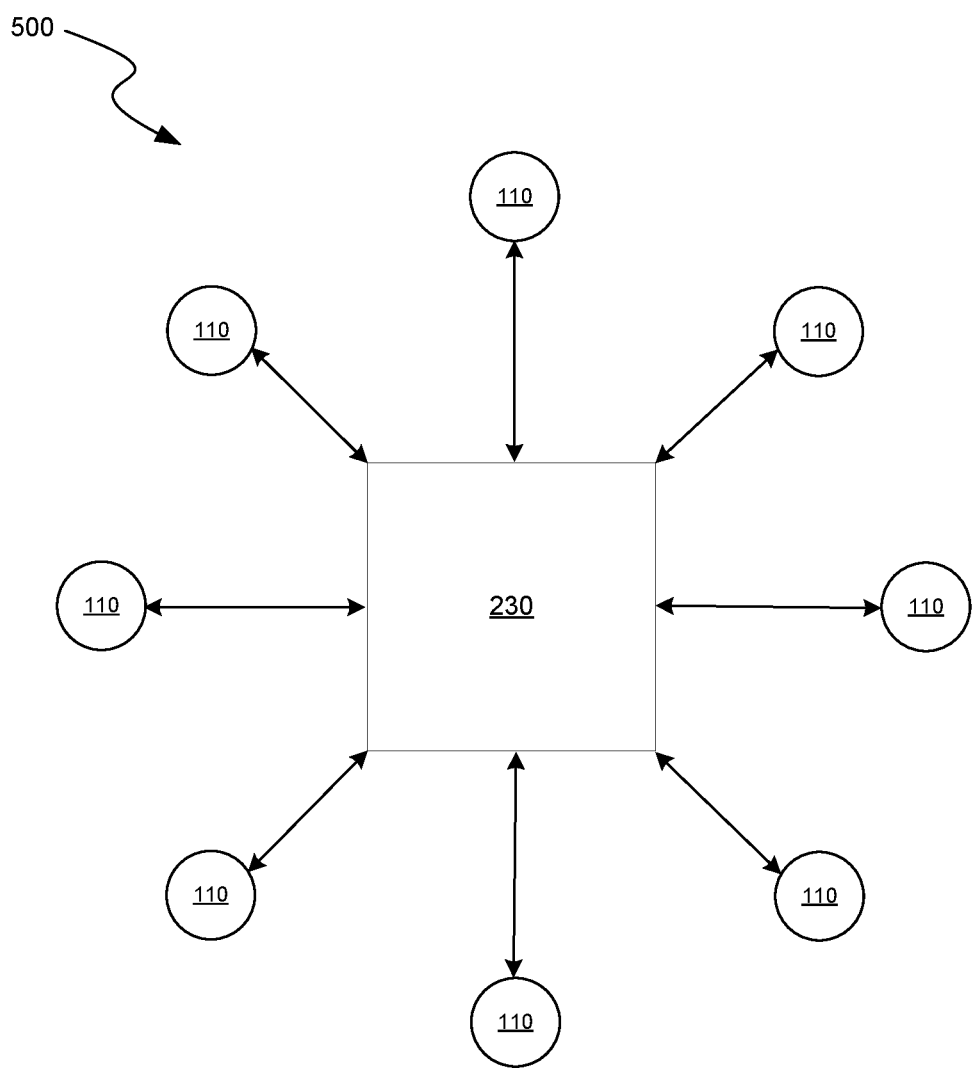
FIG. 5 is a partially schematic view of a stimulus delivery system configured in accordance with an embodiment of the present technology.

In some embodiments, one or more of the stimulus pods 110 can communicate with a control station to, for example, coordinate the delivery of stimulation to a patient at one or multiple locations. FIG. 5, for example, is a partially schematic view of a stimulus delivery system 500 configured in accordance with an embodiment of the present technology. In the illustrated embodiment, the stimulus delivery system 500 includes one or more of the stimulus pods 110 communicatively coupled to a control station 230 (shown schematically in FIG. 5). The stimulus pods 110 can communicate with the control station 230 through any accepted wireless or wired protocol, including radio frequency (RF), infrared light, laser light, visible light, acoustic energy, BLUETOOTH, WIFI, or other communication systems. Additionally, the signals can be sent and received through the patient's skin. In addition to providing a communication path among the stimulus pods 110, sending and receiving signals through the patient's skin may be particularly well suited for determining a distance between the stimulus pods 110.

The control station 230 can be a desktop or laptop computer, a smartphone, a tablet, or other device. In some embodiments, the control station 230 can be included with or integrated into a charging station, and/or can share components such as a power source, circuitry, etc., with a charging station. The control station 230 can instruct one or more of the stimulus pods 110 to apply heat, electric stimuli, vibration, or other stimulus or combination of stimuli in various patterns to the patient's body. In other embodiments, the pods 110 include a button or series of buttons through which the pods 110 can be manually operated. The possible applications are many, and include various combinations of ramp up operations, maximum intensity operations (e.g., maximum temperature or maximum electrical current, etc.), ramp down operations, stimulus soak operations, and lock-out period operations (e.g., as described in detail below with reference to FIGS. 14-19). In some embodiments, stimulus can be applied from different stimulus pods 110 at different levels and/or in different patterns. For example, a patient may place one of the stimulus pods 110 at their upper back, their lower back, and near each of their shoulders or in a different arrangement. The control station 230 can vary the stimulus application at the various zones according to a predetermined pattern. If a smartphone or other device having a screen is used as the control station 230, the screen may display a graphical representation of patient's body with indication as to where to locate the pods 110 in a particular application. Furthermore, the screen may display countdown time information for all or some of the stimulus pods 110, and/or a battery status of the stimulus pods 110.

In several embodiments, the control station 230 can detect or receive information regarding the location of the stimulus pods 110 on the patient's body, and can vary the stimulus pattern accordingly. In one embodiment, the stimulus pods 110 can be built with certain body positions in mind. In some embodiments, the stimulus pods 110 can carry body position labels to instruct the patient to apply the stimulus pods 110 according to the label. For example, in a set of four stimulus pods, two can be marked "shoulders," a third can be marked "lower back," and a fourth can be marked "upper back." In some embodiments, the anchors 120 can communicate their location to the stimulus pod 110. For example, the anchors 120 can include passive identifiers such as RFID tags or other simple, passive devices for communicating with the stimulus pods 110 and/or the control station 230. In such embodiments, the anchors 120 can remain in place even when different stimulus pods 110 are swapped in and out of the anchors 120. Therefore, the stationary anchors 120 can accurately provide location information to the control station 230 independent of which specific ones of the stimulus pods 110 occupy the anchors 120.

In other embodiments, the patient can inform the control station 230 where the stimulus pods 110 are situated, and with this information the control station 230 can apply the desired stimulus pattern to the stimulus pods 110. For example, the stimulus pods 110 can fire sequentially, and the patient can indicate the location of the stimulus on a user interface. Through the user interface, the patient can also operate the system 100 and apply treatment. In some embodiments, the control station 230 can graphically display a depiction of the patient's body, and the patient can indicate to the control station 230 where the stimulus pods 110 are located on their body. Alternatively, the patient can directly control the stimulus application through the stimulus pods 110 by moving a pointing device along the graphical depiction of their body to create a virtual stimulus-massage that the patient, or a healthcare professional, controls directly. In some embodiments, the control station 230 can include a touch screen that the patient can touch to apply heat or other stimulus to various portions of their body (or to the body of another patient).

Figure 6:
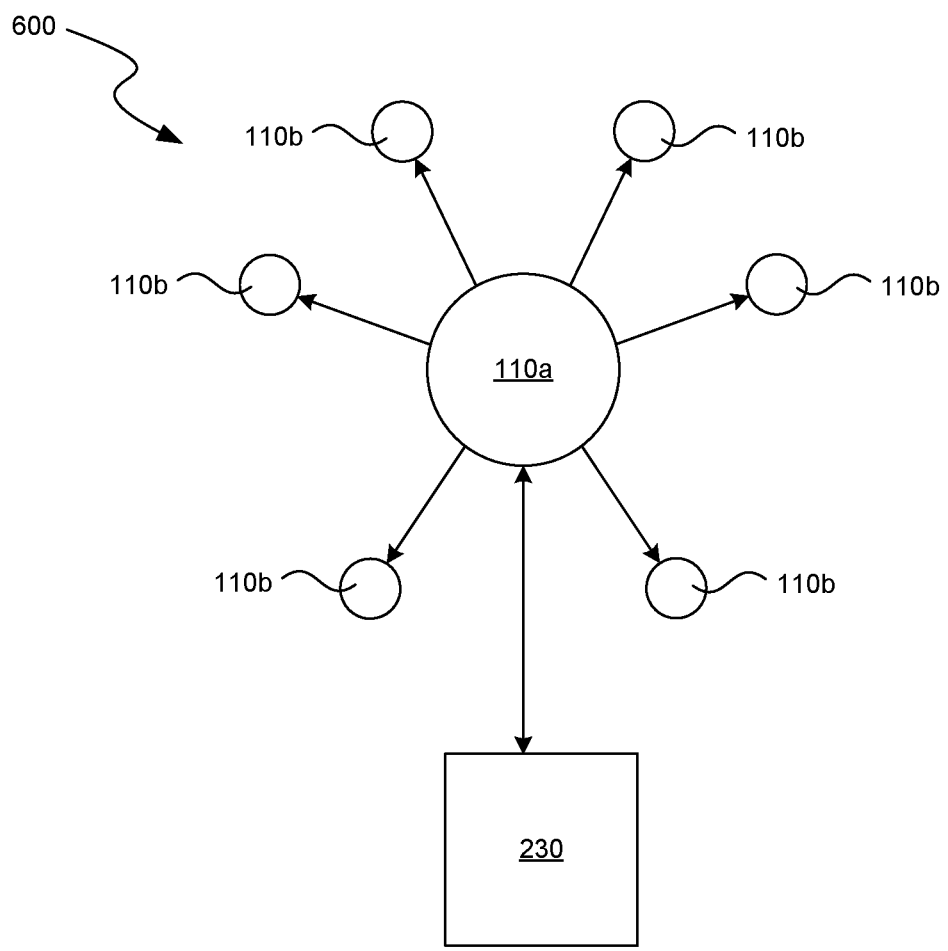
FIG. 6 is a partially schematic view of a stimulus delivery system configured in accordance with another embodiment of the present technology.

FIG. 6 is a partially schematic view of a stimulus delivery system 600 configured in accordance with another embodiment of the present technology. In the illustrated embodiment, the stimulus delivery system 600 includes a plurality of the stimulus pods 110 communicatively coupled to the control station 230 (shown schematically in FIG. 6). At least one of the stimulus pods 110 can be configured as an index pod 110a, and the other ones of the stimulus pods 110 can be configured as dummy pods 110b. In some embodiments, the relationship between the index pod 110a and the dummy pods 110b can be similar to a master/drone relationship. For example, the index pod 110a can include more sophisticated telemetry equipment than the dummy pods 110b, and can act as an intermediary between the dummy pods 110b and the control station 230. The index pod 110a may include stimulus components, such as a heating surface or vibration equipment, and can deliver stimulus just like the dummy pods 110b. Alternately, the index pod 110a can be a dedicated index pod 110a with communication equipment, but without stimulus equipment.

In some embodiments, the index pod 110a and the control station 230 can discern when two or more of the stimulus pods 110 (e.g., dummy pods 110b or index pods 110a) are near enough to one another that they can work in aggregate. If the control station 230 knows where the stimulus pods 110 are placed on the patient's body, the control station 230, through the index pod 110a, can vary the threshold distance between the stimulus pods 110 as a function of nerve density at different locations on the body. For example, if the control station 230 discerns that two or more of the stimulus pods 110 are three inches apart and on the lower back, the control station 230 can operate those ones of the stimulus pods 110 together to effectively cover the area between the stimulus pods 110 as well as the area directly contacting the stimulus pods 110. By comparison, if two or more of the stimulus pods 110 are three inches apart, but are placed on a more sensitive area, such as the patient's face or neck, the control station 230 can determine that the aggregate effect may not be perceived to reach the area between those ones of the stimulus pods 110 because of the greater nerve density. This information can be used when applying a treatment plan that calls for stimulus on a prescribed area. In some embodiments, the control station 230 can determine whether one of the stimulus pods 110 is on or near the prescribed area, and if not, whether the aggregate effect from two or more of the stimulus pods 110 can be used to carry out the treatment plan, and can execute the plan through the stimulus pods 110.

III. SENSATION AND PAIN

Sensory information is carried to the brain via two adjacent spinothalamic tracts: the anterior spinothalamic tract and the lateral spinothalamic tract. The anterior spinothalamic tract conducts information about pressure and crude touch. The lateral spinothalamic tract conducts information about pain and temperature. More specifically, the lateral spinothalamic tract conducts information about pain and temperature via A-Δ, A-β, and C nerve fibers. A-Δ and A-β fibers are myelinated and therefore have fast conduction velocities. C nerve fibers are unmyelinated and therefore have slower conduction velocities. Accordingly, an initial sensation of pain is likely due to transmission of signals via A-Δ and A-β fibers, while lingering sensations of pain are likely due to transmission of signals via C fibers.

Pain signals, transmitted by A-Δ and C nerve fibers, activate awareness in the brain to a potential threat. Pain relief comes when the brain concludes there is no longer a need for the sensation. Pain sensations lasting long after typical healing times (i.e., chronic pain) or for no apparent reason (i.e., idiopathic pain) indicates there may be problems with the immune system, underlying neuropathic disorders, and/or underlying psychological disorders. If the chronic pain is caused by problems with the body's immune system, the pain may be caused by the affected portions of the body being poorly repaired, thereby causing continued firings of the C-fibers transmitting pain sensations. Alternatively, the affected portions of the body may have been re-injured at some point, resulting in continued firings of the C-fibers. If the chronic pain is caused by neuropathic disorders, the pain may be caused by defective nociceptors firing in the absence of inflammatory signals, defective C-fibers transmitting signals without nociceptor activation, a defective dorsal horn continuing to signal the brain without C-fiber signals, or receiving cells in the thalamus being unable to turn down the threat level. If the chronic pain is caused by a psychological disorder, the pain may be the result of other parts of the brain/mind stimulating the thalamus to continue pain sensation production.

IV. THERMORECEPTORS AND PAIN RELIEF

The present technology includes systems and methods for applying a stimulus configured to activate warm and/or cold thermoreceptors of a subject, thus providing pain relief. For example, the stimulus may be heat, and the stimulus delivery systems described herein can be used to apply the heat to a patient. In another example, other heat sources beyond those explicitly described herein may be used to apply the therapeutic stimuli to the patient. In yet another example, the therapeutic stimuli may be a topical compound such as capsaicin or menthol. Applying a stimulus in the form of heat and/or topical compounds can reduce a wide variety of pain and/or treat a variety of ailments. At least a portion of this stimulation-induced pain relief may result from the activation and/or desensitization of warm and/or cold thermoreceptors.

Figure 7A:
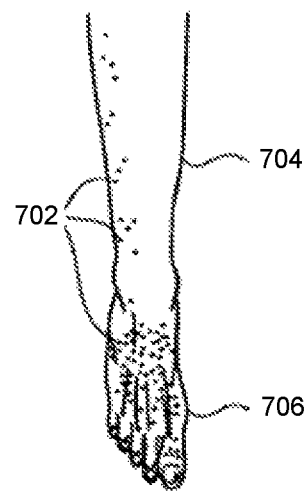
FIG. 7A is an illustration of a mapping of thermoreceptors of a human leg and foot.

To better appreciate the benefits of the present technology, it is helpful to understand the body's reaction to heat. The human body is generally sensitive to heat, with certain body parts having a higher sensitivity than other body parts. The body's sensitivity to heat is recognized by thermoreceptors located in the skin and subcutaneous tissue. FIG. 7A illustrates a mapping of the thermoreceptors 702 of a human leg 704 and foot 706. As shown in FIG. 7A, the receptors 702 have defined receptive fields with little overlap between the fields. The receptors 702 are excited by heat that is applied to the skin. When the receptors 702 become excited from the applied heat, they send signals to stimulate the brain. The brain can accordingly coordinate other bodily functions in response to the signals sent from the receptors 702. For example, the brain can signal to the body to produce endorphins as an analgesic response to the applied heat.

Figure 7B:
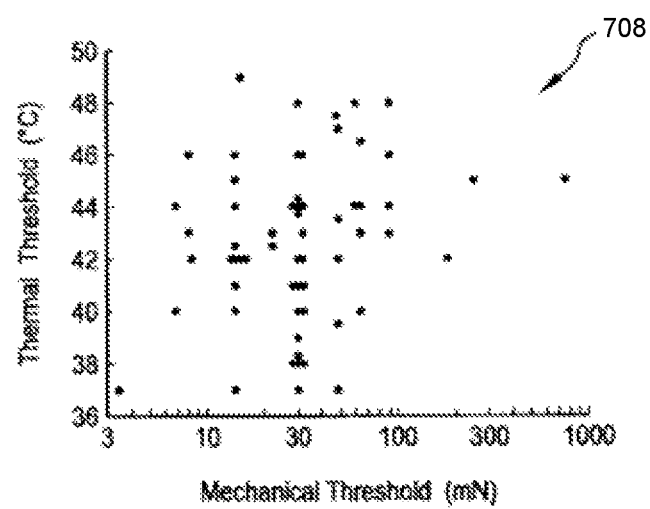
FIG. 7B is a graph of the excitation of thermoreceptors versus applied heat.

The thermoreceptors located throughout the body can be excited or activated at different temperatures. FIG. 7B, for example, is a graph 708 of the excitation of various receptors versus applied heat. The x-axis of FIG. 7B represents mechanical pressure in mN of excited receptors, and the y-axis represents the temperature in degrees C. of the applied heat. As illustrated by the graph 708, the majority of the excitation of the thermoreceptors occurs at temperatures above about 40° C., although some excitation does occur at temperatures below 40° C. The excitation also generally peaks below 50° C.

Figure 8:
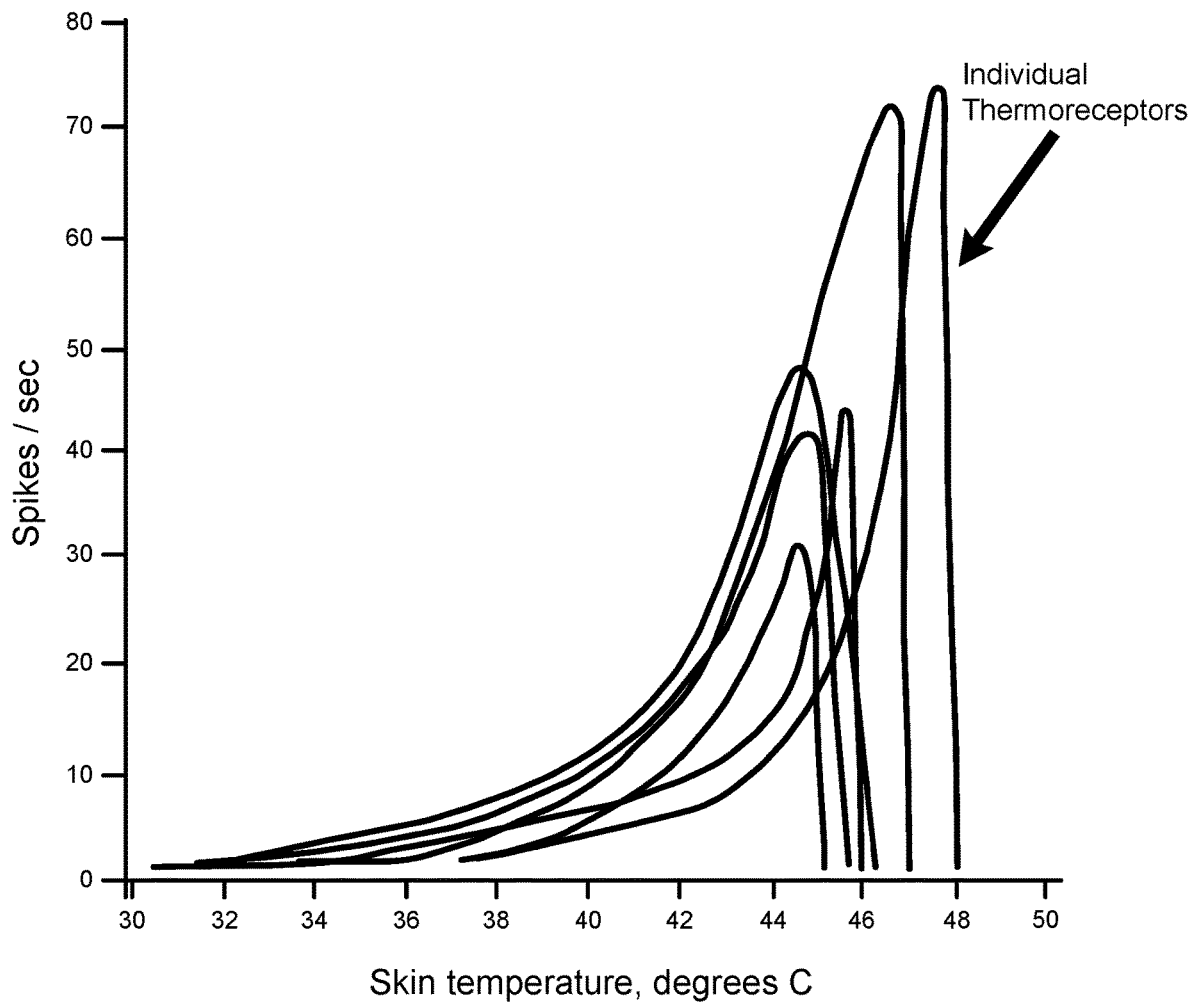
FIG. 8 is a graph of skin temperature versus the spikes per second of thermoreceptors, illustrating the heightened activity of thermoreceptors at increased temperatures.

FIG. 8 further illustrates the increased activation of thermoreceptors at higher temperatures (e.g., about 42° C.). Specifically, FIG. 8 is a graph of skin temperature versus the pulses per second of individual thermoreceptors. As illustrated, thermoreceptors are most active at temperatures between about 42° C. and 48° C., and exhibit peak activity at temperatures between about 45° C. and 48° C.

1. Cold and Warm Thermoreceptors

Thermoreceptors may be divided into at least two categories: cold receptors and warm receptors. Unsurprisingly, cold receptors differ from warm receptors. Warm receptors, for example are stimulated by normothermic temperatures (e.g., about 33-38° C.) and by warm to hot temperatures (e.g., 38° C. or higher). Activation of heat receptors are also affected by the rate of rise of the heat stimuli. As temperatures increase from 40° C. onward, stimulation of warm receptors may produce significant analgesia. However, as temperature continues to increase, warm receptors produce pain, warning the body about potentially harmful burns. The amount of analgesia produced by warm receptors is based on a number of factors, including absolute temperature, rate of temperature rise, duration of heating, and individual variations. Warm receptors utilize myelinated A-Δ fibers and unmyelinated C-fibers and thus exhibit varying conduction times.

Cold receptors are stimulated by cool and cold temperatures (e.g., 33° C. or less), thus providing the sensation of cold and, with extreme low temperatures, a warning about potential tissue damage. Despite also being activated by cold temperatures, certain populations of cold receptors can "awaken" and be stimulated by warm temperatures near the range of uncomfortable heat in a phenomenon described as paradoxical cold. For example, some cold receptors can be activated by temperatures of about 40° C. or higher, about 41° C. or higher, about 42° C. or higher, about 43° C. or higher, about 44° C. or higher, about 45° C. or higher, about 46° C. or higher, about 47° C. or higher, about 48° C. or higher, and/or about 49° C. or higher. This paradoxical stimulation of cold fibers by high-level temperatures may offer the body additional warning and protection from potentially damaging levels of energy.

Figure 9:
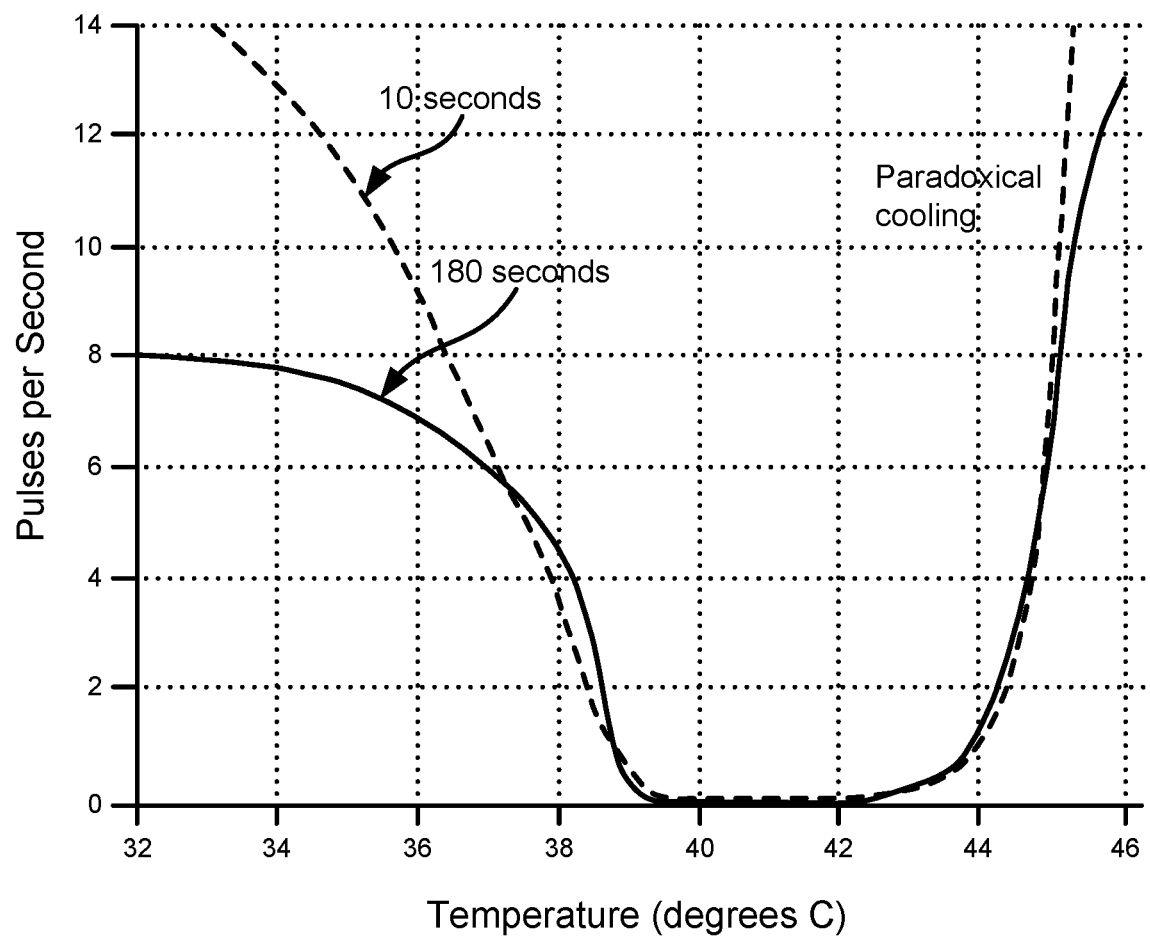
FIG. 9 is a graph of applied temperature versus the average number of pulses per second of cold receptors, illustrating the activity of cold receptors when various temperatures are applied for various durations.

FIG. 9 illustrates the average per second pulse rate of cold receptors at various temperatures. The dashed line marked as "10 seconds" illustrates the average pulses per second of cold receptors following constant thermal stimulation for 10 seconds. The line marked as "180 seconds" illustrates the average pulses per second of cold receptors following constant thermal stimulation for 180 seconds. At cooler temperatures (e.g., below about 37° C.), receptors exposed to cold for 180 seconds have a lower per second pulse average than receptors exposed to cold for 10 seconds. This is likely due to the receptor desensitizing to the thermal stimulus over the duration of exposure. FIG. 9 also illustrates that the receptors are largely silent between about 39-42° C. As the stimulus temperature increase above 42° C., however, the cold receptors are once again activated and produce the sensation of paradoxical cold.

In addition to being activated at different (yet overlapping) temperatures, cold receptors further differ from warm receptors. For example, cold receptors are generally associated with A-Δ fibers that exhibit conduction rates of up to 30 m/sec, which is much faster than warm C fibers' 2 m/sec. The faster conduction of cold sensation may further provide additional protection from potentially damaging levels of energy. In addition, the density of cold receptors is much greater than that of warm receptors. For example, in an exemplary human forearm, there are approximately 7 cold receptors to every 0.24 warm receptors per square centimeter. FIG. 10 further reflects the difference between cold receptor density and warm receptor density at various locations on a human body. In general, cold receptors significantly outnumber warm receptors.

Figure 11:
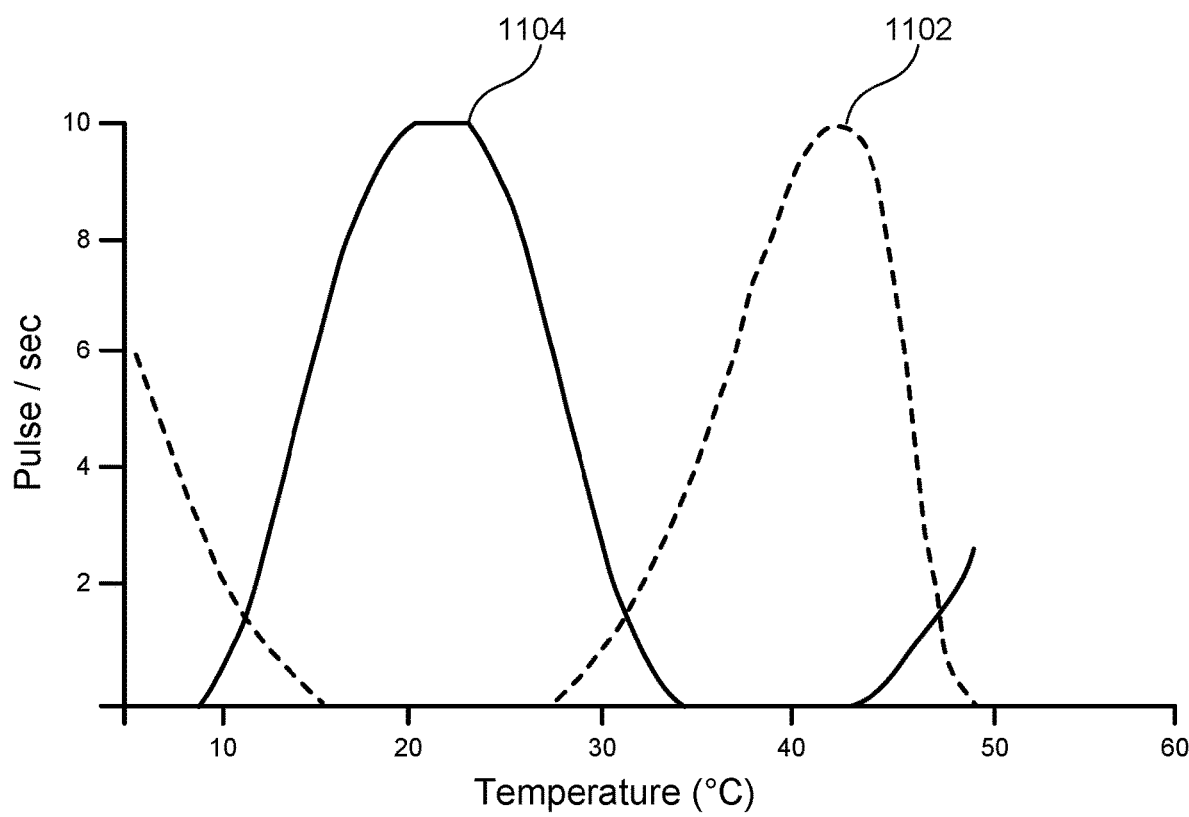
FIG. 11 is a graph of skin temperature versus the pulses per second of cold receptors and warm receptors, illustrating the relative activity of cold and warm receptors at various temperatures.

FIG. 11 is an exemplary graph of the firing rates of warm and cold receptors versus temperature, illustrating the relative activity of each receptor type at various temperatures. Line 1102 illustrates the firing rate of warm receptors (y-axis) versus temperature (x-axis). As illustrated, warm receptors may be activated between temperatures ranging from about 25-50° C. However, peak activation of warm receptors may occur, for example, between about 38-49° C. Line 1104 illustrates the firing rate of cold receptors versus temperature. As one would expect, cold temperatures activate at cooler temperatures than warm receptors (e.g., with peak activation between about 18-30° C.). However, cold receptors are also activated by hot temperatures. For example, the graph illustrates an increase in cold receptor activation as temperature increases from about 42° C. This increase in cold receptor activation at high temperatures may be responsible for the paradoxical cold sensation.

2. Transient Receptor Potential Channels (TRP)

There are different types of cold receptors and warm receptors. The transient receptor potential channel (TRP) superfamily, for example, includes structurally related, non-selective cation channels that serve a variety of functions in the peripheral and central nervous systems, including temperature sensation. In the peripheral nervous system, TRPs respond to a number of different stimuli, including temperature, pressure, inflammatory agents, and receptor activation. In the central nervous system, TRP activity may promote neurite outgrowth, coordinate receptor signaling, and induce excitotoxic cell death resulting from noxious stimuli. Accordingly, the diverse functionality of TRP channels make them an intriguing yet difficult therapeutic target.

The TRP superfamily includes a number of related channels. A functional subset of the channels is distinguished by their sensitivity to temperature. For example, temperature-sensitive TRPs include melastatin receptors (e.g., the menthol receptor TRPM8), vanilloid receptors (e.g., the capsaicin receptor TRPV1 and other heat related receptors TRPV2, TRPV3, and TRPV4), and the chemical, temperature, and mechanical stress sensor ankyrin 1 (TRPA1). In combination, these channels (collectively referred to as thermoTRPs) cover a broad range of temperatures, ranging from noxiously hot to dangerously cold.

Figure 12A:
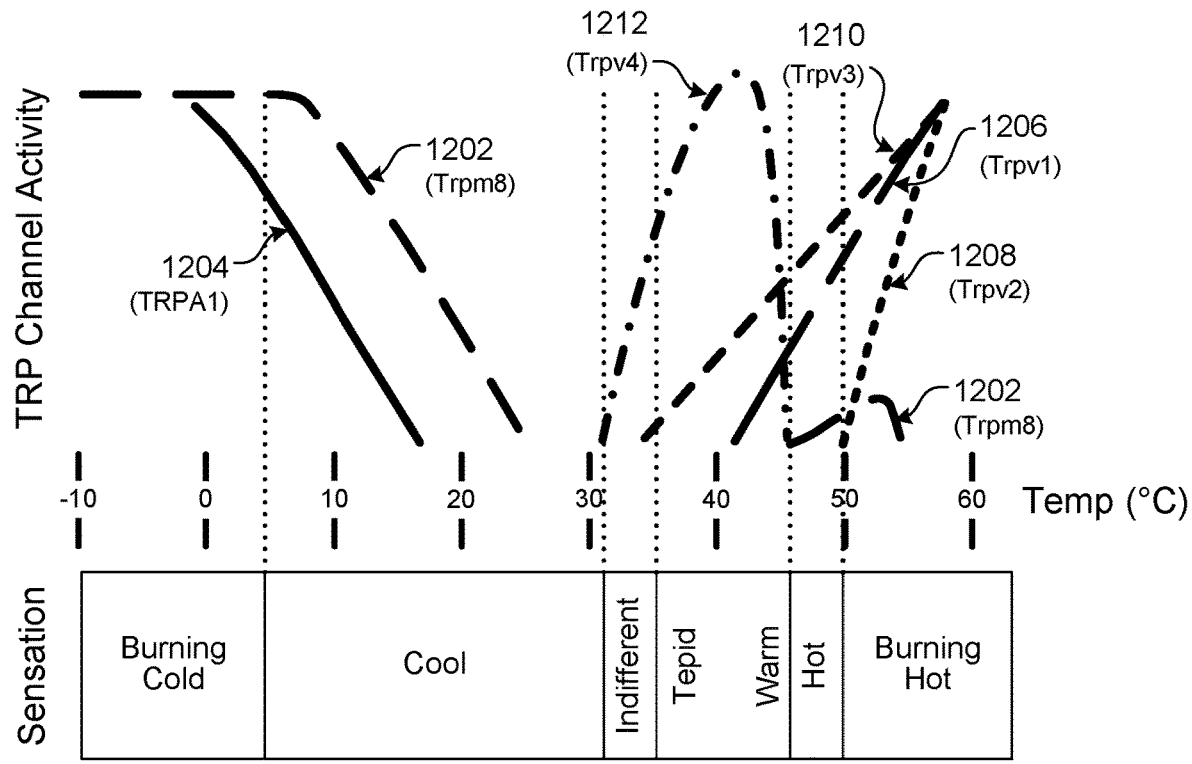
FIG. 12A is a graph of applied heat versus the activity of select TRP channels, illustrating the relative activity of select TRP channels at various temperatures.

FIG. 12A is a graph illustrating the thermally induced activity of thermoTRPs. The y-axis represents TRP channel activity and the x-axis represents temperature. Beneath the x-axis is a description of the associated thermal sensation. As illustrated, various TRPs are active at different temperatures. TRPM8 (line 1202) and/or TRPA1 (line 1204) may be activated by cold and/or cool temperatures (e.g., less than about 30° C., less than about 29° C., less than about 28° C., less than about 27° C., etc.), heat and/or intense heat (e.g., greater than about 40° C., greater than about 41° C., greater than about 42° C., etc.), and certain compounds such as menthol (not shown). TRPM8 and TRPA1 may be prevalent on many areas of the body, including, for example, skin, nerves, muscles, blood vessels, and/or brain tissue. Moreover, TRPM8 and TRPA1 may be implicated in certain types of pain and neurogenic inflammation, including, for example, muscle pain (e.g., strained or pulled muscle), headache, nerve pain, and/or joint pain. The channels may also play a role in idiopathic and chronic pain. Accordingly, and as discussed below in more detail, certain aspects of the present technology include targeting TRPM8 and/or TRPA1 to reduce pain.

The vanilloid receptors, TRPV1 (line 1206), TRPV2 (line 1208), TRPV3 (line 1210), and TRPV4 (line 1212), are all generally activated by warm and/or hot temperatures (e.g., greater than about 30° C., greater than about 35° C., greater than about 40° C., etc.). Similar to TRPM8 and TRPA1, these heat-associated thermoTRPs may be associated with certain types of pain, including, for example, muscle pain (e.g., strained or pulled muscle), headache, nerve pain, joint pain, idiopathic pain, and/or chronic pain. Accordingly, and as discussed below in more detail, certain aspects of the present technology include targeting TRPV1, TRPV2, TRPV3, and/or TRPV4 to reduce pain.

Figure 12B:
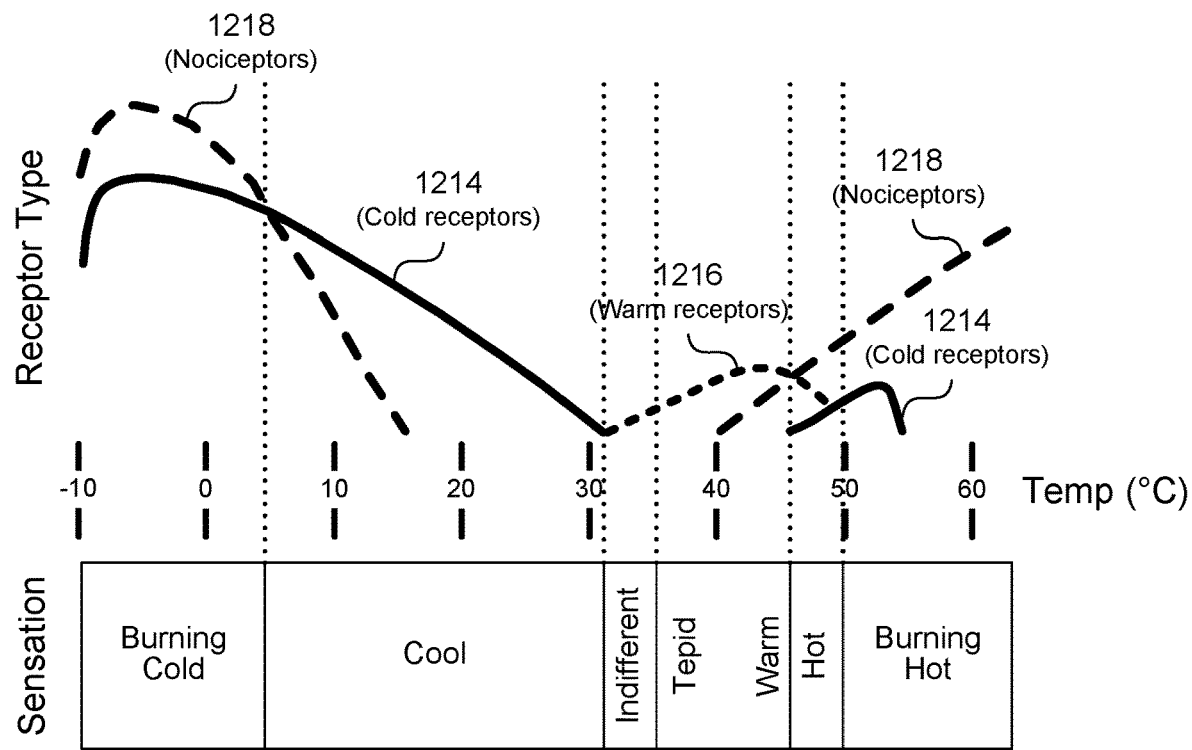
FIG. 12B is a graph of applied heat verses receptor activity, illustrating the relative activity of cold receptors, warm receptors, and nociceptors at various temperatures.

FIG. 12B illustrates the aggregate cold receptor activity illustrated individually in FIG. 12A (e.g., TRPM8 and TRPA1), the aggregate warm receptor activity illustrated individually in FIG. 12A (e.g., TRPV1, TRPV2, TRPV3, and TRPV4), and nociceptor activity at various temperatures. Beneath the x-axis of FIG. 12B is a description of the associated thermal sensation. Cold receptors, represented by line 1214, are active at temperatures of about 30° C. or lower. Cold receptors are also active at temperatures of about 45° C. or higher (paradoxical cold). In some embodiments, cold receptors may also be active at temperatures between about 40-45° C. (not shown). Warm receptors, represented by line 1216, are active at temperatures of about 30° C. or greater. Nociceptors, represented by line 1218, are active at extreme temperatures: about 16° C. or less and about 40° C. or higher. Nociceptor activation is associated with painful sensation, thus providing a warning that tissue damage may occur following prolonged exposure to the temperature.

To better understand certain embodiments of the present technology, it may be helpful to further understand the interplay between certain thermoreceptors. In particular, TRPV1 and TRPM8 may play an important role in thermally mediated pain reduction and will therefore be discussed in further detail herein.

A. TRPV1

TRPV1 is a protein that is expressed in sensory neurons and plays a role in both thermal sensation and nociception. TRPV1 was first identified by its responsiveness to capsaicin, a vanilloid derived from chili peppers that elicits a burning sensation. TRPV1 also responds to noxious heat, with an activation threshold of approximately 43° C. and a temperature coefficient of $Q_{10}>20$. TRPV1 may also be activated by extracellular acidification, indicating it may act as a polymodal nociceptor integrating multiple forms of noxious stimuli. TRPV1 also responds to other pungent chemicals and endogenous lipid-derived molecules, many of which act cooperatively to stimulate channel activity. For instance, capsaicin and acidification both can lower the heat activation threshold for channel activation. TRPV1 is expressed in approximately 30-50% of all somatosensory neurons in rodent models, predominantly peptidergic C-fiber nociceptors. Knockout studies have confirmed that TRPV1 plays a role in nociception. For example, TRPV1 knockout mice and isolated DRG cells of TRPV1 knockout mice demonstrate significant impairments in the detection of noxious heat and protons along with complete loss of capsaicin sensitivity, indicating TRPV1 plays an important role in detection of heat in addition to nociception.

In certain conditions, TRPV1 may become sensitized and/or overactive. The sensitization and overactivity of TRPV1 can be associated with many different forms of pain. Sensitization of TRPV1 may occur via coupling with second messenger signaling cascades by a variety of proalgesic and proinflammatory agents, including nerve growth factor (NGF), bradykinin, lipids, prostaglandins, and ATP. Furthermore, TRPV1 activity contributes to neurogenic inflammation in which nociceptors themselves release inflammatory mediators, thus acting autonomously to promote inflammation and hyperalgesia. TRPV1 may also be required for development of inflammatory thermal hyperalgesia, demonstrating an essential role for TRPV1 in pain hypersensitivity associated with chronic pain conditions. In sum, TRPV1, and in particular TRPV1 hyperactivity, can be integrally involved in many different chronic pain conditions.

TRPV1 activity is associated with numerous types of inflammation and inflammatory-related pain. For example, an increase in the number of TRPV1 immunoreactive fibers in inflamed skin correlates with inflammatory hyperalgesia. Furthermore, TRPV1 antagonists may inhibit thermal and/or mechanical hypersensitivity associated with multiple models of inflammation, including UVB-evoked pain and sensitization, complete Freund's adjuvant (CFA)-induced pain, post-operative pain, and/or cancer pain. Moreover, nocifensive behavior may be significantly reduced in TRPV1 knockout animals or via treatment with TRPV1 antagonists. TRPV1 was also found to mediate pain induced by the activation of the inflammatory mediator protease-activated receptor-2 ($PAR_2$). Thermal hyperalgesia associated with ischemic pain may also be dependent on TRPV1.

TRPV1 may also be functionally significant in neuropathic pain conditions. For example, TRPV1 expression may increase following nerve injury, while blockade of TRPV1 function may reduce both thermal and/or mechanical hypersensitivity. Chemotherapeutics such as oxaliplatin or paclitaxel can increase TRPV1 sensitivity, suggesting an instructive role in chemotherapy-induced peripheral neuropathy. Desensitization of TRPV1 may provide relief from osteoarthritis, postoperative pain, and nerve injury-induced heat sensitivity, further supporting an involvement of TRPV1 in both in inflammatory and neuropathic pain.

Because of the role of TRPV1 in pain, TRPV1 antagonists configured to inhibit the activation of TRPV1 have shown some promise in treating patients with neurogenic and/or inflammatory diseases. But TRPV1 antagonists have significant obstacles. For example, common side effects of TRPV1 antagonists include loss of noxious heat sensation, increased burn risk, and hyperthermia. Moreover, due to the systemic nature of many TRPV1 antagonists, these side effects may not be restricted to a localized area, thereby exacerbating their effects.

Accordingly, another potential mechanism recognized in the present disclosure is to treat pain by desensitizing TRPV1 receptors. Most sensory modalities undergo adaptation or desensitization to a stimulus following prolonged or repeated exposure to the stimulus. Adaptation or desensitization may cause a decreased activity or response despite the continuous presence of the stimulus. The more prolonged and extreme the desensitization, the less active the receptor will be.

TRPV1 may be susceptible to desensitization. Activation of TRPV1 leads to a $Ca^{2+}$ influx into nociceptive sensory neurons. This $Ca^{2+}$ influx depolarizes the membrane and prompts the release of proinflammatory neuropeptides from primary afferent nerve terminals. However, prolonged or repeated activation of TRPV1 may result in excessive $Ca^{2+}$ influx, preventing the channel from resetting itself and thus leading to the desensitization of TRPV1. In a desensitized state, TRPV1 will no longer be active, even in the presence of TRPV1 agonists or stimuli. Therefore, repeated or prolonged activation of TRPV1 may provide pain relief by desensitizing TRPV1. As will be discussed in detail below, the present technology includes particular methods configured to maximize the recruitment of TRPV1 to maximize the therapeutic effect following desensitization. For example, applying a pulsing heat stimulus to a pain producing region of a patient can cause repeated activation of TRPV1, thereby leading to excessive Ca2+ influx, TRPV1 desensitization, TRPV1 deactivation, and pain relief.

B. TRPM8

TRPM8, also known as the cold and menthol receptor 1 (CMR1), is a protein that is encoded by the TRPM8 gene and expressed in sensory neurons. TRPM8 is the primary molecular transducer of cold somatosensation in humans. For example, mice lacking functional TRPM8 gene expression are severely impaired in their ability to detect cold temperatures. Remarkably, these animals are deficient in many diverse aspects of cold signaling, including cool and noxious cold perception, injury-evoked sensitization to cold, and cooling-induced analgesia.

As discussed previously, FIG. 12A illustrates the activation of TRPM8 at various temperatures. Line 1202 depicts TRPM8 activity at various temperatures and reflects that TRPM8 is activated as temperatures decrease below about 25° C. TRPM8 may also be activated at temperatures above about 42° C. TRPM8 may also be activated by cooling agents, such as menthol, icilin, and/or derivatives thereof. For example, some of the most selective agonists of TRPM8 include menthol derivatives such as WS-12 and CPS-369.

TRPM8 is an ion channel, which, upon activation, allows Na+ and Ca2+ ions to enter the cell, leading to depolarization and the generation of an action potential. The signal is conducted from primary afferents (type C and A-A), eventually leading to the sensation of cold and cold pain. In contrast to the TRPV1 (capsaicin) receptor, which is potentiated by low pH, acidic conditions inhibit the TRPM8 Ca2+ response to stimuli. Thus, the TRPV1 and TRPM8 receptors may act together in response to inflammatory conditions: TRPV1, by proton action, increases the burning sensation of pain, while the acidity inhibits TRPM8 to block the more pleasant sensation of coolness in more dire instances of pain.

Like with TRPV1, TRPM8 may be associated with many causes of pain. For example, TRPM8 upregulation in bladder tissues correlates with pain in patients with painful bladder syndromes, and TRPM8 is upregulated in many prostate cancer cell lines. However, low concentrations of TRPM8 agonists such as menthol may be antihyperalgesic in certain conditions (e.g., reducing sensitivity to pain), but high concentrations of TRPM8 agonists may cause both cold and mechanical hyperalgesia (e.g., increased sensitivity to pain). TRPM8 knockout mice not only indicated that TRPM8 is required for cold sensation but also revealed that TRPM8 mediates both cold and mechanical allodynia in rodent models of neuropathic pain. Therefore, TRPM8 antagonists may be effective in reversing established pain in neuropathic and visceral pain models.

TRPM8 may be susceptible to both sensitization and desensitization. TRPM8 sensitization increases the sensation of cold and/or cold pain, also known as cold hyperalgesia. For example, applying 40% L-menthol to the forearm results in increased sensitization to the menthol stimulus. An A fiber conduction blockade of the superficial radial nerve reduces the menthol-induced sensation of cold and hyperalgesia.

This likely occurs because blocking A fiber conduction results in inhibition of a class of group C nerve fiber nociceptors needed to transduce the sensation of pain. Thus, menthol may sensitize cold-sensitive peripheral C nociceptors and activate cold-specific A-Δ fibers under certain circumstances.

However, TRPM8 may also experience desensitization following prolonged or repeated exposure to cold and/or to menthol. For example, after initial sensitization to menthol exposure, TRPM8 response to menthol may decline over time. This desensitization may be a result of, for example, the influx of Ca2+ into the cell following activation, which in turn causes a reduction in excitability of TRPM8. For example, TRPM8 channels may show decreasing activity during cold or menthol application in the presence of extracellular $Ca^{2+}$.

The TRPM8 receptor may work in conjunction with the TRPV1 receptor to maintain a feasible threshold temperature range in mammalian cells. For example, the perception of stimulation of TRPM8 and/or TRPV1 occurs at the spinal cord and brain, which integrates signals from different fibers of varying sensitivity to temperature to produce a thermal sensation.

C. Cross Desensitization of TRPV1 and TRPM8

Cold and warm receptors may also exhibit cross desensitization. For example, TRPV1 and TRPM8 may cross desensitize following the prolonged exposure to at least one of the receptors' agonists. As discussed previously, TRPV1 may desensitize following prolonged exposure to heat, capsaicin, or another TRPV1 activating agent, and TRPM8 may desensitize following prolonged exposure to heat, cold, menthol, or another TRPV1 activating agent. Additionally, prolonged menthol exposure may desensitize TRPV1 (via cross-desensitization) and prolonged capsaicin exposure may desensitize TRPM8 (via cross-desensitization). Cross-desensitization may also occur in channels following repeated and prolonged exposure to heat.

D. Clinical Significance of TRPV1 and TRPV8

As discussed herein, cold receptors such as TRPM8 can begin signaling warnings at temperatures of 40° C. Warm receptors, such as TRPV1, maximize signaling at approximately 40-49° C. Thus, exponential recruitment of both warm and cold receptors occurs between higher temperatures such as 40° C. to 49° C.

Despite this, traditional heat therapies operate at temperatures of 40° C. or less because prolonged exposure to heat above 40° C. may lead to tissue damage. Yet, as described herein, the primary therapeutic benefit of heat therapy may occur at temperatures above 40° C. because temperatures higher than 40° C. result in the recruitment of more thermoreceptors, thus leading to the desensitization of more heat activated and pain-associated receptors, such as TRPV1. Accordingly, current heat therapies operating at less than 40° C. are providing at best sub-optimal pain relief by failing to recruit certain thermoreceptors.

The present technology provides systems and methods for applying heat on the skin at temperatures above at least 40° C., and ranging up to 49° C. By providing such heat, skin temperature may at least temporarily rise above 40° C., thereby activating certain thermoreceptors. Therefore, the systems and methods described herein can provide effective pain relief by recruiting and desensitizing thermoreceptors such as TRPV1 and/or TRPM8.

V. SELECTED EMBODIMENTS OF METHODS OF APPLYING STIMULI TO DESENSITIZE THERMORECEPTORS

The present technology includes methods of applying stimuli to reduce pain. For example, certain methods described herein activate the skin's thermoreceptors (e.g., the thermoTRPs) to block and/or otherwise mask the sensation of pain. In some embodiments, the present technology is configured to desensitize specific thermoreceptors such as TRPV1, TRPV2, TRPV3, TRPV4, TRPA1, and/or TRPM8 to reduce the sensation of pain.

In some embodiments, both cold and warm thermoreceptors are targeted. In other embodiments, only cold receptors or only warm receptors are targeted. The present technology and methods may be advantageous over existing pain relief pharmaceutical formulations or devices because they locally target pain producing regions of the body and do not contain risks inherent with chronic pharmaceutical dosing. Moreover, the present technology and methods may be advantageous over existing thermal therapies because the present technology may recruit and desensitize more thermoreceptors, thus providing a more effective therapy.

The present technology includes applying a stimulus to the skin of a patient. A number of different stimuli may utilized. For example, heat may be applied at any temperature in the range of about 35-49° C. For example, heat may be applied at about 35° C., 36° C., 37° C., 38° C., 39° C., 40° C., 41° C., 42° C., 43° C., 44° C., 45° C., 46° C., 47° C., 48° C., and/or 49° C. As discussed above, both cold and warm receptors (e.g., TRPM8 and/or TRPV1) may be activated by such temperatures, thereby desensitizing the receptors and contributing to pain reduction. Other suitable stimuli include compounds configured to activate cold receptors, warm receptors, and/or both cold and warm receptors. Such compounds may include, for example, menthol, menthol derivatives, icilin, capsaicin, and capsaicin derivatives.

In some embodiments, the stimulus is applied to one or more continuous surface areas of skin. For example, the stimulus may be applied to at least one surface area of skin that is 10 square inches or less, the stimulus may be applied to at least one surface area of skin that is less than about 6 square inches, the stimulus may be applied to at least one surface area of skin that is less than about 3 square inches, and/or the stimulus may be applied to at least one surface area of skin that is less than about 2 square inches. In other embodiments, the stimulus may be applied to a surface area of skin greater than 10 square inches.

In some embodiments, the stimulus delivery systems described herein can be used to apply the therapeutic stimuli to a patient. The stimulus delivery systems may apply the stimuli in many different patterns, magnitudes, cycles, etc. For example, a control unit (e.g., the control station 230) can be used to activate and control one or more wearable devices (e.g., the stimulus pods 110) to apply stimuli according to a predetermined heating cycle and/or pattern. In some embodiments, the stimulus pods 110 are configured to be placed in various locations on the skin of the patient to provide therapeutic heat treatment for relieving pain. The following disclosure details a few specific methods of applying stimuli using the delivery systems of the present technology. However, one skilled in the art will appreciate that the present technology can be used in many different manners to alleviate pain, treat ailments, etc., without deviating from the scope of the present technology. Moreover, while reference is made herein to the stimulus pod system 100, one skilled in the art will appreciate that the following methods can be carried out using other suitable heat producing devices and/or topical compounds—for example, those described in detail in U.S. Pat. No. 7,871,427, tilted "APPARATUS AND METHOD FOR USING A PORTABLE THERMAL DEVICE TO REDUCE ACCOMMODATION OF NERVE RECEPTORS," and filed Feb. 8, 2006; and U.S.

Pat. No. 8,579,953, titled "DEVICES AND METHODS FOR THERAPEUTIC HEAT TREATMENT," and filed Dec. 8, 2008, each of which is incorporated herein by reference in its entirety.

1. Selected Embodiments of Low-Level Heating and Cooling Combined with Intermittent High-Level Heating In some embodiments, the present technology can be configured to apply a continuous amount of low-level heat combined with discrete amounts or intermittent bursts of high-level heat to a patient. The intermittent bursts of high-level heat may enable recruitment, activation, and/or desensitization of thermoreceptors that are normally only activated at temperatures higher than those provided by traditional heat therapy. For example, as discussed above, tissue damage may occur following prolonged exposure to temperatures above 40° C. Accordingly, traditional heat therapies typically do not exceed 40° C. However, the present technology can apply heat therapy at temperatures above 40° C. because the present technology can be configured to apply intermittent bursts of heat above 40° C. while avoiding the prolonged exposure that may lead to tissue damage. Because heat can be applied at temperatures above 40° C., more thermoreceptors may be recruited, activated, and/or desensitized than in traditional static heat therapy.

As described in detail below, the bursts of heat can be at distinct locations within or around the areas producing the low-level heat. The low-level heat can be maintained as a constant application of heat (e.g., heating below 42° C., 41° C., 40° C., etc.) while the high-level heat is applied in intermittent bursts (e.g., milliseconds in some embodiments). In certain embodiments of the present disclosure, bursts of heat in the range of about 40-55° C. are applied to discrete areas of skin to excite the receptors. Other suitable ranges may include, for example, about 40-49° C., 40-48° C., 40-47° C., 40-46° C., and/or 40-45° C. In other embodiments, however, the thermal bursts can include temperatures higher or lower than the range of 40-55° C. For the purposes of this disclosure, thermal bursts can be defined as the application of increased heat in discrete areas where the temperature of the burst ranges from 0.1° C. to 25° C. or more above the baseline temperature of the continuous low-level heat application. The thermal bursts can include a ramp up speed ranging from milliseconds to minutes to reach a maximum temperature. In addition, and as described below, the size of the area applying the thermal burst may be relatively small in comparison to the area applying the low-level heat. In other embodiments, however, the area applying the thermal burst may be approximately equal to or less than the area applying the low-level heat.

In some embodiments, a method of applying heat to a living body includes applying a constant amount of heat to a region of the body at a first temperature (e.g., via a stimulus pod 110). The method can also include applying intermittent amounts of heat to the region (e.g., via the stimulus pod 110). The intermittent amounts of heat may be applied at a second temperature greater than the first temperature.

In some embodiments, a method of applying heat to a living body includes applying a constant amount of heat to a first region of the body at a first temperature (e.g., via a first one of the stimulus pods 110). The method can also include applying intermittent amounts of heat to a second region of the body (e.g., via a second one of the stimulus pods 110). The intermittent amounts of heat may be applied at a second temperature greater than the first temperature. In some embodiments, the second region can partially or fully overlap the first region. And in some embodiments, the intermittent amounts of heat are delivered at pre-selected, focused points wherein the surface area of the second region is smaller than the surface area of the first region.

A method configured in accordance with another embodiment of the disclosure includes a method of exciting thermoreceptors in a living organism. The method includes heating a first portion of skin with a generally constant amount of heat at a baseline temperature (e.g., via a first one of the stimulus pods 110), and heating a second portion of skin with a burst of heat at a temperature above the baseline temperature (e.g., via second one of the stimulus pods 110) while heating the first portion of skin with the generally constant amount of heat.

Figure 13:
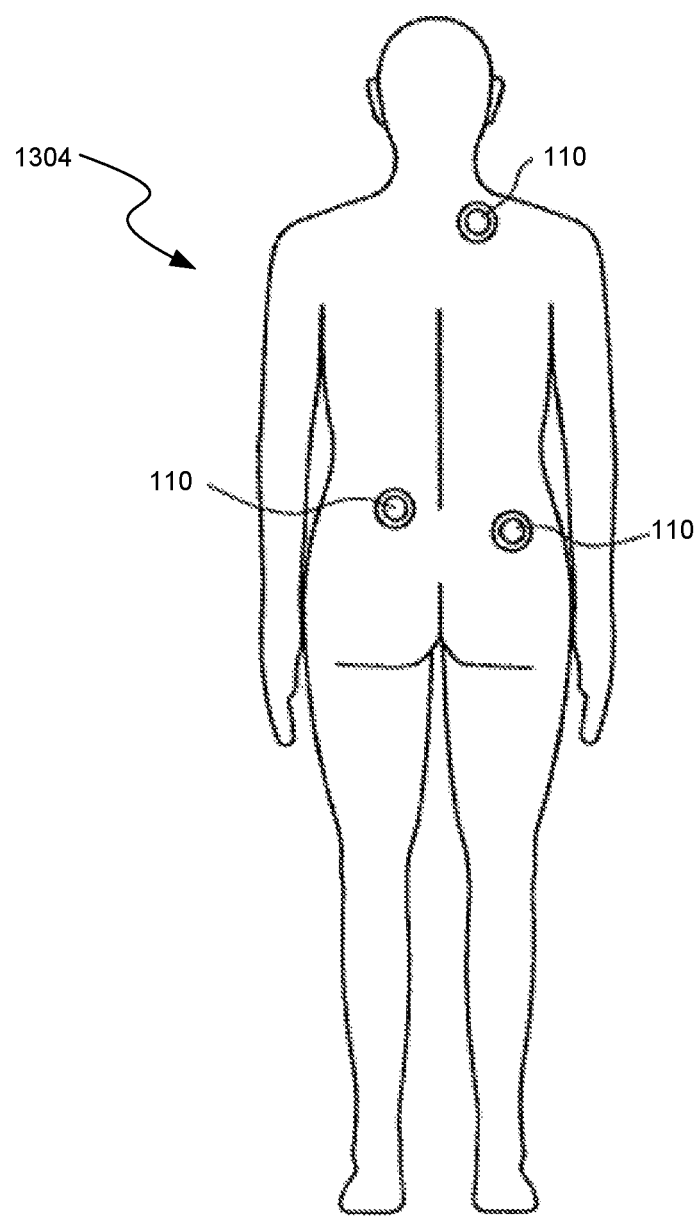
FIG. 13 is a back view of a human form with a plurality of attached stimulus pods configured in accordance an embodiment of the present technology.

As described herein, certain methods in accordance with the present technology may utilize the stimulus pods 110. FIG. 13 is a back view of a human form 1304 wearing a plurality of the stimulus pods 110 (e.g., at the shoulder, lower back, and hip) in accordance with select embodiments. The stimulus pods 110 can be configured to provide continuous low-level heating with periodic bursts or impulses of high-level heat, and can be applied simultaneously to various areas of the body 1304 and can be used in conjunction with one another or independently to provide pain relief. Therefore, the stimulus pods 110 can accommodate users who suffer from pain in areas located in more than one region of the body thus requiring simultaneous treatment. For example, the treatment of conditions such as fibromyalgia, dysmenorrhea, PMS, back and neck pain, sports related injuries, chronic pain etc., may greatly benefit from locating the stimulus pods 110 at different positions to simultaneously treat one or more painful areas.

The combination of the continuous low-level heating and intermittent high-level heating at discrete, focused regions provides several advantages over conventional heating systems. The augmentation of the continuous heating (or cooling), for example, provides enhanced pain relief by promoting blood flow, increasing flexibility, and relaxing muscles, ligaments, and other tissues. The illustrated configuration achieves enhanced pain relief by providing a strong stimulation of the thermoreceptors in the skin and subcutaneous tissues of the body by rapidly changing temperatures. Both the rapid change in temperature (e.g., the rapid increase in temperature during the intermittent burst) and the ability to stimulate at higher temperatures (e.g., above about 40° C.) recruits more thermoreceptors, including TRPV1 and/or TRPM8. Accordingly, the intermittent focused bursts of heat, combined with the constant heat, provide for better receptor recruitment and stimulation, thereby leading to increased desensitization, resulting in better analgesic results.

2. Selected Embodiments of Heat Cycling to Desensitize Thermoreceptors

In some embodiments, the present technology can be used to provide energy and/or heat to a patient to desensitize certain pain-associated thermoreceptors (e.g., TRPV1). The method includes increasing the temperature of a heating element (e.g., one or more of the stimulus surfaces 150 of the stimulus pods 110) to provide a first temperature ramp-up period, holding the temperature of the heating element at a predetermined therapeutic level, decreasing the temperature of the heating device during a ramp-down period, and holding the temperature of the heating device at a predetermined soak level, wherein the soak level temperature is less than the therapeutic level temperature by at least 1° C.

In operation, the heating device (e.g., one or more of the stimulus pods 110) may deliver heat intermittently. The heat may be applied for a period long enough to heat the skin to a desired level; upon reaching the desired skin temperature the device turns off and the skin is allowed to cool; after a preprogrammed interval the device may reactivate the heat unit and the cycle repeats. Alternatively, multiple cycles may be delivered sequentially for a predetermined duration.

Figure 14:
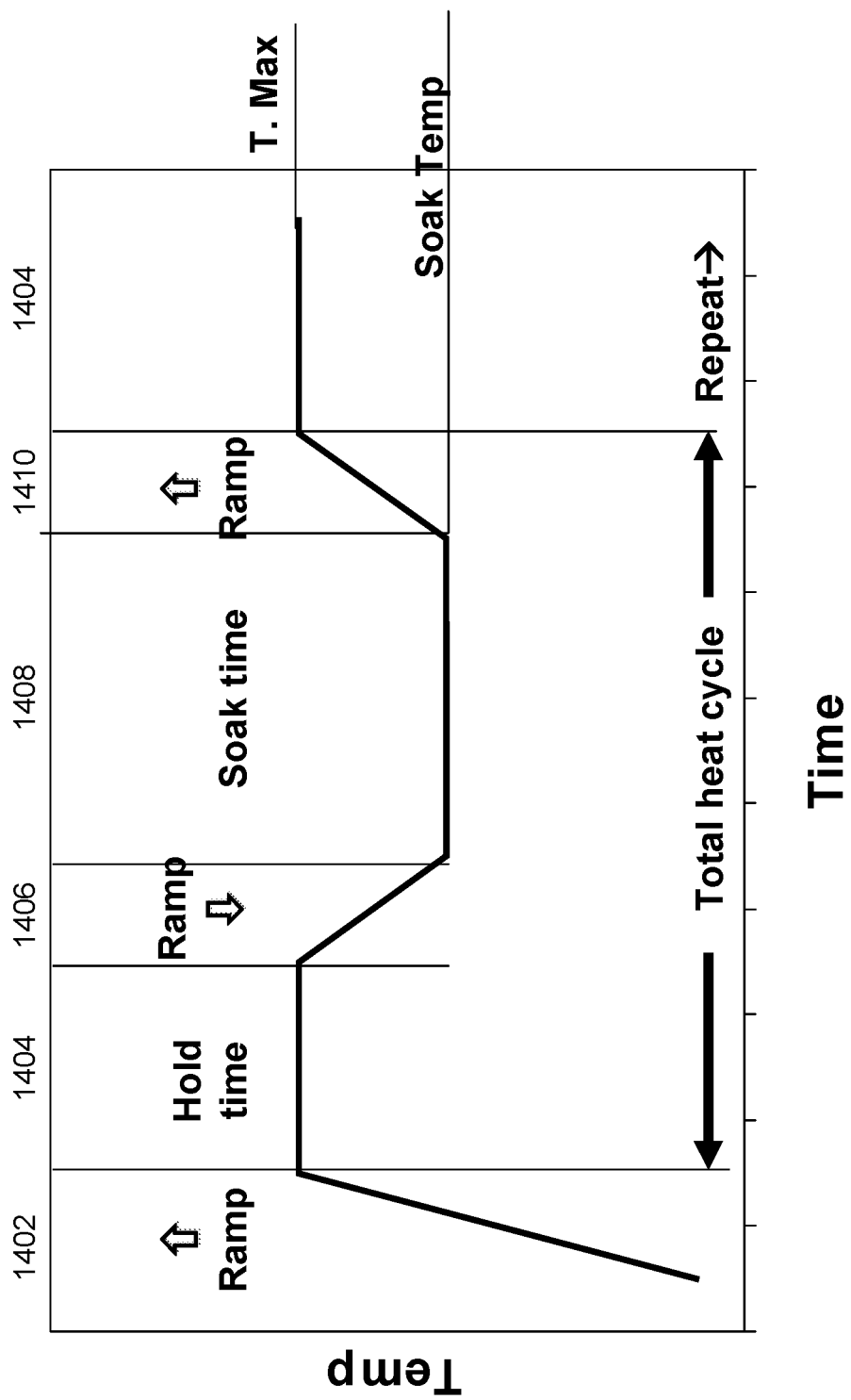
FIG. 14 is a graph of temperature versus time illustrating a variable heat cycle in accordance with an embodiment of the present technology.
Figure 15:
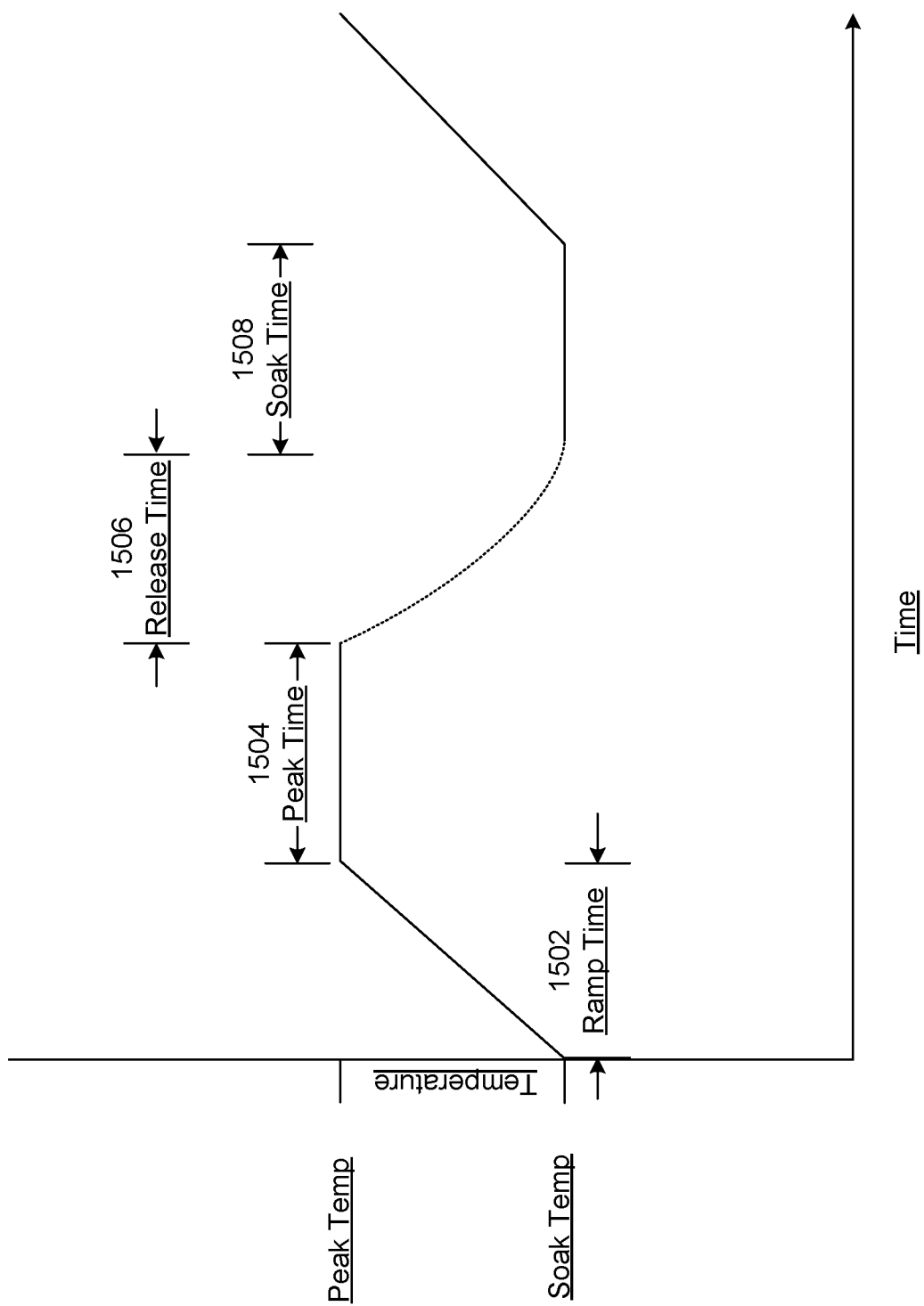
FIG. 15 is a graph of temperature versus time illustrating a variable heat cycle in accordance with another embodiment of the present technology.

FIG. 14, for example, is a graph of temperature versus time illustrating a variable heat cycle for a heating element configured in accordance with an embodiment of the present technology. In the illustrated embodiment, the variable heat cycle includes a first temperature ramp-up phase 1402, a therapeutic temperature hold phase 1404, a ramp-down phase 1406, a soak phase 1408, and a second ramp-up phase 1410. FIG. 15 is a graph of temperature versus time illustrating a variable heat cycle for the heating element configured in accordance with another embodiment of the present technology. In the illustrated embodiment, the variable heat cycle includes a ramp-up phase 1502, a peak-time hold phase 1504, a release phase 1506, and a soak phase 1508.

In some embodiments, the ramp-up phases 1402, 1410, and 1502 may be less than about 4 seconds. For example, the ramp-up phase may be about 3 seconds, about 2 seconds, about 1 second, or less than 1 second. A short ramp up phase can be beneficial because a quick change in temperature (e.g., a short ramp-up phase) can recruit more thermoreceptors then a slow change in temperature. More specifically, a quick change in temperature can result in a rapid energy transfer between the heating device and the skin. This rapid energy transfer between the heating device and skin can activate thermoreceptors that may only traditionally be activated at higher static temperatures. Thus, more receptors may be recruited by "shocking" the receptors with a quick energy change. In contrast, a slower change in temperature (e.g., a ramp-up phase of about 4 seconds or more) provides a less intense change in energy and/or transfer of energy between the heating device and the skin and thus may not provide the same level of thermoreceptor recruitment. Accordingly, one benefit of the present technology is the recruitment of additional thermoreceptors by having a rapid energy transfer between the heating device and skin.

In some embodiments, the therapeutic temperature hold phase 1404 and the peak-time hold phase 1504 may be less than about 15 seconds. For example, the hold phases 1404 and 1504 may be about 1 second, about 2 seconds, about 3 seconds, about 4 seconds, about 5 seconds, about 6 seconds, about 7 seconds, about 8 seconds, about 9 seconds, about 10 seconds, about 11 seconds, about 12 seconds, about 13 seconds, about 14 seconds, or about 15 seconds. The temperature during hold phases 1404 and 1504 may be greater than about 40° C. For example, the temperature during hold phases 1404 and 1504 may be defined within a range, such as between 40-49° C., 40-48° C., 40-47° C., 40-46° C., or 40-45° C., 41-45° C., 42-45° C., 43-45° C., 44-45° C., or any other suitable range between an upper bound of about 49° C. and a lower bound of about 40° C. The temperature during hold phases 1404 and 1504 may also be defined as a specific temperature, such as about 40° C., 41° C., 42° C., 43° C., 44° C., 45° C., 46° C., 47° C., 48° C., or 49° C. Additionally or alternatively, the temperature during the hold phases 1404 and 1405 by be defined as a target skin temperature for a region of skin adjacent to the heating device. For example, the target skin temperature may be about 40° C., 41° C., 42° C., 43° C., 44° C., 45° C., 46° C., 47° C., 48° C., or 49° C. The target skin temperature may also be defined as a range of temperatures between, for example, 40-49° C., 40-48° C., 40-47° C., 40-46° C., or 40-45° C., 41-45° C., 42-45° C., 43-45° C., 44-45° C. In some embodiments, the temperature may alternatively be defined as an energy applied to the skin.

The ramp-down phase 1406 and the release phase 1506 may take several different forms. For example, the ramp-down phase may be actively controlled and take a linear form, such as illustrated by ramp-down phase 1406. The ramp-down phase may also simply be the result of turning off the energy or heat producing element such that a non-linear decay of heat occurs. For example, release phase 1506 illustrates one such example of the non-linear decay of heat. The decay time will depend on a number of factors, including peak temperature, soak temperature, and the thermal conductivity of the heating surface.

In some embodiments, the soak phase 1408 and 1508 may be held at a temperature higher than the basal body temperature of the user, thus allowing continued therapeutic effects by improving the blood flow to the region and providing muscle relaxation. In other embodiments, the heating device may simply be turned off during the soak phase 1408 and 1508, such that the temperature of the heating device is near the room temperature and/or the basal body temperature of the user (assuming complete decay). The duration of the soak phase 1408 and 1508 can be selected to maintain desensitization of previously desensitized thermoreceptors while simultaneously keeping a thermal flux value within the skin below a tissue-damage inducing threshold. For example, the soak time may be optimized based on identifying a duration for a thermoreceptor to reset (e.g., recover from the CA2+ influx and be capable of firing again). In some embodiments, for example, the soak time could be 60 seconds or less, such as about 55 seconds, about 50 seconds, about 45 seconds, about 40 seconds, about 35 seconds, about 30 seconds, about 25 seconds, about 20 seconds, about 15 seconds, about 10 seconds, or about 5 seconds. In some embodiments, the soak time may be greater than 60 seconds or less than 5 seconds.

The heating cycle including the ramp-up phase, the hold phase, the ramp-down phase, and the soak phase may be repeated at a frequency to maintain at least a partial desensitization of certain thermoreceptors (e.g., TRPV1). Moreover, the heating cycle may be repeated continuously for a preset duration (e.g., five minutes) or number of cycles (e.g., 100 cycles). In some embodiments, the heating cycle may continue until turned off.

FIGS. 16-19 illustrate additional embodiments of applying energy in the form of heat to recruit and desensitize pain-associated thermoreceptors. One skilled in the art will recognize that the principles discussed above with respect to FIGS. 14 and 15 can also be applied to the following embodiments.

Figure 16:
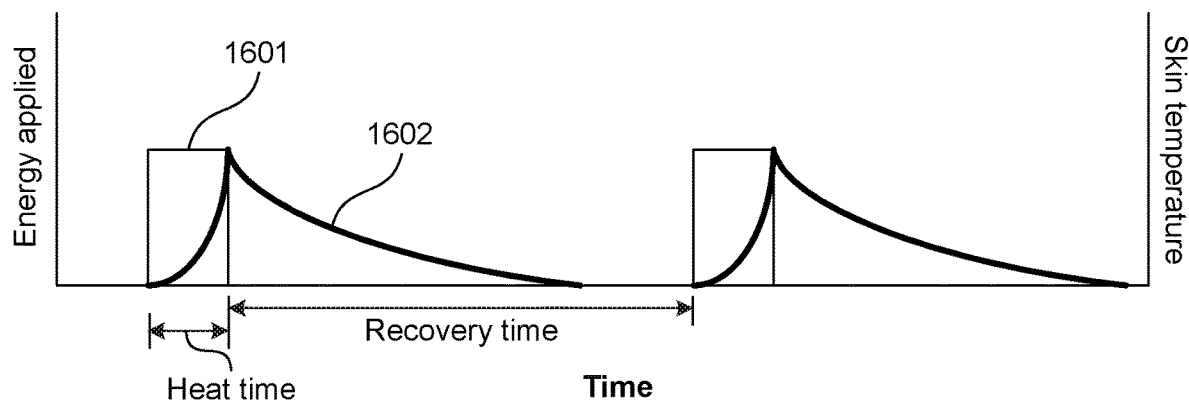
FIG. 16 is a graph of energy applied versus time illustrating the resultant skin temperature of a patient in accordance with an embodiment of the present technology.

FIG. 16 is a graph of energy applied versus time illustrating the energy applied to the system and the resultant skin temperature of a patient in accordance with an embodiment of the present technology. In FIG. 16, bars 1601 indicate how long and how much energy is applied via the stimulus pods 110, and lines 1602 indicate estimated skin temperature for each profile. The heat applied is measured on an arbitrary scale on the left, and the skin temperature is indicated on an arbitrary scale on the right.

Figure 17:
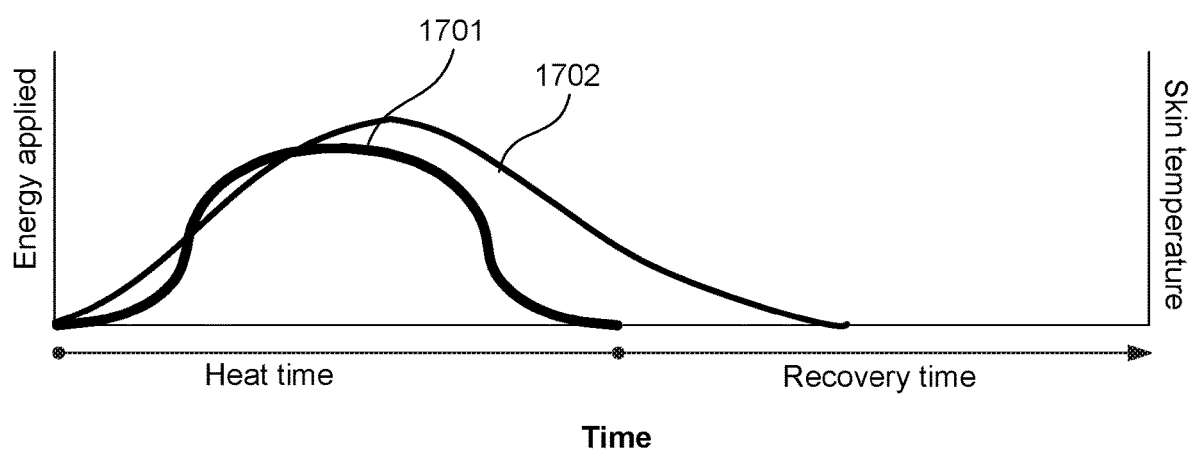
FIG. 17 is a graph of energy applied versus time in accordance with another embodiment of the present technology.

FIG. 17 is a graph of energy applied versus time illustrating a sine wave pattern 1701 of energy applied and the resultant skin temperature 1702 of a patient in accordance with an embodiment of the present technology. In other embodiments, the pattern of applied energy can be a square, crescendo, de-crescendo, intermittent, or any other conceivable pattern. Thus, there are at least five variables that can be adjusted to ensure optimal analgesia; duration of ramp-up time, duration of heating "heat time," "recovery times" between heat times, intensity of heating, and pattern of heating (sine wave, square wave, saw tooth, etc.).

Figure 18:
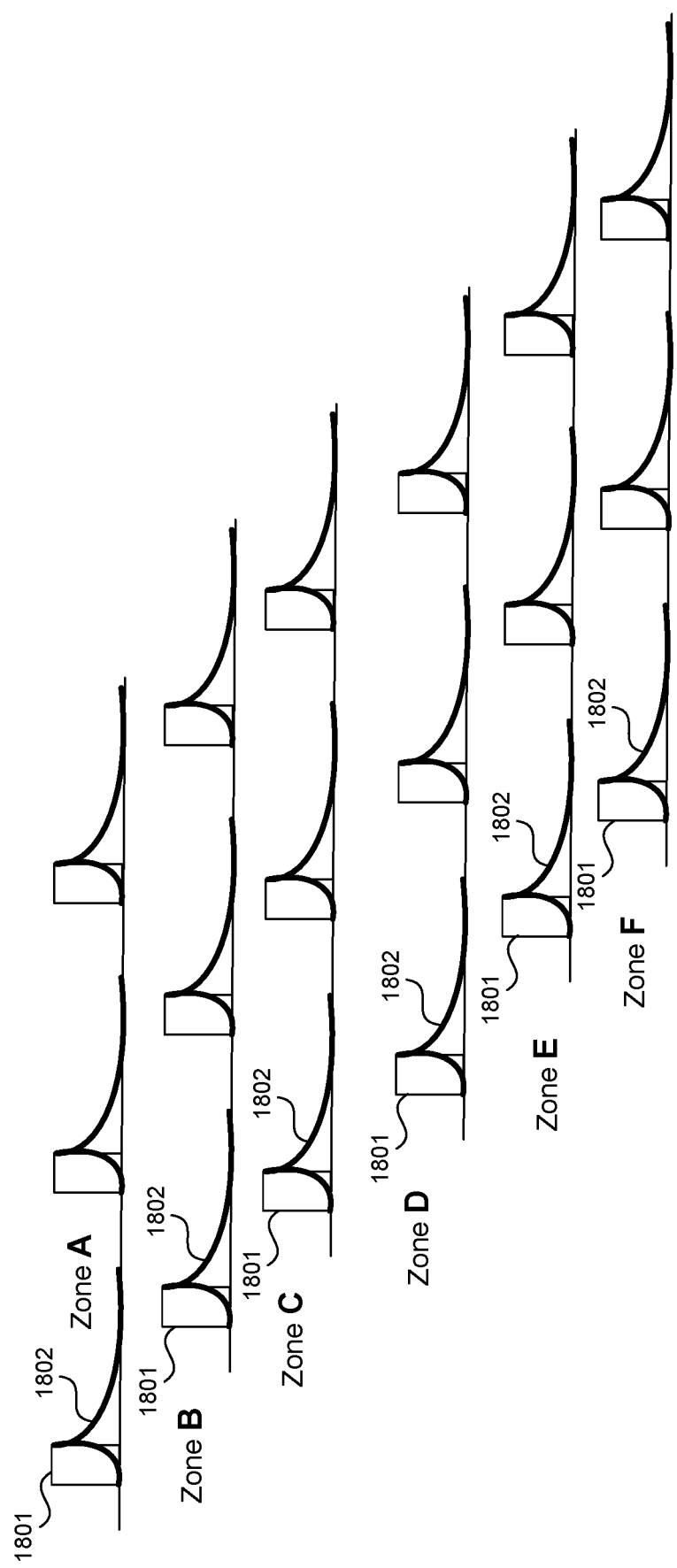
FIG. 18 illustrates energy applied to exemplary thermal zones and the resultant skin temperature of a patient in accordance with an embodiment of the present technology.

FIG. 18 illustrates energy applied to exemplary thermal zones A, B, C, D, E and the resultant skin temperature of a patient in accordance with an embodiment of the present technology. Bars 1801 indicate how long and how much energy is applied, and lines 1802 indicate estimated skin temperature. In some embodiments, the thermal zones A-E can correspond to zones under or proximate to different ones of the stimulus pods 110. In the illustrated embodiment, the skin temperature in the thermal zones A-E has a cascading pattern. In particular, heat is applied to each zone in a sequential pattern. That is, as energy is applied to zone A, zone B rests, then zone B heats while zone A rests, and then zone C heats while zone D rests, and so forth. This has the effect of a wave of heat being passed from zone A to zone E and back again. The principle of moving heat zones can be applied vertically, horizontally, or both to achieve a checkerboard effect or any other conceivable pattern. In other embodiments, the system can deliver any conceivable pattern. For example, heat can be applied in a non-uniform manner. Similarly, by taking advantage of individually controllable heat regions or heat zones (e.g., corresponding to different ones of the stimulus pods 110), the heat can be applied sequentially or in any other imaginable pattern. Sequential heating of individual heat regions as drawn in can enable an entirely different therapeutic sensation to be achieved as compared with heating them all at the same time.

Figure 19:
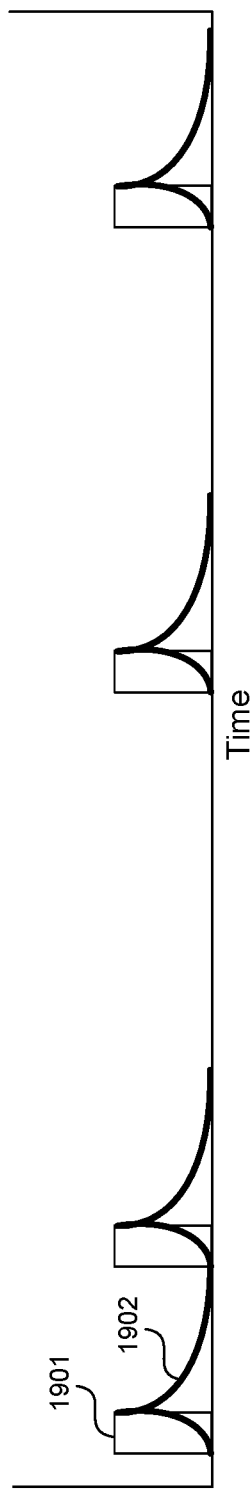
FIG. 19 illustrates an on-demand pattern of variable heat cycles over time as requested by a patient in accordance with an embodiment of the present technology.

FIG. 19 illustrates an on-demand pattern of variable heat cycles over time as requested by a subject in accordance with an embodiment of the present technology. The patient can press an actuator on the stimulus pod 110, such as a lever, a switch, a pressure sensor, or any other activation device as is known in the art, to demand heat on an as-needed basis. Bars 1901 indicate how long and how much energy is applied, and lines 1902 indicate estimated skin temperature. FIG. 19 shows, on an arbitrary time base, the patient demanding analgesia four times. The pattern of heat delivered by the system could be constant or preprogrammed onto a control unit.

The heating cycles described herein have several advantages over previous heat-based therapies. One benefit of certain embodiments of the present technology is the ability to minimize the total amount of heat and/or energy applied to the skin. As previously discussed, pulsing high levels of heat and/or energy with a ramp-up phase of about 4 seconds or less results in less total heat and/or total energy being applied to the skin but is nonetheless effective at recruiting thermoreceptors. For example, a short ramp-up phase (e.g., about 4 seconds or less) recruits more thermoreceptors than a long ramp-up phase. Thus, less total energy must be applied by relying in part on the rapid change of energy to recruit receptors, rather than relying on a total peak energy or temperature. Moreover, by pulsing energy, the benefit of this rapid change of energy may be repeatedly captured through repetitive ramp-up, hold, ramp-down, and soak cycles.

Another advantage of pulsing heat and/or energy is that less total heat and/or energy is applied to the skin through repeated heating cycles, since, during the soak cycles, the heat and/or energy applied to the skin can be minimal. This enables the hold phase of the heat cycle to have higher temperatures than traditional heating therapies, thereby recruiting more thermoreceptors. Accordingly, the heating cycles described herein enable maximal recruitment of thermoreceptors (and therapeutic efficacy) while the tissue remains at a temperature and/or thermal flux below a dangerous level.

Yet another advantage of the variable heat cycles is reduced power demand and consumption during the ramp-down or release phase when the thermal device does not draw power from the power supply, or draws reduced power from the power supply. Reduced power consumption results in a more efficient device with a longer life cycle and provides cost savings.

Yet another advantage of the present technology is that the heating devices can be portable and can be conveniently worn by the subject such that pain relief is available as needed. Moreover, in some embodiments, the user may selectively control certain parameters of the heating cycles via a control station such as a cell phone or other device capable of communicating with the stimulus producing device. For example, the user may be able to select, via a touch-screen display or other interactive portion of the control station (e.g., buttons, switches, etc.) a duration and/or pulse frequency for the heat cycling. The user may also select a baseline temperature to maintain during the soak phase and/or a maximum temperature not to surpass during the hold phase. The user can further select the number of heating cycles and/or total duration to apply the heating cycles.

According to aspects of the present technology, the heating devices and heating cycles described herein are designed to relieve pain and/or assist with healing in a variety of medical conditions such as low, mid, or upper back pain, muscular pain, dysmenorrhea, headaches, fibromyalgia, post-herpetic neuralgia, nerve injuries and neuropathies, injuries to extremities, and sprains and strains. The present technology may further be used in conjunction with other therapies known in the art, such as TENS. When combined with other therapies, the present technology may increase the efficacy of these other therapies.

3. Select Embodiments Including Non-Thermic Stimuli

Some embodiments of the present technology utilize topical non-thermal stimuli (e.g., topical compounds) to recruit, activate, and desensitize certain thermoreceptors. For example, menthol, icilin, menthol derivatives, capsaicin, capsaicin derivatives, cannabinoids, NSAIDs, paracetamol, paracetamol metabolites, and/or other compounds or formulations configured to stimulate thermoreceptors may be applied to the skin of a patient (collectively referred to as "non-thermal stimuli"). These non-thermal stimuli may be provided alone or in combination with each other, as well as with other heat therapies described herein. In one embodiment, for example, both capsaicin and menthol are applied to the skin to ensure recruitment of both TRPV1 and TRPM8. In such embodiments, capsaicin and menthol can be applied at the same time or at separate times via alternating applications. In some embodiments, however, menthol is exclusively applied, and/or capsaicin is exclusively applied. As discussed above, menthol and capsaicin may both induce cross-desensitization of TRPV1 and TRPM8. Therefore, even if menthol or capsaicin is exclusively applied, both TRPV1 and TRPM8 may both be recruited and desensitized.

The non-thermal stimuli may be applied to a surface area of the skin. As it is absorbed into the skin, the non-thermal stimuli may activate thermoreceptors. After excessive CA2+ influx, the thermoreceptors will desensitize, resulting in pain relief. In some embodiments, the surface are the non-thermal stimuli is applied to is 10 square inches or less. For example, the surface area may less than about 6 square inches, less than about 3 square inches, or less than about 2 square inches.

The non-thermal stimuli can be applied in a controlled manner similar to the heat cycling described above with respect to thermal stimuli. In some embodiments, the stimulus pods 110 described herein may be configured to apply the non-thermal stimuli (e.g., via the adhesive surface of the anchor 120 or via another applicator included on the stimulus pods 110). In some embodiments, however, the non-thermal stimuli may be applied via another device or mechanism known in the art. Regardless of the applicating device, certain embodiments of the present technology utilize repeatedly applying the non-thermal stimuli via controlled release. The controlled release will minimize unnecessary skin exposure to these non-thermal stimuli. Exemplary controlled release mechanisms include, for example, use of a time release chemical formula or fluidic wicking. Further controlled release mechanisms include electronically controlled release by microfluidics, a solenoid applicator, a micro-needle applicator, electrophoresis, magnetophoresis, and other techniques known in the art. The non-thermal stimuli may be repeatedly applied in a manner configured to stimulate and/or desensitize at least a subset of thermoreceptors.

In some embodiments, the non-thermal stimuli may be applied with the heat therapies described above. For example, a predetermined dose of non-thermal stimuli can be applied before (e.g., 5 minutes before, 1 minute before, immediately before) the initiation of a heat cycle. As another example, a predetermined dose of the non-thermal stimuli can be applied during the heating cycle and/or after the heating cycle. Applying heat may increase the efficacy of the non-thermal stimuli by, for example, increasing absorption and/or rate of absorption of the non-thermal stimuli. Accordingly, by combining the non-thermal stimuli with heat therapy, less overall non-thermal stimuli must be applied to achieve the same or greater therapeutic effect. Thus, in some embodiments, the predetermined dose may include a smaller overall dose or a less concentrated dose than doses applied without heat therapy.

When applied with heat, the non-thermal stimuli may be applied to the same surface area of skin as the heat, to a substantially similar surface area of skin as the heat, to an overlapping surface area of skin as the heat, or to a different area of skin as the heat. As can be appreciated by one of skill in the art, any number of overlapping and/or other patterns of application can be envisioned based on the disclosure herein and are included in the present technology.

VI. EXAMPLES

The present technology may be better understood with reference to the following non-limiting examples.

1. A method of treating pain comprising pulsing heat into a volume of tissue including thermoreceptors, wherein—
   the pulsed heat is between 42 degrees and 49 degrees Celsius,
   and
   the pulsed heat is configured to stimulate the thermoreceptors.

2. The method of example 1, wherein pulsing heat into the volume of tissue comprises a heat cycle including a ramp-up phase, a hold phase, a ramp-down phase, and a soak phase.

3. The method of example 2, wherein the ramp-up phase is about 4 seconds or less.

4. The method of examples 2 or 3, wherein the hold phase is about 10 seconds or less.

5. The method of any one of examples 2-4, wherein the hold phase includes applying heat to the tissue at between 42 degrees and 49 degrees Celsius.

6. The method of any one of examples 2-5, wherein the soak phase includes applying heat at a basal body temperature or not applying heat.

7. The method of any one of examples 2-6, wherein the heat cycle is iteratively repeated for a set duration.

8. The method of examples 2-7, wherein the heat cycle is configured to desensitize at least a subset of the thermoreceptors.

9. The method of any one of examples 2-8, wherein the heat cycle is iteratively repeated at a frequency configured to induce desensitization of at least a subset of the thermoreceptors.

10. The method of any one of examples 2-8, further comprising iteratively repeating the heat cycle at a frequency configured to maintain desensitization of at least the subset of thermoreceptors.

11. The method of any one of examples 1-10, wherein the pulsed heat is configured to stimulate and/or induce desensitization of both warm thermoreceptors and cold thermoreceptors.

12. The method of any one of examples 1-11, wherein the pulsed heat is configured to stimulate and/or induce desensitization of TRPV1 receptors, 13. The method of any one of examples 1-11, wherein the pulsed heat is configured to stimulate and/or induce desensitization of TRPM8 receptors and/or TRPA1 receptors.

14. The method of any one of examples 1-11, wherein the pulsed heat is applied to a substantially continuous surface area of skin that is less than 3 square inches.

15. A method of treating pain comprising:
   applying energy to a volume of tissue including thermoreceptors, wherein—
   the energy induces a skin temperature between 42 degrees and 49 degrees Celsius,
   the energy induces a thermal flux in the skin that is below a tissue-damaging threshold, and
   the energy induces stimulation of thermoreceptors.

16. The method of example 15, wherein applying energy to the volume of tissue comprises a cycle including a ramp-up phase, a hold phase, a ramp-down phase, and a soak phase.

17. The method of example 16, wherein the ramp-up phase is about 4 seconds or less.

18. The method of example 16 or 17, wherein the hold phase is about 10 seconds or less, and wherein, during the hold phase, energy is applied to the volume of tissue to induce the skin temperature between 42 degrees and 49 degrees Celsius.

19. The method of any one of examples 16-18, wherein the soak phase comprises applying no energy to the volume of tissue, and wherein, during the soak phase, the temperature of the skin falls below 42 degrees Celsius.

20. The method of any one of examples 16-19, wherein the cycle is iteratively repeated for a set duration.

21. The method of any one of examples 16-19, wherein the cycle is configured to desensitize at least a subset of the thermoreceptors.

22. The method of any one of examples 16-21, wherein the cycle is iteratively repeated at a frequency configured to induce desensitization of at least a subset of the thermoreceptors.

23. The method of any one of examples 16-22, further comprising iteratively repeating the cycle at a frequency configured to maintain desensitization of at least the subset of thermoreceptors.

24. The method of any one of examples 15-23, wherein the energy is configured to stimulate and/or induce desensitization of both warm thermoreceptors and cold thermoreceptors.

25. The method of any one of examples 15-24, wherein the pulsed heat is configured to stimulate and/or induce desensitization of TRPV1 receptors.

26. The method of any one of examples 15-25, wherein the pulsed heat is configured to stimulate and/or induce desensitization of TRPM8 and/or TRPMA1 receptors.

27. A method of treating pain comprising:
repeatedly applying a topical compound to a volume of tissue including thermoreceptors, wherein the topical compound is applied to at least one continuous surface area of the tissue that is 3 square inches or less, and wherein the topical compound is configured to induce desensitization of at least a subset of the thermoreceptors.

28. The method of example 27, wherein repeatedly applying the topical compound comprises applying the topical compound two or more times within a therapy session.

29. The method of examples 27 or 28, wherein the topical compound is controllably applied via chemical time release or fluidic wicking.

30. The method of examples 27 or 28, wherein the topical compounds is controllably applied via electronically controlled microfluidics, electronically controlled electrophoresis, electronically controlled solenoid, electronically controlled micro-needle and/or electronically controlled magnetophoresis.

31. The method of any one of examples 27-30, wherein the topical compound is capsaicin, a capsaicin derivate, menthol, a menthol derivative, icilin, a cannabinoid, an NSAID, paracetamol, or paracetamol metabolites.

32. The method of any one of examples 27-31, wherein repeatedly applying a topical compound to a volume of tissue comprises alternatingly applying capsaicin or a capsaicin derivative and menthol, a menthol derivative, icilin, a cannabinoid, an NSAID, paracetamol, or paracetamol metabolites.

33. The method of any one of examples 27-32, further comprising applying heat to the volume of tissue concurrent with the topical compound to increase the absorption of the topical compound.

34. The method of any one of examples 27-33, wherein the topical compound is configured to induce desensitization of both warm thermoreceptors and cold thermoreceptors.

35. The method of any one of examples 27-34, wherein the topical compound is configured to induce desensitization of TRPV1.

36. The method of any one of examples 27-35, wherein the topical compound is configured to induce desensitization of TRPM8 and/or TRPA1.

37. A system for treating pain, the system comprising:
an energy producing element having a stimulus surface, wherein the stimulus surface is configured to be placed in contact with skin, and wherein the energy producing element is configured to pulse energy into the skin via the stimulus surface,
wherein the pulsed energy is defined by a ramp-up phase, a hold phase, a ramp-down phase, and a soak phase, wherein the ramp-up phase is four seconds or less, and wherein the pulsed energy is configured to stimulate thermoreceptors within the skin.

38. The system of example 37, further comprising an electrical circuit configured to monitor the temperature of the skin to ensure that the pulsed energy does not cause an injury to the skin.

39. The system of example 38, wherein the electrical circuit is configured to utilize a look-up table, a formula, a chart, or other source of information to predict the characteristic of thermal energy that causes injury to the skin.

40. The system of any one of examples 37-39, further comprising a temperature measuring element configured to sense the temperature of the skin.

41. The system of any one of examples 38-40, wherein the electrical circuit is configured to transmit monitored characteristics to a control device.

42. The system of example 41, wherein the monitored characteristics include the skin's thermal transfer capacity and/or the skin's blood flow.

43. The system of any one of examples 37-42, wherein the pulsed energy is configured to induce a skin temperature between 42 degrees and 49 degrees Celsius.

44. The system of any one of examples 37-43, wherein the pulsed energy is configured to desensitize at least a subset of the thermoreceptors.

45. A method of pulsing heat between 42° C. to 49° C. and applying the pulsed heat to a small surface area of skin thereby activating underlying warm thermoreceptors, and cold thermoreceptors in the skin to produce relief from acute, sub-acute, and chronic pain.

46. The method of example 45, wherein applying the pulsed heat to the skin provides a thermal flux that does not cause tissue injury.

46. The method of example 45, wherein applying the pulsed heat keeps phasic thermoreceptors shutdown for prolonged periods.

47. The method of example 45, wherein the small surface area is between 0.5 to 3 square inches and wherein applying the heat to the small surface area minimizes the amount of thermal energy delivered to the skin.

48. The method of example 45, wherein applying the pulsed heat to the skin comprises applying a therapeutic dose of heat, wherein the therapeutic dose of heat is generated by a conductive heating element controlled by a microprocessor.

49. The method of example 45 wherein the pulsed heat is produced by an electrically resistive heating element with very low thermal mass to facilitate fast thermal rise on activation and minimal retained heat when turned off.

50. The method of example 45 wherein the pulsed heat comprises a therapeutic dose of heat delivered to the skin and wherein applying the pulsed heat comprises applying the therapeutic dose of heat using a radiation-heating element controlled by a microprocessor.

51. The method of example 45 wherein the pulsed heat comprises a therapeutic dose of heat delivered to the skin and wherein applying the pulsed heat comprises applying the therapeutic dose of heat using a convective heating element controlled by a microprocessor.

52. The method of example 45 wherein the pulsed heat can be a saw-tooth and or pulsed wave.

53. The method of example 45 wherein heat flux produced by a heating element is controlled such that the skin temperature is raised over a series of temperature steps prior to a final temperature.

54. An electrical circuit configured to monitor the temperature of skin to ensure that a heating element in contact with the skin and configured to deliver pulses of heat does not cause a thermal injury to the skin.

55. The electrical circuit of example 54, wherein the electrical circuit is configured to utilize a look-up table, a formula, a chart, or other sources of information to predict the characteristic of thermal energy that causes thermal injury to the skin.

56. The electrical circuit of example 54, further comprising a temperature measuring element configured to monitor the temperature of the skin, wherein the temperature measuring element is located at the center of the heating element.

57. The electrical circuit of example 54, wherein monitoring the temperature of skin comprises monitoring the temperature using a non-contact method of measuring skin temperature.

58. The electrical circuit of example 54, wherein the electrical circuit is configured to provide protection and warning against a malfunctioning internal power source or battery.

59. The electrical circuit of example 54, wherein the electrical circuit is configured to transmit information about characteristics of the skin to a mobile app associated with the electrical circuit.

60. The electrical circuit of example 59, wherein the transmitted information comprises information about the skin's thermal transfer capacity.

61. The electrical circuit of example 59, wherein the transmitted information comprises information about the skin's blood flow.

62. A method of stimulating cold fibers to activate these fibers to produce analgesia and a hedonistic experience through thermal stimulation in order to provide both pain relief and a sense of relaxation and empathy.

63. The method of example 62, wherein stimulating cold fibers is used to treat headaches, muscular pain, pain in joints, pain from nerve injury irritation or compression, back, neck, and musculoskeletal pain.

64. A method of exposing skin to cold temperatures for repeated and short durations of time.

65. A method of pulsing heat from water sources to provide pain relief, comprising: applying intense but short pulses of heated water to skin in order to activate both A-$\Delta$ and A-$\beta$ receptors.

66. A method of applying or exposing topical compounds for repeated, short durations to a surface area of skin to desensitize receptors and produce relief from acute, sub-acute and chronic pain.

67. The method of example 66 wherein the surface area of skin exposed is 0.5 to 3 square inches.

68. The method of example 66 wherein the compound's application to the skin is controlled by chemical time release.

69. The method of example 66 wherein the compound's application to the skin is controlled by fluidic wicking.

70. The method of example 66 wherein the compound's application to the skin is by electronically controlled microfluidics.

71. The method of example 66 wherein the compound's application to the skin is by electronically controlled electrophoresis.

72. The method of example 66 wherein the compound's application to the skin is by magnetophoresis or electronically controlled magnetophoresis.

73. The method of example 66 wherein the compound's application to the skin is by electronically controlled solenoid.

74. The method of example 66 wherein the compound's application to the skin is by electronically controlled microneedles.

75. The method of example 66 wherein the topical compound is capsaicin.

76. The method of example 66, further comprising alternating the application or exposure of Capsaicin and Menthol to the skin to produce relief from acute, sub-acute, and chronic pain.

77. The method of example 66, further comprising applying capsaicin to one skin area and menthol to another skin area to produce relief from acute, sub-acute, and chronic pain.

78. A method of applying heat on the skin to improve the absorption of topical compound/s.

79. The method of example 78, wherein the heat is pulsed.

80. A system for treating pain, the system comprising:
an energy producing element having a stimulus surface, wherein the stimulus surface is configured to be placed in contact with skin, and wherein the energy producing element is configured to pulse energy into the skin via the stimulus surface; and
a topical compound applicator configured to apply the topical compound to the skin;
wherein the pulsed energy and topical compound are configured to stimulate thermoreceptors within a volume of tissue.

81. The system of example 80, wherein the pulsed energy includes a ramp-up phase, a hold phase, a ramp-down phase, and a soak phase.

82. The system of example 81, wherein during the hold phase, the energy producing element applies directs and energy at the volume of tissue configured to induce a skin temperature between 42 and 49 degrees Celsius.

83. The system of any one of examples 80-82, wherein the topical compound is capsaicin, a capsaicin derivate, menthol, a menthol derivative, icilin, a cannabinoid, an NSAID, paracetamol, or a paracetamol metabolite.

84. The system of any one of examples 80-83, wherein the topical compound is controllably applied via chemical time release or fluidic wicking 85. The system of any one of examples 80-83, wherein the topical compound is controllably applied via electronically controlled microfluidics, electronically controlled electrophoresis, electronically controlled solenoid, magnetophoresis and/or electronically controlled magnetophoresis.

86. The system of any one of examples 80-85, wherein the pulsed energy and/or the topical compound are configured to stimulate and desensitize TRPV1, TRPM8, and/or TRPA1.

VII. CONCLUSION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above detailed description of embodiments of the present technology is not intended to be exhaustive or to limit the present technology to the precise form disclosed above. While specific embodiments of, and examples for, the present technology are described above for illustrative purposes, various equivalent modifications are possible within the scope of the present technology, as those skilled in the relevant art will recognize. The teachings of the present technology provided herein can be applied to other systems, not necessarily the system described above. The elements and acts of the various embodiments described above can be combined to provide further embodiments. All of the above patents and applications and other references, including any that may be listed in accompanying filing papers, are incorporated herein by reference. Aspects of the present technology can be modified, if necessary, to employ the systems, functions, and concepts of the various references described above to provide yet further embodiments of the present technology.

These and other changes can be made to the present technology in light of the above Detailed Description. While the above description details certain embodiments of the present technology and describes the best mode contemplated, no matter how detailed the above appears in text, the present technology can be practiced in many ways. Details of the system may vary considerably in its implementation details, while still being encompassed by the present technology disclosed herein. As noted above, particular terminology used when describing certain features or aspects of the present technology should not be taken to imply that the terminology is being redefined herein to be restricted to any specific characteristics, features, or aspects of the present technology with which that terminology is associated. In general, the terms used in the following claims should not be construed to limit the present technology to the specific embodiments disclosed in the specification, unless the above Detailed Description section explicitly defines such terms. Accordingly, the actual scope of the present technology encompasses not only the disclosed embodiments, but also all equivalent ways of practicing or implementing the present technology.

We claim:

1. A method of treating pain comprising:
   pulsing heat into a volume of tissue including thermoreceptors, wherein—
   the pulsed heat is between 42 degrees and 49 degrees Celsius,
   the pulsed heat is configured to stimulate the thermoreceptors,
   the pulsed heat comprises a heat cycle including a ramp-up phase, a hold phase, and a soak phase,
   the ramp-up phase has a duration of about 4 seconds or less,
   the hold phase has a duration of about 10 seconds or less, and
   the soak phase has a duration of about 20 seconds or less; and
   iteratively repeating the heat cycle at a frequency configured to induce and maintain desensitization of at least a subset of the thermoreceptors.

2. The method of claim 1, wherein the hold phase includes applying heat to the tissue at a temperature between 42 degrees and 49 degrees Celsius.

3. The method of claim 1, wherein the soak phase includes applying heat at a basal body temperature or not applying heat.

4. The method of claim 1, wherein the heat cycle is iteratively repeated for a set duration.

5. The method of claim 1, wherein the heat cycle is configured to desensitize at least a subset of the thermoreceptors.

6. The method of claim 1, wherein the pulsed heat is configured to stimulate and/or induce desensitization of both warm thermoreceptors and cold thermoreceptors.

7. The method of claim 1, wherein the pulsed heat is configured to stimulate and/or induce desensitization of TRPV1 receptors.

8. The method of claim 1, wherein the pulsed heat is configured to stimulate and/or induce desensitization of TRPM8 receptors and/or TRPA1 receptors.

9. The method of claim 1, wherein the pulsed heat is applied to at least one continuous surface area of the tissue that is 3 square inches or less.

10. The method of claim 1 wherein the duration of the hold phase is about 8 seconds or less.

11. The method of claim 1 wherein the duration of the soak phase is about 10 seconds or less.

12. The method of claim 1 wherein the duration of the hold phase is about 8 seconds or less, and wherein the duration of the soak phase is about 10 seconds or less.

13. A method of treating pain comprising:
    applying energy to a volume of tissue including thermoreceptors, wherein—
    the applied energy induces a skin temperature between 42 degrees and 49 degrees Celsius,
    the applied energy induces a thermal flux in the skin that is below a tissue-damaging threshold,
    the applied energy induces stimulation of thermoreceptors,
    the applied energy comprises a cycle including a ramp-up phase, a hold phase, and a soak phase,
    the ramp-up phase has a duration of about 4 seconds or less,
    the hold phase has a duration of about 10 seconds or less, and
    the soak phase has a duration of about 20 seconds or less; and
    iteratively repeating the cycle at a frequency configured to induce and maintain desensitization of at least a subset of the thermoreceptors.

14. The method of claim 13, wherein, during the hold phase, energy is applied to the volume of tissue to induce the skin temperature between 42 degrees and 49 degrees Celsius.

15. The method of claim 13, wherein the soak phase comprises applying no energy to the volume of tissue, and wherein, during the soak phase, the temperature of the skin falls below 42 degrees Celsius.

16. The method of claim 13, wherein the cycle is iteratively repeated for a set duration.

17. The method of claim 13, wherein the cycle is configured to desensitize at least a subset of the thermoreceptors.

18. The method of claim 13, wherein the energy is configured to stimulate and/or induce desensitization of both warm thermoreceptors and cold thermoreceptors.

19. The method of claim 13, wherein the applied energy is configured to stimulate and/or induce desensitization of TRPV1 receptors.

20. The method of claim 13, wherein the applied energy is configured to stimulate and/or induce desensitization of TRPM8 receptors and/or TRPMA1 receptors.

21. The method of claim 13 wherein the duration of the hold phase is about 8 seconds or less.

22. The method of claim 13 wherein the duration of the soak phase is about 10 seconds or less.

23. The method of claim 13 wherein the duration of the hold phase is about 8 seconds or less, and wherein the duration of the soak phase is about 10 seconds or less.

24. A system for treating pain, the system comprising:
an energy producing element having a stimulus surface, wherein the stimulus surface is configured to be placed in contact with skin, and wherein the energy producing element is configured to pulse energy into the skin via the stimulus surface,
wherein the pulsed energy comprises a cycle including a ramp-up phase, a hold phase, and a soak phase,
wherein the ramp-up phase has a duration of about 4 seconds or less,
wherein the hold phase has a duration of about 10 seconds or less,
wherein the soak phase has a duration of about 20 seconds or less,
wherein the pulsed energy is configured to stimulate thermoreceptors within the skin, and
wherein the cycle is iteratively repeated at a frequency configured to induce and maintain desensitization of at least a subset of the thermoreceptors.

25. The system of claim 24, further comprising an electrical circuit configured to monitor the temperature of the skin to ensure that the pulsed energy does not cause an injury to the skin.

26. The system of claim 25, wherein the electrical circuit is configured to utilize a look-up table, a formula, a chart, or other source of information to predict the characteristic of thermal energy that causes injury to the skin.

27. The system of claim 25, further comprising a temperature measuring element configured to sense the temperature of the skin.

28. The system of claim 25, wherein the electrical circuit is configured to transmit monitored characteristics to a control device.

29. The system of claim 28, wherein the monitored characteristics include the skin's thermal transfer capacity and/or the skin's blood flow.

30. The system of claim 24, wherein the pulsed energy is configured to induce a skin temperature between 42 degrees and 49 degrees Celsius.

31. The system of claim 24, wherein the subset of thermoreceptors includes TRPV1, TRPM8, and/or TRPA1.

* * * * *